(12) United States Patent
Hood et al.

(10) Patent No.: US 8,898,069 B2
(45) Date of Patent: Nov. 25, 2014

(54) DEVICES AND METHODS FOR DETECTING AN ANALYTE IN SALIVARY FLUID

(75) Inventors: Leroy E. Hood, Seattle, WA (US); Edward K. Y. Jung, Bellevue, WA (US); Elizabeth A. Sweeney, Seattle, WA (US); Clarence T. Tegreene, Bellevue, WA (US); Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 379 days.

(21) Appl. No.: 12/584,055

(22) Filed: Aug. 28, 2009

(65) Prior Publication Data

US 2011/0054938 A1 Mar. 3, 2011

Related U.S. Application Data

(63) Continuation-in-part of application No. 12/584,054, filed on Aug. 28, 2009, now Pat. No. 8,810,417.

(51) Int. Cl.
| | |
|---|---|
| *G06Q 10/00* | (2012.01) |
| *G06Q 50/00* | (2012.01) |
| *G06Q 50/24* | (2012.01) |
| *A61B 5/00* | (2006.01) |

(52) U.S. Cl.
CPC .............. *A61B 5/0002* (2013.01); *G06Q 50/24* (2013.01); *A61B 5/411* (2013.01); *A61B 5/00* (2013.01)
USPC .......................................................... 705/2

(58) Field of Classification Search
CPC .. A61B 6/145; A61B 5/14532; A61B 6/4423; A61B 10/0012; A61B 10/0051; A61B 2562/0209; A61B 5/14528; A61B 5/4277; A61B 5/4839; A61B 10/0045; A61B 5/0088; A61B 5/14546; A61B 5/4542; A61B 5/682; A61F 5/566
See application file for complete search history.

(56) References Cited

U.S. PATENT DOCUMENTS

| | | |
|---|---|---|
| 4,275,083 A | 6/1981 | Colten et al. |
| 4,843,830 A | 7/1989 | Haul |

(Continued)

FOREIGN PATENT DOCUMENTS

| | | |
|---|---|---|
| EP | 1 397 997 A1 | 3/2004 |
| WO | WO 99/31560 | 6/1999 |

(Continued)

OTHER PUBLICATIONS

Abràmoff, Michael D., et al.; "Image Processing with ImageJ"; Biophotonics International; Bearing a date of Jul. 2004; pp. 36-42; The British Library.

(Continued)

*Primary Examiner* — Michelle L Le
(74) *Attorney, Agent, or Firm* — Dorsey & Whitney LLP

(57) ABSTRACT

Methods and systems are described herein for detecting one or more analyte in salivary fluid. Systems include: a discrete oral component configured for complete enclosure in a human oral cavity; at least one sensor configured to detect one or more analyte in salivary fluid; and an external device including a port configured for communication with the discrete oral component. Methods include: detecting one or more analyte within salivary fluid with at least one sensor integral to a discrete oral component, wherein the discrete oral component is configured to be completely enclosed in the oral cavity and includes one or more flavorant; and communicating information from the discrete oral component to at least one external device.

40 Claims, 18 Drawing Sheets

(56) References Cited

U.S. PATENT DOCUMENTS

| | | | |
|---|---|---|---|
| 5,174,962 A | 12/1992 | Brennan | |
| 5,183,740 A | 2/1993 | Ligler et al. | |
| 5,303,585 A | 4/1994 | Lichte | |
| 5,354,654 A | 10/1994 | Ligler et al. | |
| 5,360,819 A | 11/1994 | Giese | |
| 5,475,096 A | 12/1995 | Gold et al. | |
| 5,516,931 A | 5/1996 | Giese et al. | |
| 5,571,401 A | 11/1996 | Lewis et al. | |
| 5,602,273 A | 2/1997 | Giese et al. | |
| 5,604,104 A | 2/1997 | Giese et al. | |
| 5,610,020 A | 3/1997 | Giese et al. | |
| 5,631,146 A | 5/1997 | Szostak et al. | |
| 5,661,039 A | 8/1997 | Kung et al. | |
| 5,762,939 A | 6/1998 | Smith et al. | |
| 5,804,563 A | 9/1998 | Still et al. | |
| 5,807,758 A | 9/1998 | Lee et al. | |
| 5,831,012 A | 11/1998 | Nilsson et al. | |
| 6,022,326 A | 2/2000 | Tatum et al. | |
| 6,102,872 A * | 8/2000 | Doneen et al. | 600/582 |
| 6,163,248 A | 12/2000 | Paek et al. | |
| 6,187,599 B1 | 2/2001 | Asher et al. | |
| 6,214,546 B1 | 4/2001 | Asher et al. | |
| 6,255,461 B1 | 7/2001 | Mosbach et al. | |
| 6,258,870 B1 | 7/2001 | Hubbell et al. | |
| 6,310,105 B1 | 10/2001 | Damodaran | |
| 6,372,248 B1 | 4/2002 | Qin et al. | |
| 6,397,190 B1 | 5/2002 | Goetz | |
| 6,467,333 B2 | 10/2002 | Lewis et al. | |
| 6,468,223 B2 * | 10/2002 | Kaga | 600/551 |
| 6,491,643 B2 | 12/2002 | Katzman et al. | |
| 6,528,954 B1 | 3/2003 | Lys et al. | |
| 6,544,800 B2 | 4/2003 | Asher | |
| 6,558,320 B1 * | 5/2003 | Causey et al. | 600/300 |
| 6,609,068 B2 | 8/2003 | Cranley et al. | |
| 6,623,698 B2 * | 9/2003 | Kuo | 422/68.1 |
| 6,635,452 B1 | 10/2003 | Monforte et al. | |
| 6,670,427 B1 | 12/2003 | Ulbricht et al. | |
| 6,746,529 B1 | 6/2004 | Witteveen et al. | |
| 6,753,191 B2 | 6/2004 | Asher et al. | |
| 6,754,472 B1 | 6/2004 | Williams et al. | |
| 6,797,522 B1 | 9/2004 | Still et al. | |
| 6,821,331 B2 | 11/2004 | Damodaran | |
| 6,949,347 B2 | 9/2005 | Singh et al. | |
| 6,953,589 B1 | 10/2005 | Trautman et al. | |
| 7,022,514 B2 | 4/2006 | Vodyanoy et al. | |
| 7,105,352 B2 | 9/2006 | Asher et al. | |
| 7,247,489 B2 | 7/2007 | Bakker et al. | |
| 7,288,415 B2 | 10/2007 | Huang | |
| 7,292,349 B2 | 11/2007 | Miller et al. | |
| 7,314,453 B2 | 1/2008 | Kuo | |
| 7,402,423 B2 | 7/2008 | Taghizadeh et al. | |
| 7,442,754 B2 | 10/2008 | Tepper et al. | |
| 7,459,713 B2 | 12/2008 | Coates | |
| 7,483,805 B2 | 1/2009 | Sparks et al. | |
| 7,555,437 B2 | 6/2009 | Pierce | |
| 7,563,026 B2 * | 7/2009 | Mandelkern et al. | 378/191 |
| 7,576,319 B2 | 8/2009 | Miller et al. | |
| 7,610,804 B2 | 11/2009 | Ramus et al. | |
| 7,647,237 B2 | 1/2010 | Malave et al. | |
| 7,722,536 B2 | 5/2010 | Goodnow | |
| 7,736,310 B2 | 6/2010 | Taub | |
| 7,766,658 B2 * | 8/2010 | Tricca et al. | 433/229 |
| 7,813,780 B2 * | 10/2010 | Shah et al. | 600/345 |
| 7,860,727 B2 | 12/2010 | Showalter et al. | |
| 8,241,575 B2 | 8/2012 | Murray et al. | |
| 2002/0044891 A1 | 4/2002 | Miller et al. | |
| 2002/0127143 A1 | 9/2002 | Kuo | |
| 2003/0022225 A1 | 1/2003 | Monforte et al. | |
| 2003/0023189 A1 | 1/2003 | Kuo | |
| 2003/0034895 A1 | 2/2003 | Reich | |
| 2003/0062909 A1 | 4/2003 | Liao | |
| 2003/0138939 A1 | 7/2003 | Vodyanoy et al. | |
| 2003/0143580 A1 | 7/2003 | Straus | |
| 2004/0006257 A1 | 1/2004 | Burch et al. | |
| 2004/0018508 A1 | 1/2004 | Friedman | |
| 2004/0078219 A1 | 4/2004 | Kaylor et al. | |
| 2004/0100376 A1 | 5/2004 | Lye et al. | |
| 2004/0115132 A1 | 6/2004 | Young et al. | |
| 2004/0162467 A1 | 8/2004 | Cook | |
| 2005/0037112 A1 | 2/2005 | Daley et al. | |
| 2005/0143787 A1 | 6/2005 | Boveja et al. | |
| 2006/0033631 A1 | 2/2006 | Cupples et al. | |
| 2006/0204444 A1 | 9/2006 | Young et al. | |
| 2006/0292174 A1 | 12/2006 | de los Rios et al. | |
| 2007/0021458 A1 | 1/2007 | Ishikawa et al. | |
| 2007/0059245 A1 | 3/2007 | Young et al. | |
| 2007/0146154 A1 | 6/2007 | Teller | |
| 2007/0190084 A1 | 8/2007 | Hilt et al. | |
| 2007/0254260 A1 * | 11/2007 | Alden et al. | 433/85 |
| 2008/0102953 A1 | 5/2008 | Schultz | |
| 2008/0175963 A1 | 7/2008 | Pope | |
| 2008/0265146 A1 | 10/2008 | Coates | |
| 2008/0283538 A1 | 11/2008 | Rowen | |
| 2008/0294061 A1 | 11/2008 | Wang et al. | |
| 2008/0300569 A1 | 12/2008 | Schateikis et al. | |
| 2008/0303678 A1 | 12/2008 | McCredy | |
| 2009/0120038 A1 | 5/2009 | Abercrombie, III et al. | |
| 2009/0149988 A1 | 6/2009 | Hyde et al. | |
| 2009/0170124 A1 * | 7/2009 | Campbell | 435/7.2 |
| 2009/0247857 A1 * | 10/2009 | Harper et al. | 600/365 |
| 2010/0089152 A1 | 4/2010 | Kolada et al. | |
| 2011/0054801 A1 | 3/2011 | Hilborne et al. | |

FOREIGN PATENT DOCUMENTS

| | | |
|---|---|---|
| WO | WO 2007/113727 A2 | 10/2007 |
| WO | WO 2008/006152 A1 | 1/2008 |

OTHER PUBLICATIONS

Alexeev, Vladimir L., et al.; "Photonic Crystal Glucose-Sensing Material for Noninvasive Monitoring of Glucose in Tear Fluid"; Clinical Chemistry; Bearing a date of 2004; pp. 2353-2360; vol. 50, No. 12; American Association for Clinical Chemistry.

Asher Research Group; "Colloid Group"; Printed on Jul. 31, 2009; pp. 1-14; located at http://www.pitt.edu/~asher/homepage/colgrp.html.

Baker, Brian R., et al.; "An Electronic, Aptamer-Based Small-Molecule Sensor for the Rapid, Label-Free Detection of Cocaine in Adulterated Samples and Biological Fluids"; Journal of the American Chemical Society; Bearing a date of Feb. 18, 2006; pp. 3138-3139; vol. 128; American Chemical Society.

Baker, Monya; "From the Lab: Biotechnology; Beaming Biodata: Mutation detection goes wireless"; MIT Technology Review; Bearing a date of May 2005; pp. 1-5.

Balon, Helena R., et al.; "Society of Nuclear Medicine Procedure Guideline for C-14 Urea Breath Test"; Society of Nuclear Medicine Procedure Guidelines Manual; Bearing a date of Jun. 2002; pp. 37-39.

Bauer, Susan; "Saliva spits out information on chemical exposure"; PNNL News Release; Bearing a date of Oct. 24, 2003; Printed on Jul. 31, 2009; pp. 1-2; located at http://www.innovations-report.com/html/reports/life_sciences/report-22741.html.

Ben-Moshe, Matti, et al.; "Fast Responsive Crystalline Colloidal Array Photonic Crystal Glucose Sensors"; Analytical Chemistry; Bearing a date of Jul. 15, 2006; pp. 5149-5157; vol. 78, No. 14; American Chemical Society.

Besanger, Travis R., et al.; "Screening of Inhibitors Using Enzymes Entrapped in Sol-Gel-Derived Materials"; Analytical Chemistry; Bearing a date of May 15, 2003; pp. 2382-2391; vol. 75, No. 10; American Chemical Society.

Biohesion Incorporated; "Advanced Surface Binding Technology"; Bearing a date of 2007; p. 1 of 1; located at http://www.biohesion.com/.

Boisen, Anja, et al.; "Rapid molecular detection of food- and water-borne diseases"; Microbiology Today; Bearing a date of Aug. 2007; pp. 116-118.

Bromberg, Lev; "Intelligent Polyelectrolytes and Gels in Oral Drug Delivery"; Current Pharmaceutical Biotechnology; Bearing a date of 2003; pp. 339-349; vol. 4, No. 5; Bentham Science Publishers Ltd.

(56) References Cited

OTHER PUBLICATIONS

Bruno, John G., et al.; "Use of Magnetic Beads in Selection and Detection of Biotoxin Aptamers by Electrochemiluminescence and Enzymatic Methods"; BioTechniques; Bearing a date of Jan. 2002; pp. 178-183; vol. 32, No. 1.

Byrne, Mark E., et al.; "Molecular imprinting within hydrogels"; Advanced Drug Delivery Reviews; Bearing a date of 2002; pp. 149-161; vol. 54; Elsevier Science B.V.

Chen, Chao-Tsen, et al.; "Fluorescent, Sequence-Selective Peptide Detection by Synthetic Small Molecules"; Science; Bearing a date of Feb. 6, 1998; pp. 851-853; vol. 279.

Daunert, Sylvia, et al.; "Genetically Engineered Whole-Cell Sensing Systems: Coupling Biological Recognition with Reporter Genes"; Chemical Reviews; Bearing a date of 2000; pp. 2705-2738; vol. 100, No. 7; American Chemical Society.

Dill, Kilian, et al.; "Immunoassays and sequence-specific DNA detection on a microchip using enzyme amplified electrochemical detection"; Journal of Biochemical and Biophysical Methods; Bearing a date of 2004; pp. 181-187; vol. 59; Elsevier B.V.

Drafts, Bill; "Acoustic Wave Technology Sensors"; Sensors; Bearing a date of Oct. 1, 2000; Printed on Jul. 31, 2009; pp. 1-9; located at http://www.sensorsmag.com/articles/1000/68/main.shtml.

Drummond, T Gregory, et al.; "Electrochemical DNA sensors"; Nature Biotechnology; Bearing a date of Oct. 2003; pp. 1192-1199; vol. 21, No. 10; Nature Publishing Group.

Dwarakanath, Sulatha, et al.; "Quantum dot-antibody and aptamer conjugates shift fluorescence upon binding bacteria"; Biochemical and Biophysical Research Communications; Bearing a date of 2004; pp. 739-743; vol. 325; Elseveir Inc.

Ehrick, Jason D., et al.; "Genetically engineered protein in hydrogels tailors stimuli-responsive characteristics"; Nature Materials; Bearing a date of Apr. 2005; pp. 298-302; vol. 4; Nature Publishing Group.

Gao, Liang, et al.; "Design and Characterization of a Multisource Hand-Held Tandem Mass Spectrometer"; Analytical Chemistry; Bearing a date of Oct. 1, 2008; pp. 7198-7205; vol. 80, No. 19; American Chemical Society.

Garrison, Kenneth E., et al.; "A review of membrane sampling from biological tissues with applications in pharmacokinetics, metabolism and pharmacodynamics"; European Journal of Pharmaceutical Sciences; Bearing a date of 2002; pp. 1-12; vol. 17; Elsevier Science B.V.

Gelfand, Alexander; "Device Offers a Roadside Dope Test"; MIT Technology Review; Bearing a date of Aug. 4, 2009; pp. 1-4.

Gonzalez, Anjelica L., et al.; "Integrin Interactions with Immobilized Peptides in Polyethylene Glycol Diacrylate Hydrogels"; Tissue Engineering; Bearing a date of 2004; pp. 1775-1786; vol. 10, No. 11/12.

Hagleitner, C., et al.; "Smart single-chip gas sensor microsystem"; Nature; Bearing a date of Nov. 15, 2001; pp. 293-296; vol. 414; Macmillan Magazines Ltd.

Heim, Sarah J.; "Lab on a Swab"; MIT Technology Review; Bearing a date of Aug. 29, 2005; pp. 1-4; located at http://www.technologyreview.com/biomedicine/14709/.

Heine, R. Phillip, et al.; "Accuracy of salivary estriol testing compared to traditional risk factor assessment in predicting preterm birth"; American Journal of Obstetrics and Gynecology; Bearing a date of Jan. 1999; pp. 214S-218S; vol. 180(1S-III).

Herber, Sebastiaan, et al.; "A hydrogel-based CO2 sensor"; MESA+ Institute for Nanotechnology, University of Twente; Bearing a date of Aug. 29, 2005; Printed on Jul. 31, 2009; pp. 1-2; located at http://bios.ewi.utwente.nl/research/electrochemicalsystems/formeranalysissystemsandsensorsprojects/ahydrogelbased.doc/index.html.

Hitachi, Ltd.; "Development of world's first RFID sensor chip for DNA analysis"; Press Release; Bearing a date of Feb. 10, 2005; pp. 1-4.

Hodinka, R. L., et al.; "Detection of Human Immunodeficiency Virus Antibodies in Oral Fluids"; Clinical and Diagnostic Laboratory Immunology; Bearing a date of Jul. 1998; pp. 419-426; vol. 5, No. 4; American Society for Microbiology.

Hofman, Lindsay F.; "Human Saliva as a Diagnostic Specimen"; Journal of Nutrition; Bearing a date of 2001; pp. 1621S-1625S; vol. 131; American Society for Nutritional Sciences.

Holtz, John H., et al.; "Polymerized colloidal crystal hydrogel films as intelligent chemical sensing materials"; Nature; Bearing a date of Oct. 23, 1997; pp. 829-832; vol. 389; Macmillan Publishers Ltd.

Horner, Scott R., et al.; "A proteomic biosensor for enteropathogenic E. coli"; Biosensors and Bioelectronics; Bearing a date of 2006; pp. 1659-1663; vol. 21; Elsevier B.V.

Indo-Asian News Service; "Scientists develop biosensor to detect E. coli bacteria"; RxPG News; Bearing dates of Feb. 25, 2006 and Aug. 19, 2006; Printed on Jul. 31, 2009; pp. 1-3; located at http://www.rxpgnews.com/article_3524.shtml.

Karjalainen, S., et al.; "Salivary Cholesterol of Healthy Adults in Relation to Serum Cholesterol Concentration and Oral Health"; Journal of Dental Research; Bearing a date of Oct. 1997; pp. 1637-1643; vol. 76, No. 10; Sage Publications.

Katagiri, Kiyofumi, et al.; "Creation of asymmetric bilayer membrane on monodispersed colloidal silica particles"; Colloids and Surfaces B: Biointerfaces; Bearing a date of 2004; pp. 149-153; vol. 38; Elsevier B.V.

Kaufman, Eliaz, et al.; "The Diagnostic Applications of Saliva—A Review"; Critical Reviews in Oral Biology & Medicine; Bearing a date of 2002; pp. 197-212; vol. 13, No. 2.

Kharitonov, Sergei A., et al.; "Exhaled Markers of Pulmonary Disease"; American Journal of Respiratory and Critical Care Medicine; Bearing a date of 2001; pp. 1693-1722; vol. 163.

Khurana, Surender, et al.; "Antigenic Fingerprinting of H5N1 Avian Influenza Using Convalescent Sera and Monoclonal Antibodies Reveals Potential Vaccine and Diagnostic Targets"; PLoS Medicine; Bearing a date of Apr. 2009; pp. 1-13; vol. 6, No. 4.

Kimo Instruments; "Hand-held carbon dioxide (CO2) analyzer, CO, CO2, ° C., %HR"; Printed on Aug. 27, 2009; pp. 1; located at http://www.directindustry.com/prod/kimo/hand-held-carbon-dioxide-co2-analyzer-11846-389510.html.

Korsman, Stephen; "Chapter 6: Vaccines"; Influenza Report 2006 Edited by Kamps et al.; Bearing a date of 2006; pp. 1-4, and 127-149; Flying Publisher.

Kumar, Ashok; "Biosensors Based on Piezoelectric Crystal Detectors: Theory and Application"; JOM-e; Bearing a date of Oct. 2000; Printed on Jul. 31, 2009; pp. 1-9; vol. 52, No. 10; located at http://www.tms.org/pubs/journals/JOM/0010/Kumar/Kumar-0010.html.

Lai, Rebecca Y., et al.; "Aptamer-Based Electrochemical Detection of Picomolar Platelet-Derived Growth Factor Directly in Blood Serum"; Analytical Chemistry; Bearing a date of Jan. 1, 2007; pp. 229-233; vol. 79, No. 1; American Chemical Society.

Lai, Rebecca Y., et al.; "Differential Labeling of Closely Spaced Biosensor Electrodes via Electrochemical Lithography"; Langmuir; Bearing a date of 2006; pp. 1932-1936; vol. 22; American Chemical Society.

Lakshmi, Dhana, et al.; "Electrochemical Sensor for Catechol and Dopamine Based on a Catalytic Molecularly Imprinted Polymer-Conducting Polymer Hybrid Recognition Element"; Analytical Chemistry; Bearing a date of May 1, 2009; pp. 3576-3584; vol. 81, No. 9; American Chemical Society.

Lavigne, John J., et al.; "Solution-Based Analysis of Multiple Analytes by a Sensor Array: Toward the Development of an 'Electronic Tongue'"; Journal of the American Chemical Society; Bearing a date of Jul. 1998; pp. 6429-6430; vol. 120; American Chemical Society.

Lawrence, Herenia P.; "Salivary Markers of Systemic Disease: Noninvasive Diagnosis of Disease and Monitoring of General Health"; Journal of the Canadian Dental Association; Bearing a date of Mar. 2002; pp. 170-174; vol. 68, No. 3.

Lee, Jeong-O, et al.; "Aptamers as molecular recognition elements for electrical nanobiosensors"; Analytical and Bioanalytical Chemistry; Bearing a date of 2008; pp. 1023-1032; vol. 390; Springer-Verlag.

Lempert, Phil; "Digital house calls? Check your health at home"; MSNBC.com; Bearing a date of Feb. 21, 2006; p. 1 of 1; located at http://www.msnbc.msn.com/id/11476436/.

(56) References Cited

OTHER PUBLICATIONS

Li, Y., et al.; "The Oral Fluid MEMS/NEMS Chip (OFMNC): Diagnostic & Translational Applications", Advances in Dental Research; Bearing a date of 2005; pp. 3-5; vol. 18; Sage.
Liu, Chung-Chiun; "Applications of Microfabrication Techniques in Electrochemical Sensor Development"; Applied Biochemistry and Biotechnology; Bearing a date of 1993; pp. 99-107; vol. 41; The Humana Press Inc.
Liu, Ke, et al.; "Detection of $Pb^{2+}$ Using a Hydrogel Swelling Microcantilever Sensor"; Analytical Sciences; Bearing a date of Jan. 2004; pp. 9-11; vol. 20; The Japan Society for Analytical Chemistry.
MiScope Handheld Digital Microscope; "Description"; Forensics Source; Printed on Aug. 27, 2009; pp. 1; located at http://www.forensicssource.com/p-1810-miscope-handheld-digital-microscope.aspx.
Miyata, Takashi, et al.; "A reversibly antigen-responsive hydrogel"; Nature; Bearing a date of Jun. 24, 1999; pp. 766-769; vol. 399; Macmillan Magazines Ltd.
Miyawaki, Atsushi, et al.; "Fluorescent indicators for $Ca^{2+}$ based on green fluorescent proteins and calmodulin"; Nature; Bearing a date of Aug. 28, 1997; pp. 882-887; vol. 388; Macmillan Publishers Ltd.
Moldoveanu, Z., et al.; "Human immune responses to influenza virus vaccines administered by systemic or mucosal routes"; Vaccine; Bearing a date of 1995; pp. 1006-1012; vol. 13, No. 11; Elsevier Science Ltd.
Murthy, S. Narasimha, et al.; "Physical and Chemical Permeation Enhancers in Transdermal Delivery of Terbutaline Sulphate"; AAPS PharmSciTech; Bearing a date of 2001; pp. 1-5; vol. 2, No. 1.
Musa-Veloso, Kathy, et al.; "Breath acetone is a reliable indicator of ketosis in adults consuming ketogenic meals"; The American Journal of Clinical Nutrition; Bearing a date of 2002; pp. 65-70; vol. 76; American Society for Clinical Nutrition.
Nishanian, Parunag, et al.; "Oral Fluids as an Alternative to Serum for Measurement of Markers of Immune Activation"; Clinical and Diagnostic Laboratory Immunology; Bearing a date of Jul. 1998; pp. 507-512; vol. 5, No. 4; American Society for Microbiology.
Overhoff Technology Corporation; "All Purpose, Affordable, Beta/Gamma Meter With a Sensitivity to 1 µR/h!; Ion Ferret Gamma/Beta Detector Ionization Chamber/Survey Meter"; Printed on Aug. 27, 2009; pp. 1-2.
Pathak, C.M., et al.; "Urea Breath Test for *Helicobacter pylori* Detection: Present Status"; Tropical Gastroenterology; Bearing a date of Oct.-Dec. 2004; pp. 156-161; vol. 25, No. 4.
Peppas, Nicholas A., et al.; "Polymers and Gels as Molecular Recognition Agents"; Pharmaceutical Research; Bearing a date of May 2002; pp. 578-587; vol. 19, No. 5; Plenum Publishing Corporation.
Potter, Steve M., et al.; "A new approach to neural cell culture for long-term studies"; Journal of Neuroscience Methods; Bearing a date of 2001; pp. 17-24; vol. 110; Elsevier Science B.V.
Queyras, Armelle, et al.; "Non-invasive techniques for analysing hormonal indicators of stress"; Annali dell'Istituto Superiore di Sanita; Bearing a date of 2004; pp. 211-221; vol. 40, No. 2.
Quickmedical Medical Equipment and Supplies; "AlcoHawk CA2000—Premium Digital Alcohol Breath Analyzer"; Printed on Jul. 31, 2009; pp. 1-4; located at http://www.quickmedical.com/breathalyzer/alcoscan_tech.html.
Quickmedical Medical Equipment and Supplies; "Digital Alcohol Breathalyzer—AlcoHawk ABI Premium"; Printed on Jul. 31, 2009; pp. 1-3; located at http://www.quickmedical.com/breathalyzer/alcoscan.html.
Rädler, Ulf, et al.; "Design of Supported Membranes Tethered via Metal-Affinity Ligand-Receptor Pairs"; Biophysical Journal; Bearing a date of Dec. 2000; pp. 3144-3152; vol. 79; Biophysical Society.
Rider, Todd H., et al.; "A B Cell-Based Sensor for Rapid Identification of Pathogens"; Science; Bearing a date of Jul. 11, 2003; pp. 213-215; vol. 301.
Savran, Cagri A., et al.; "Micromechanical Detection of Proteins Using Aptamer-Based Receptor Molecules"; Analytical Chemistry; Bearing a date of Jun. 1, 2004; pp. 3194-3198; vol. 76, No. 11; American Chemical Society.
Science Daily; "Salivary Diagnostics, The 'Magic Mirror' to Your Health . . . At Your Personal Computer"; Bearing a date of Apr. 5, 2008; pp. 1-2; located at http://www.sciencedaily.com/releases/2008/04/080405095750.htm.
Senel, Sevda, et al.; "Drug permeation enhancement via buccal route: possibilities and limitations"; Journal of Controlled Release; Bearing a date of 2001; pp. 133-144; vol. 72; Elsevier Science B.V.
Skelley, Alison M., et al.; "Development and evaluation of a microdevice for amino acid biomarker detection and analysis on Mars"; PNAS; Bearing a date of Jan. 25, 2005; pp. 1041-1046; vol. 102, No. 4; The National Academy of Sciences of the USA.
Snow, E. S., et al.; "Chemical Detection with a Single-Walled Carbon Nanotube Capacitor"; Science; Bearing a date of Mar. 25, 2005; pp. 1942-1945; vol. 307.
Sotiropoulou, Sofia, et al.; "Stabilization of enzymes in nanoporous materials for biosensor applications"; Biosensors and Bioelectronics; Bearing a date of 2005; pp. 1674-1679; vol. 20; Elsevier B.V.
SPI Pharma Group; "New Formulation Makes Gum Delivery System Efficient and Affordable"; Special Delivery: The quarterly newsletter from SPI Pharma Group; Bearing a date of Summer 2001; pp. 1-4.
Stojanovic, Milan N., et al.; "Aptamer-Based Folding Fluorescent Sensor for Cocaine"; Journal of the American Chemical Society; Bearing a date of 2001; pp. 4928-4931; vol. 123, No. 21; American Chemical Society.
Tanaka, Toyoichi, et al.; "Polymer Gels that can Recognize and Recover Molecules"; Faraday Discussions; Bearing a date of 1996; pp. 201-206; vol. 102.
Tolosa, Leah, et al.; "Lifetime-Based Sensing of Glucose Using Energy Transfer with a Long Lifetime Donor"; Analytical Biochemistry; Bearing a date of 1997; pp. 102-108; vol. 250; Academic Press.
Tombelli, Sara, et al.; "Piezoelectric biosensors: Strategies for coupling nucleic acids to piezoelectric devices"; Methods; Bearing a date of 2005; pp. 48-56; vol. 37; Elsevier Inc.
U.S. Department of Energy, Office of Environmental Management, Office of Science and Technology; "Innovative Technology Summary Report, Lumi-Scint Liquid Scintillation Counter"; Bearing a date of Jul. 2001; Four pages plus pp. 1-24.
U.S. Department of Health and Human Services, Centers for Disease Control and Prevention, National Center for Health Statistics; Table 3, Table 4 and Table V from "Summary Health Statistics for U.S. Adults: National Health Interview Survey, 2003"; Bearing a date of Jul. 2005; pp. 1-4, 20-23, and 112-113.
U.S. Department of Health and Human Services, Centers for Disease Control and Prevention, National Center for Health Statistics; Table 1 from "Summary Health Statistics for U.S. Children: National Health Interview Survey, 2003"; Bearing a date of Mar. 2005; pp. 1-4, and 8-9.
Utada, A. S., et al.; "Monodisperse Double Emulsions Generated from a Microcapillary Device"; Science; Bearing a date of Apr. 22, 2005; pp. 537-541; vol. 308.
Vamvakaki, Vicky, et al.; "Fluorescence detection of enzymatic activity within a liposome based nano-biosensor"; Biosensors and Bioelectronics; Bearing a date of 2005; pp. 384-388; vol. 21; Elsevier B.V.
Vass, Géza, et al.; "Comparison of Nasal and Oral Inhalation during Exhaled Breath Condensate Collection"; American Journal of Respiratory and Critical Care Medicine; Bearing a date of 2003; pp. 850-855; vol. 167.
Vital Sensors Technologies LLC; "VS-1000B Series Inline Brix Sensors for the Beverage Industry; Inline Networked Smart Infrared Sensors for Real-Time Process Monitoring: Continuous Accurate Brix measurement of Regular and Diet Beverages"; Bearing a date of 2008; pp. 1-4.
Walker, Richard F., et al.; "Radioimmunoassay of Progesterone in Saliva: Application to the Assessment of Ovarian Function"; Clinical Chemistry; Bearing a date of 1979; pp. 2030-2033; vol. 25, No. 12.
Wee, Kyung Wook, et al.; "Novel electrical detection of label-free disease marker proteins using piezoresistive self-sensing micro-cantilevers"; Biosensors and Bioelectronics; Bearing a date of 2005; pp. 1932-1938; vol. 20; Elsevier B.V.
Wikipedia; "Taste"; Bearing a date of May 19, 2009; Printed on May 22, 2009; pp. 1-10; located at http://en.wikipedia.org/wiki/Taste.

(56) References Cited

OTHER PUBLICATIONS

Win, Maung Nyan, et al.; "Codeine-binding RNA aptamers and rapid determination of their binding constants using a direct coupling surface plasmon resonance assay"; Nucleic Acids Research; Bearing a date of 2006; pp. 5670-5682; vol. 34, No. 19.

Wong, David T.; "Oral Fluid NanoSensor Test (OFNASET)"; Bearing a date of Sep. 1, 2006; located at http://www.researchgrantdatabase.com/g/5U01DE017790-03/Oral-Fluid-NanoSensor-Test-OFNASET/ [Abstract Only].

Wong, David T.; "Salivary diagnostics powered by nanotechnologies, proteomics and genomics"; Journal of the American Dental Association; Bearing a date of 2006; pp. 313-321; vol. 137; American Dental Association.

Yazawa, Yoshiaki, et al.; "A Wireless Biosensing Chip for DNA Detection"; 2005 IEEE International Solid-State Circuits Conference, Session 30, Displays and Biosensors, 30.6; Bearing a date of 2005; pp. 562-563, and 617.

Ye, Lei, et al.; "Molecularly imprinted polymers as antibody and receptor mimics for assays, sensors and drug discovery"; Analytical and Bioanalytical Chemistry; Bearing a date of 2004; pp. 1887-1897; vol. 378.

Yoon, Min-Sung, et al.; "Characterisation of advanced glycation endproducts in saliva from patients with diabetes mellitus"; Biochemical and Biophysical Research Communications; Bearing a date of 2004; pp. 377-381; vol. 323; Elsevier Inc.

Yusa, Go, et al.; "Controlled multiple quantum coherences of nuclear spins in a nanometre-scale device"; Nature; Bearing a date of Apr. 21, 2005; pp. 1001-1005; vol. 434; Nature Publishing Group.

U.S. Appl. No. 12/657,166, Hood et al.

U.S. Appl. No. 12/584,054, Hood et al.

U.S. Appl. No. 12/584,364, Hood et al.

Balmaseda, Angel, et al.; "Diagnosis of Dengue Virus Infection by Detection of Specific Immunoglobulin M (IgM) and IgA Antibodies in Serum and Saliva"; Clinical and Diagnostic Laboratory Immunology; Bearing a date of Mar. 2003; pp. 317-322; vol. 10, No. 2; American Society for Microbiology.

Barnes, Allan J., et al.; "Excretion of Methamphetamine and Amphetamine in Human Sweat Following Controlled Oral Methamphetamine Administration"; Clinical Chemistry; Bearing a date of 2008; pp. 172-180; vol. 54, No. 1; American Society for Clinical Chemistry.

Beck, M., et al.; "Nanoelectrochemical transducers for (bio-) chemical sensor applications fabricated by nanoimprint lithography"; Microelectronic Engineering; Bearing a date of 2004; pp. 837-842; vol. 73-74; Elsevier B.V.

Cramer, Joyce A., et al.; "Compliance With Medication Regimens for Mental and Physical Disorders"; Psychiatric Services; Bearing a date of Feb. 1998; pp. 196-201; vol. 49; American Psychiatric Association.

Davis, Mark D.P., et al.; "Thermoregulatory Sweat Testing in Patients With Erythromelalgia"; Archives of Dermatology; Bearing a date of Dec. 2006; pp. 1583-1588; vol. 142; American Medical Association; located at www.archdermatol.com.

Hemmingsson, Tryggve, et al.; "Novel Hand-Held Device for Exhaled Nitric Oxide-Analysis in Research and Clinical Applications"; Journal of Clinical Monitoring and Computing; Bearing a date of 2004; pp. 379-387; vol. 18; Springer 2005.

Huestis, Marilyn A., et al.; "Excretion of $\Delta^9$-Tetrahydrocannabinol in Sweat"; Forensic Science International; Bearing a date of Jan. 30, 2008; pp. 173-177 (pp. 1-10); vol. 174(2-3); National Institutes of Health.

Illigens, Ben M.W., et al.; "Sweat testing to evaluate autonomic function"; Clinical Autonomic Research; Bearing a date of Nov. 6, 2008; pp. 79-87; vol. 19.

Kintz, Pascal, et al.; "Sweat testing for heroin and metabolites in a heroin maintenance program"; Clinical Chemistry; Bearing a date of 1997; pp. 736-739; vol. 43, No. 5.

Knott, Christine, et al.; "Phenytoin-valproate interaction: importance of saliva monitoring in epilepsy"; British Medical Journal; Bearing a date of Jan. 2, 1982; pp. 13-16; vol. 284.

Kovacs, Eva M.R., et al.; "Effect of caffeinated drinks on substrate metabolism, caffeine excretion, and performance"; Journal of Applied Physiology; Bearing a date of 1998; pp. 709-715; vol. 85; American Physiological Society.

Lavrik, Nickolay V., et al.; "Cantilever transducers as a platform for chemical and biological sensors"; Review of Scientific Instruments; Bearing a date of Jul. 2004; pp. 2229-2253; vol. 75, No. 7; American Institute of Physics.

Mezzasoma, Letizia, et al.; "Antigen Microarrays for Serodiagnosis of Infectious Diseases"; Clinical Chemistry; Bearing a date of 2002; pp. 121-130; vol. 48, No. 1; American Association of Clinical Chemistry.

Mitchell, Alex J., et al.; "Why don't patients take their medicine? Reasons and solutions in psychiatry"; Advances in Psychiatric Treatment; Bearing a date of 2007; pp. 336-346; vol. 13.

Patel, Nilay; "Nintendo Wii Vitality Sensor detects your pulse"; Engadget; Bearing a date of Jun. 2, 2009; Printed on Jan. 8, 2010; pp. 1-24; located at: http://www.engadget.com/2009/06/02/nintendo-wii-vitality-sensor-detects-your-pulse/.

Phillips, Michael; "Sweat-Patch Test for Alcohol Consumption: Rapid Assay with an Electrochemical Detector"; Alcoholism: Clinical and Experimental Research; Bearing a date of Fall 1982; pp. 532-534; vol. 6, No. 4; The American Medical Society on Alcoholism, The Research Society on Alcoholism, and the National Council on Alcoholism.

Potyrailo, Radislav A., et al.; "Chemical Sensors Based on Micromachined Transducers with Integrated Piezoresistive Readout"; Analytical Chemistry; Bearing a date of Aug. 15, 2006; pp. 5633-5638; vol. 78, No. 16; American Chemical Society.

Robroeks, C.M.H.H.T., et al.; "Exhaled nitric oxide and biomarkers in exhaled breath condensate indicate the presence, severity and control of childhood asthma"; Clinical and Experimental Allergy; Bearing a date of 2007; pp. 1303-1311; vol. 37; Blackwell Publishing Ltd.

Schena, Mark, et al.; "Quantitative Monitoring of Gene Expression Patterns with a Complementary DNA Microarray"; Science; Bearing a date of Oct. 20, 1995; pp. 467-470; vol. 270.

Smith, Andrew D., et al.; "Use of Exhaled Nitric Oxide Measurements to Guide Treatment in Chronic Asthma"; The New England Journal of Medicine; Bearing a date of May 26, 2005; pp. 2163-2173; vol. 352, No. 21; Massachusetts Medical Society.

Tang, Dianping, et al.; "Magnetic Control of an Electrochemical Microfluidic Device with an Arrayed Immunosensor for Simultaneous Multiple Immunoassays"; Clinical Chemistry; Bearing a date of 2007; pp. 1323-1329; vol. 53, No. 7; American Association for Clinical Chemistry.

Thieme, Thomas, et al.; "Determination of Measles, Mumps, and Rubella Immunization Status Using Oral Fluid Samples"; JAMA; Bearing a date of Jul. 20, 1994; pp. 219-221; vol. 272, No. 3.

Uchida, Hideaki, et al.; "A New Assay Using Surface Plasmon Resonance (SPR) to Determine Binding of the *Lactobacillus acidophilus* Group to Human Colonic Mucin"; Bioscience, Biotechnology, and Biochemistry; Bearing a date of 2004; pp. 1004-1010; vol. 68, No. 5.

\* cited by examiner

FIG. 2
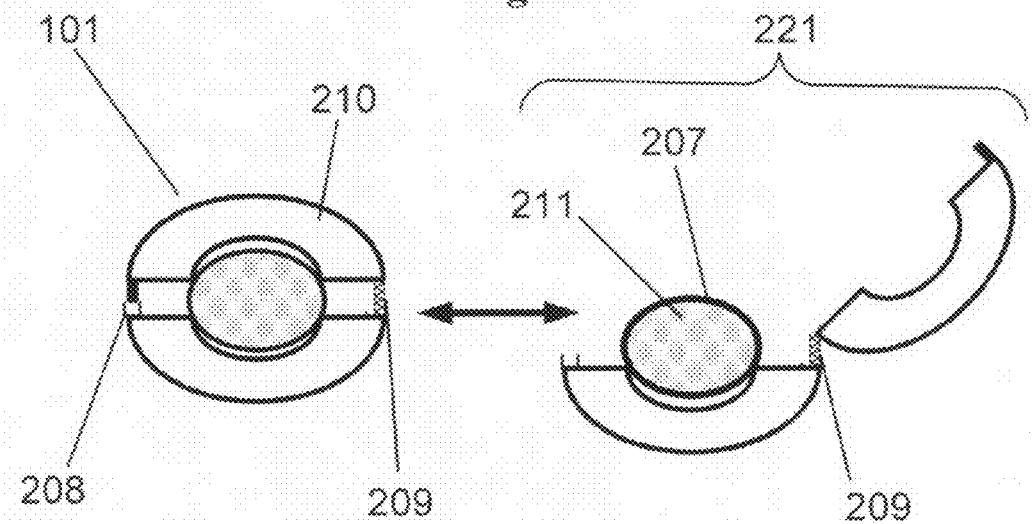
Fig. 2A
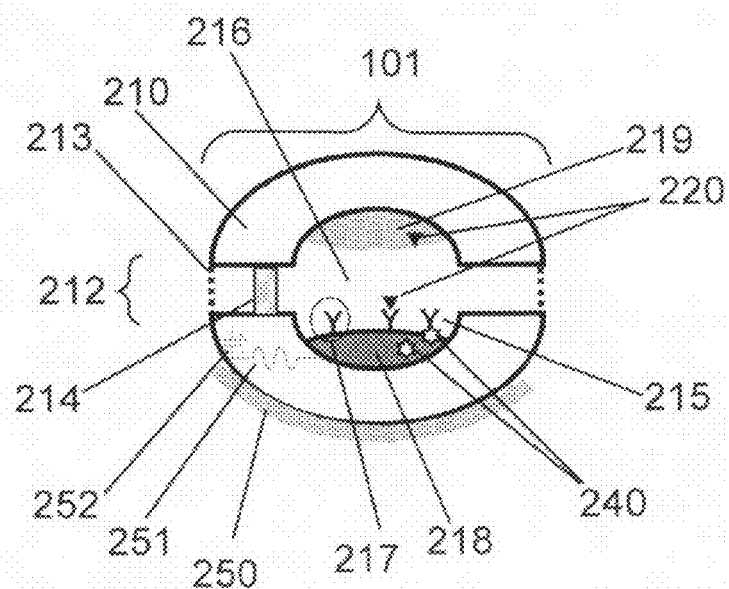
Fig. 2B

FIG. 3
Fig. 3A
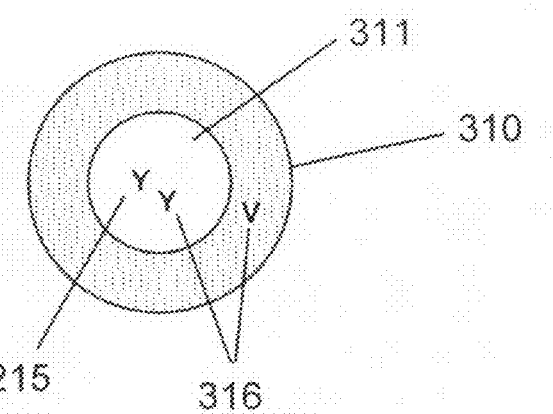
Fig. 3B
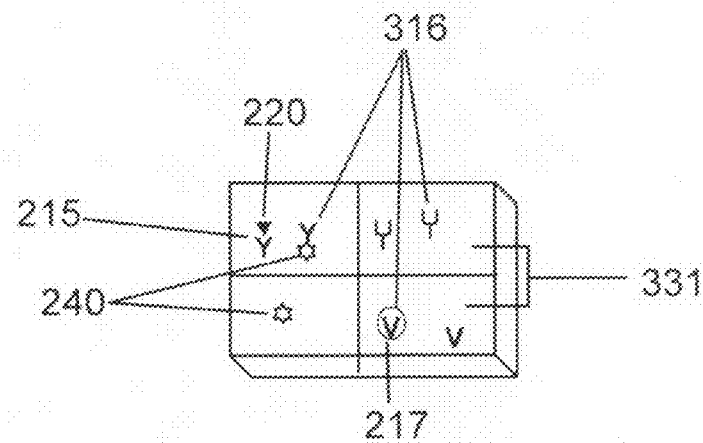
Fig. 3C
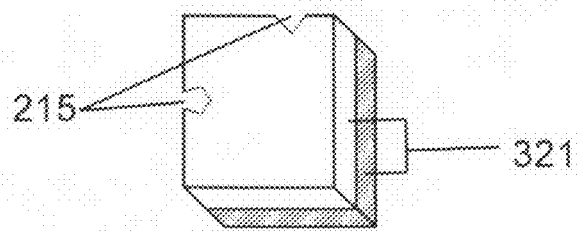

FIG. 17
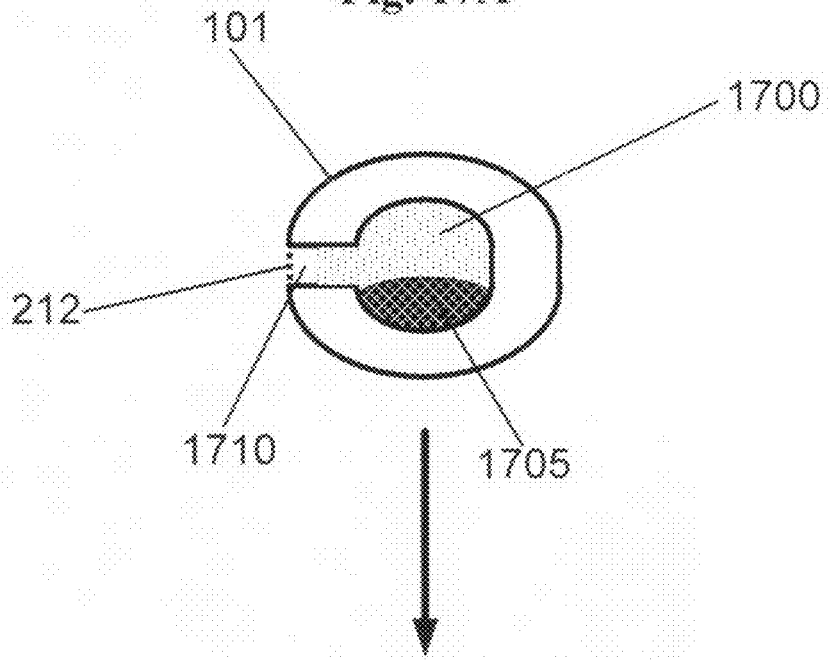
Fig. 17A
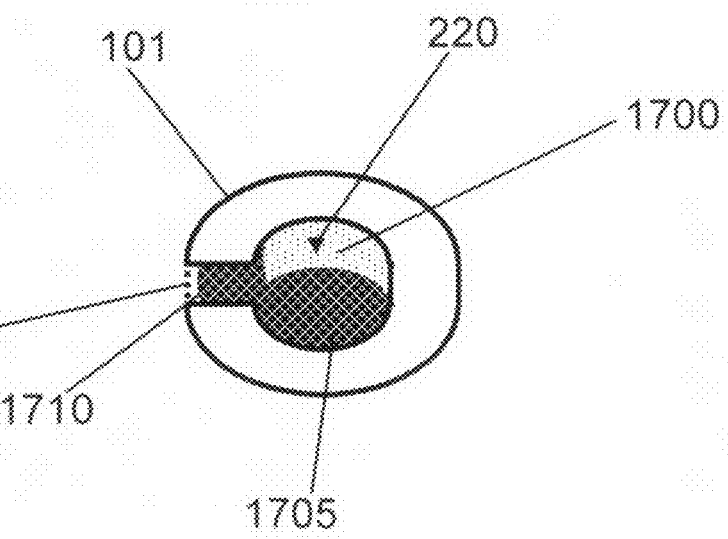
Fig. 17B

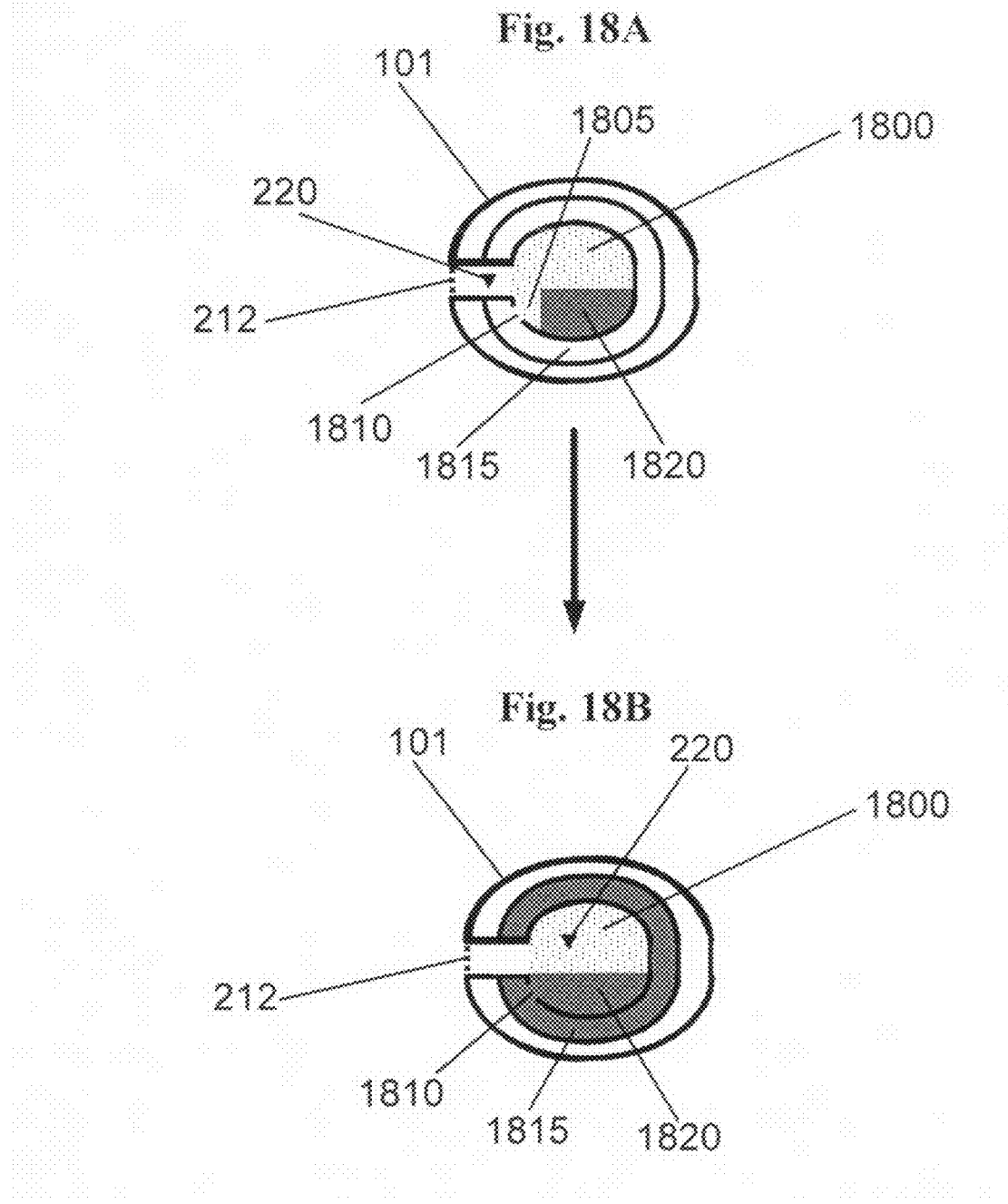

DEVICES AND METHODS FOR DETECTING AN ANALYTE IN SALIVARY FLUID

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications is incorporated herein by reference to the extent such subject matter is not inconsistent herewith.

RELATED APPLICATIONS

For purposes of the USPTO extra-statutory requirements, the present application constitutes a continuation-in-part of U.S. patent application Ser. No. 12/584,054, titled BEVERAGE IMMERSATE WITH DETECTION CAPABILITY, naming Leroy E. Hood, Edward K. Y. Jung, Elizabeth A. Sweeney, Clarence T. Tegreene, and Lowell L. Wood, Jr. as inventors, filed Aug. 28, 2009, which is currently co-pending, or is an application of which a currently co-pending application is titled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

SUMMARY

In one aspect, a system for detecting one or more analyte in salivary fluid includes but is not limited to a discrete oral component configured for complete enclosure in a human oral cavity, at least one sensor configured to detect one or more analyte in salivary fluid, and an external device including a port configured for communication with the at least one sensor. In addition to the foregoing, other system aspects are described in the claims, drawings, and text forming a part of the present disclosure.

In one aspect, a method for detecting one or more analyte in salivary fluid includes but is not limited to detecting one or more analyte within salivary fluid with at least one sensor integral to a discrete oral component, wherein the discrete oral component is configured to be completely enclosed in the oral cavity and includes one or more flavorant, and communicating information from the sensor to an external device. In one aspect, a method for providing health history for at least one individual includes sensing, with at least one sensor, one or more analyte in salivary fluid from an individual at a first time point, processing at least a subset of information from the at least one sensor into at least one first result, storing the at least one first result in memory, and indicating at least one first result to a system user. In addition to the foregoing, other method aspects are described in the claims, drawings, and text forming a part of the present disclosure.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

In addition to the foregoing, various other method and/or system and/or program product aspects are set forth and described in the teachings such as text (e.g., claims and/or detailed description) and/or drawings of the present disclosure.

The foregoing is a summary and thus may contain simplifications, generalizations, inclusions, and/or omissions of detail; consequently, it should be appreciated that the summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 2A is an illustrative view of a system.
FIG. 2B is an illustrative view of a system.
FIG. 3A is an illustrative view of a system.
FIG. 3B is an illustrative view of a system.
FIG. 3C is an illustrative view of a system.
FIG. 17A depicts a hydrogel forming a plug configured to block egress of a flavorant from a discrete oral component.
FIG. 17B illustrates a hydrogel plug in a retracted state, configured to allow egress of a flavorant from a discrete oral component.

FIG. 18A depicts a hydrogel forming a plug configured to block egress of a dye into a visualization region within a discrete oral component.

FIG. 18B illustrates a hydrogel plug in a retracted state, configured to allow egress of a dye into a visualization region within a discrete oral component.

DETAILED DESCRIPTION

Figure 1:
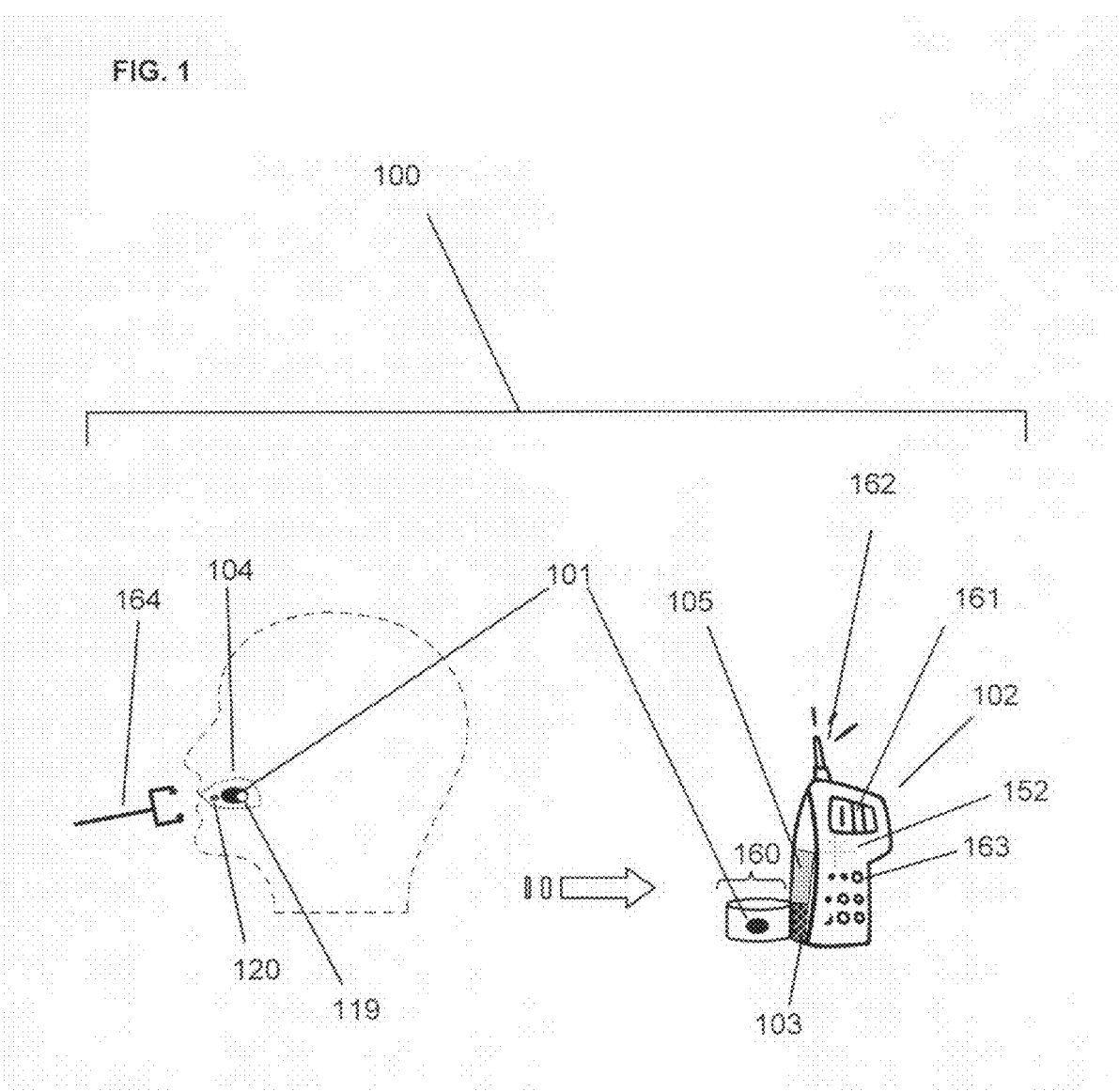
FIG. 1 is a schematic of a system.

Saliva and related fluids can provide a noninvasive source for biomarkers of systemic and local diseases and disorders. In addition to providing a copious supply of saliva, the mouth can act as an access point to the gut, respiratory, and circulatory systems. In some individuals, such as children and the infirm, saliva may be preferable to samples taken invasively. See, for example, European Patent Application Publication No. EP 1 397 997 A1 to Gröschl and Rauh titled "Detection device," and U.S. Pat. No. 6,022,326 to Tatum et al., titled "Device and method for automatic collection of whole saliva," which are herein incorporated by reference. Studies illustrate the numbers and varieties of analytes that are available for testing in salivary fluids. See, for example: Kaufman and Lamster, "The Diagnostic Applications of Saliva—A Review", *Crit Rev Oral Biol Med,* 13(2):197-212 (2002); Lawrence, "Salivary markers of systemic disease: noninvasive diagnosis of disease and monitoring of general health," *J. Can. Dent. Assoc.* 68(3): 170-174 (2002); Li et al., "The oral fluid MEMS/NEMS chip (OFMNC): diagnostic and translational applications," *Adv. Dent. Res.,* 18: 3-5 (2005); "Salivary diagnostics, the 'magic mirror' to your health . . . at your personal computer," *Science Daily*, Apr. 5, 2008; and Wong, "Salivary Diagnostics Powered by Nanotechnologies, Proteomics and Genomics,"*J Am Dent Assoc.,* 137:313-321 (2006) which are herein incorporated by reference. In addition to compounds associated with the mouth and mucous membranes, such as immunoglobulin A (IgA), other analytes can be present at detectable levels, including markers of disease, drugs and alcohol. For example, salivary fluid has been used as a medium for the detection of HIV antibodies. See Hodinka et al., "Minireview: Detection of Human Immunodeficiency Virus antibodies in oral fluids," *Clin. & Diagn. Lab Immun.,* 5(4): 419-426 (1998), and Nishanian et al., "Oral fluids as an alternative to serum for measurement of markers of immune activation," *Clin. & Diagn. Lab Immun.,* 5(4): 507-512 (1998), which are herein incorporated by reference. Markers related to systemic health have also been measured in salivary fluids as an alternative source to serum. Hormones, antibodies, electrolytes, and cholesterol are just a few of the analytes that can be monitored in salivary fluids. See, for example: Hofman, "Human saliva as a diagnostic specimen," *J. Nutr.,* 131: 1621S-1625S (2001); Wong, "Oral Fluid NanoSensor Test (OFNASET)" grant 5U01DE017790-03 grant abstract; Karjalainen et al., "Salivary cholesterol of healthy adults in relation to serum cholesterol concentration and oral health," *J. Dent. Res.* 76: 1637-1643 (1997); and Queyras and Carosi, "Non-invasive techniques for analyzing hormonal indicators of stress," *Ann Ist Super Sanita,* 40(2): 211-221 (2004), which are incorporated herein by reference. Studies have also shown that markers of environmental chemical exposure are detectable in salivary fluids. See for example, Bauer "Saliva spits out information on chemical exposure,"*Innovations Report*, Oct. 24, 2003, which is herein incorporated by reference. Some analytes in the salivary fluids arise from gingival crevicular fluids, transudates or exudates. In addition, the oral mucosa is highly vascularised, which has led to the use of transmucosal access to the circulatory system.

The oral cavity is also directly connected to the digestive tract. This has allowed testing for stomach disorders, including the presence of *Helicobacter pylori* (*H. pylori*), a causal agent in stomach ulcers. The DNA of *H. pylori* can be isolated from salivary fluids taken from infected individuals. Additionally, under the right conditions, urea released by the pathogen can be measured in oral gases (see, for example, "Urea breath test for *Helicobacter pylori* detection: present status," Pathak, Bhasin and Khanduja, *Trop Gastroenterol*. October-December; 25(4):156-61 (2004), which is herein incorporated by reference). Oral gases and condensates also provide a means of sampling lung exhalations to investigate pulmonary or systemic diseases. Nitric oxide, carbon monoxide, other volatile gases, as well as lipids, leukotrienes and eicosanoids are a few detectable markers of pulmonary diseases in oral samples (see, for example, "Exhaled Markers of Pulmonary Disease," Kharitonov and Barnes, *Am J Respir Crit Care Med,* 163: 1693-1722, (2001), which is herein incorporated by reference). Respiratory diseases continue to be a major cause of morbidity and mortality throughout the world. In 2003, asthma alone affected 20.7 million American adults, or 9.7% of the total adult population (see, for example, Tables 3 and 4 as well as Appendix III, table V in the Summary Health Statistics for U.S. adults: National Health Interview Survey, 2003, published by the CDC) and 9.1 million children (12%; see, for example, Table 1 in the Summary Health Statistics for U.S. Children: National Health Interview Survey, 2003.)

With reference now to FIG. 1, shown is an example of a system for detecting one or more analyte in salivary fluid that may serve as context for introducing one or more processes and/or devices described herein. The use of the same symbols in different drawings typically indicates similar or identical items. FIG. 1 shows an embodiment of a system 100 for detecting one or more analyte 120 in a bodily fluid such as saliva and related fluids, collectively referred to herein as "salivary fluid." Related fluids would include, for example, blood, breath condensate, oral gas, crevicular fluid, transudate, exudate, gingival crevicular fluid, mucosal transudate or exudate, ingested remnants and mucus, which are collectively referred to herein as "salivary fluid". See, for example, Vass et al., "Comparison of nasal and oral inhalation during exhaled breath condensate collection," *Am J Respir Crit Care Med* 167: 850-855 (2003), which is herein incorporated by reference.

The system 100 comprises a discrete oral component 101 that is of a size and shape able to be entirely enclosed in an oral cavity 104 without protrusion, an external device 102 that is configured to communicate with the discrete oral component 101, and one or more sensor configured to detect one or more analyte in salivary fluid 103, 119. The external device 102 may be configured to communicate directly with the discrete oral component 101. For example, the external device 102 may be configured to send signals to the discrete oral component 101 and receive signals from the discrete oral component 101. The external device 102 may be configured to communicate, for example, with the discrete oral component 101 via electronic circuitry integral to the discrete oral component 101. The external device 102 may be configured to communicate with the discrete oral component 101 indirectly. The external device 102 may be configured to communicate with at least one sensor 119 within the discrete oral component 101, such as via detection of electromagnetic radiation emitted from the sensor. For example, the external device 102 may be configured to detect sensor output from the discrete oral component 101, such as emitted light or vibration from a sensor 119 located within the discrete oral component 101. The external device 102 may be configured to communicate with one or more sensor 119 within the discrete oral component 101 directly. The external device may include a port configured for communication with the discrete oral component.

As shown in FIG. 1, in some embodiments there may be one or more sensor 119 integral to the discrete oral component 101. In addition or distinctly, there may be one or more sensor 103 integral to or operably attached to the external device 102. In some embodiments, there may be only one sensor or there may be a plurality of sensors. In embodiments in which the discrete oral component 101 includes a sensor 119, the external device 102 may include a detector configured to recognize the signal from the oral component 101 through a port 160, for instance a glass window, a receiver, or a gas port. A "sensor" as used herein, includes a unit that specifically identifies a substance, such as an analyte, and generates a signal that the identification has been made. A sensor may include a gas or chemical sensor, or an optical, acoustic, or electric sensor. A sensor may be an electrochemical sensor. A sensor may be a biological sensor. The signal generated by a sensor may be, for example, an electrical, visual, magnetic, acoustic, vibrational, heat, light (including infrared (IR) or ultraviolet (UV)), radio frequency (RF) or electromagnetic radiation signal.

The discrete oral component 101 may be manufactured in part or entirety from a substantially rigid material, for example a hard plastic or fibrous composite. The discrete oral component 101 may include at least one pliable material. The discrete oral component 101 may include, for example, at least one natural gum base, artificial gum base, acacia, carageenan, plastic, elastomeric polymer, polyisobutylene, or paraffin. For example, the discrete oral component 101 may include a pliable material that is configured to bend or reform due to physical pressure within an individual's oral cavity 104, such as from sucking or chewing activity. The discrete oral component 101 may include at least one component that is encapsulated, such as a component configured for timed release or durability during storage.

In some embodiments, the discrete oral component 101 may be manufactured in whole or in part from one or more gel or gel-like material such as a hydrogel, a hydrosol, a sol-gel, xerogel, an aerogel, a smart gel, a hydrocarbon gel, a ferrogel, a colloid, a superporous gel, a responsive gel, or other gel made from natural polymers, synthetic polymers, or a combination or composite thereof. The discrete oral component 101 may include a chewable, pliant substance, such as one containing, for example, a natural or synthetic gum base, such as those used in chewing gums, like acacia or carrageenan; or a paraffin wax, soft plastic, or an elastomeric polymer like polyisobutylene. The discrete oral component 101 may include at least one pliable material. The discrete oral component 101 may be any shape and size, and configured for complete enclosure in an oral cavity. In some embodiments, the discrete oral component is configured for complete enclosure in a human oral cavity. In some embodiments, the discrete oral component may be configured to allow for swallowing of the discrete oral component by an individual. A discrete oral component configured to allow for swallowing may, for example, be configured in a size and shape to minimize choking hazard or intestinal blockage in the case of ingestion. A discrete oral component configured to allow for swallowing may, for example, be manufactured from materials that are non-toxic, non-irritating, and stable when passed through an individual's gastrointestinal tract. A discrete oral component may be configured for recovery after passage through an individual's gastrointestinal tract, or it may be configured to be disposable and therefore intentionally not recovered.

Although a human user is depicted in FIG. 1, it is envisioned that the systems and methods described herein may be utilized with other animals, for example domesticated animals such as canines, felines, bovines, or equines. For example, the discrete oral component 101 depicted herein may be configured for enclosure in the oral cavity 104 of a domestic house cat and the system incorporated with a cat toy. For example, the discrete oral component 101 depicted herein may be configured for enclosure into the oral cavity 104 of a domestic dog and the system incorporated into a dog toy. In some embodiments, the discrete oral component may be configured as an animal toy configured to be chewed but not swallowed. In some embodiments the discrete oral component may be configured as an item that would not present a choking hazard if swallowed, and may be passed normally through the gastrointestinal system of the animal, and later recovered and/or disposed of. A discrete oral component configured for chewing and/or swallowing may be single-use and disposable after the single use. Systems and methods such as those described herein may be used to monitor the health and well-being of domestic animals, such as through analysis of stress hormones present in salivary fluids. See, for example, Queyras and Carosi, "Non-invasive techniques for analyzing hormonal indicators of stress," *Ann Ist Super Sanita,* 40(2): 211-221 (2004), which is incorporated herein by reference.

An analyte 120, 220 may include at least one biological marker, antibody, polypeptide, protein, complex, nucleic acid, cell, pathogen, lipid, alcohol, sterol, steroid, carbohydrate, metal, electrolyte, organic compound, nonorganic compound, organophosphate, drug, therapeutic, gas, or pollutant. The presence of one or more analyte may, alone or in combination, be an indicator of a physiologic state, a disease state like an active infection, or a metabolic state. The levels of one or more analyte or its presence at a particular time point may be an indicator of a physiologic state, a disease state like an active infection, or a metabolic state. For example, the presence of abnormal levels of pepsin activity may indicate the presence of gastroesophageal reflux disease (GERD), gastric reflux disease or acid reflux disease. See, for example, U.S. Pat. No. 7,402,423 to Taghizadeh, titled "Apparatus for detection of pepsin," which is hereby incorporated by reference. An analyte may include at least one metabolite. For example, an analyte may include a metabolic product generated by the physiology of the user. A metabolite may be indicative of a metabolic state, for example a metabolite may be indicative of a healthy state, a disease state, or a physiological state. For example, the presence of the analyte acetone may operate as an indicator of ketosis. See, for example, Musa-Veloso et al., "Breath acetone is a reliable indicator of ketosis in adults consuming ketogenic meals," *Am J Clin Nutr.* 76(1):65-70 (2002), and Khartinov and Barnes, "Exhaled Markers of Pulmonary Disease," *Am J Respir Crit Care Med,* 163:1693-1722 (2001), and U.S. Pat. No. 6,609,068 to Cranley et al., titled "Personal computer breath analyzer for health-related behavior modification and method," which are herein incorporated by reference. In some embodiments, the system may include at least one provided substance, such as a drug or compound configured to be metabolized by an individual user. A system wherein the analyte includes at least one metabolite may also include at least one provided substance, wherein the at least one metabolite includes at least one metabolite of the provided substance.

Depending on the embodiment, various possible types of sensors may be utilized within the discrete oral component 101 or in association with the external device 102. Multiple types of sensors are described herein as exemplary types, and others are known in the art. One or more sensor may include, for example, at least one optical sensor, acoustic sensor, electromagnetic sensor, magnetic sensor, electrophoretic sensor, electrochemical sensor, biochemical sensor, microfluidic sensor, magnetic resonance sensor, piezoelectric sensor, surface plasmon resonance sensor, optical microsensor array, surface enhanced raman spectrometer (SERS), laser, ion flow tube, metal oxide sensor (MOS), infrared spectrophotometer, acoustic wave sensor, colorimetric tube, conductive-polymer gas sensor, chemoresistor, selective resonance sensor, gas chromatograph, mass spectrophotometer, or magnetic resonance sensor. As an example of a hand-held tandem mass spectrophotometer that may be integrated into an external device, see Gao et al., "Design and characterization of a multisource hand-held tandem mass spectrophotometer," *Anal. Chem.* 80: 7198-7205 (2008), which is herein incorporated by reference. As an example of a gamma-beta radiation detector, see the Ion Ferret™ device available from Overhoff Technology Corporation (Milford Ohio), the 2009 brochure for which is herein incorporated by reference. As an example of a liquid scintillation counter sensor, see the Innovative Technology Summary Report titled "Lumi-scint Liquid Scintillation Counter," OST/TMS ID 2311, July 2001, which is herein incorporated by reference. As an example of a visible light, UV or IR sensor, see the MiScope® Handheld Digital Microscope, available from Forensics Source (Jacksonville Fla.). As an example of a carbon dioxide or carbon monoxide detector and thermometer, see the AQ2000 hand-held analyzer available from KIMO (France). A sensor may be optical and rely on frustrated total internal detection (FTIR) of magnetic particles, see Gelfand, "Device Offers a Roadside Dope Test," MIT Technology Review Online Edition Aug. 4, 2009, which is herein incorporated by reference.

In some embodiments, a sensor 119 is configured to be included within a discrete oral component 101. Depending on the embodiment, many possible types and configurations of the one or more sensor 119 integral to an oral component 102 may be utilized, including one or more array. Depending on the embodiment, a sensor may be utilized that is very small, such as a sensor or array that is configured to fit within the discrete oral component 101. In some embodiments, the sensor is a chemical sensor. See, for example, Snow et al., "Chemical Detection with a Single-Walled Carbon Nanotube Capacitor," *Science* 307:1942-1945 (2005), which is incorporated herein by reference. A sensor 119 incorporated within a discrete oral component 101 should be of a size and shape able to be configured for complete enclosure within the discrete oral component 101. Furthermore, a sensor 119 incorporated within a discrete oral component 101 should be operable at physiological temperatures and conditions of the oral cavity 104. Some types and configurations of sensors, therefore, are not suitable for inclusion within the discrete oral component 101. In embodiments wherein a sensor 119 is incorporated within a discrete oral component 101, an external device 102 may be configured to detect at least one signal from the sensor 119. For example, a port 160 for communication with the sensor 119 may include one or more devices for detection of a signal from the sensor 119.

In some embodiments, at least one sensor 103 is configured to be integral to an external device 102. Depending on the embodiment, many possible types and configurations of the one or more sensor 103 integral to an external device 102 may be utilized. In some embodiments, an external device 102 may be configured to be portable, such as a handheld or table-top device. In some embodiments, the external device 102 may be included in a larger fixture or device, such as a medical testing apparatus or machine. In some embodiments, the external device 102 may be coextensive with a device with other functionalities, such as a cell phone or personal digital assistant (PDA). A sensor 103 within an external device 102 may, therefore, be of various sizes, weights and configurations depending on the embodiment. In some embodiments an external device 102 may be configured to detect at least one signal from a sensor 103 integral to or operably attached to the external device 102.

An external device 102 may be configured to detect at least one signal from at least one sensor 119, 103. An external device 102 may be configured to send at least one signal to the discrete oral component 101. A signal may include, for example, light, color changes, sound, vibration, infrared (IR), radio, wireless or other detectable signals. A signal from an external device 102 may be part of the communication between the discrete oral component 101 and the external device 102. For example, an external device 102 and discrete oral component 101 may be integrated with a system to provide light signals such as described in International Patent Application No. WO 99/31560 to Mueller et al., titled "Digitally controlled illumination methods and systems" which is herein incorporated by reference. A signal from at least one sensor 119 may be part of the communication between the discrete oral component 101 and the external device 102. For example, where the sensor is configured to emit light after binding one or more analyte, an external device 102 may include a light detection device, such as a detection device configured to detect non-visible light or light of a specific wavelength. See, for example, US Patent Application No. 2003/0143580 to Straus, titled "Rapid and sensitive detection of molecules," which is herein incorporated by reference. In embodiments in which the discrete oral component 101 and/or an associated taggant is configured to emit optically-detectable signals, the port 160 may include in part or whole an optically-permeable section (e.g. a window), and the sensor 103 or detector may include at least in part a spectrophotometer and/or light source configured to elicit signals from the oral component or taggant. For example, the discrete oral component 101 or taggant may include at least one of a chromogen, fluorescent agent, luminescent agent, a quantum dot, or a compound configured to exhibit alterable optical density. A light source associated with a sensor, such as the sensor 103, may include, for example, a light emitting diode or a white light source, such as a source configured to provide light in a variable and/or specific wavelength, including infrared (IR) or ultraviolet (UV). See, for example, U.S. Pat. No. 5,183,740 to Ligler et al., titled "Flow immunosensor method and apparatus," U.S. Pat. No. 7,459,713 to Coates, titled "Integrated handheld sensing system approach for handheld spectral measurements having a disposable sample handling apparatus," US Patent Application No. 2008/0265146 to Coates, titled "Integrated sensing module for handheld spectral measurements," and WIPO Patent Application Publication No. WO 2007/113727 to Kolesny-Chenko et al., titled "A portable food and/or beverage analyzer and a method of analyzing a food and/or beverage in the field," which are herein incorporated by reference. For example, a light source may be configured to be a part of the detection of the opacity or colorimetric response of a component of the sensor. See, for example: U.S. Pat. No. 6,623,698 to Kuo, titled "Saliva-monitoring biosensor head toothbrush;" U.S. Pat. No. 7,314,453 to Kuo, titled "Handheld diagnostic device with renewable biosensor;" US Patent Application No. 2003/0023189 to Kuo, titled "Handheld diagnostic device with renewable biosensor;" and US Patent Application No. 2002/0127143 to Kuo, titled "Saliva-monitoring biosensor electrical toothbrush," which are herein incorporated by reference. In some embodiments, the external device 102 may use electric pulses to measure the conductivity of a sensor component. See, for example, U.S. Pat. Nos. 6,623,698 and 7,314,453 to Kuo, as above. In embodiments in which a taggant is a volatile compound or the analyte is in gaseous form, for example an oral or respiratory gas part of the salivary fluid, the sensor may include a gas sensor such as an acoustic wave, chemoresistant, or piezoelectric sensor, such as those described as part of an "electronic nose." See, for example, U.S. Pat. No. 5,571,401 to Lewis et al., titled "Sensor arrays for detecting analytes in fluids," and US Patent Application No. 2004/0006257 to Burch, titled "Detection, diagnosis, and monitoring of a medical condition or disease with artificial olfactometry," which are herein incorporated by reference.

Depending on the embodiment, other sensor types may include gas sensors, "electronic nose" sensors, "electronic tongue" sensors, nuclear magnetic resonance imagers, capillary electrophoretic devices, a volumetric sensor, or an optical sensor such as a spectrophotometer. See, for example: U.S. Pat. No. 5,303,585 to Lichte, titled "Fluid Volume Sensor;" Hagleitner et al., "Smart single-chip gas sensor microsystem," *Nature* 414:293-296 (2001); Yusa et al., "Controlled multiple quantum coherences of nuclear spins in a nanometer-scale device," *Nature* 434:1001-1005 (2005); U.S. Pat. No. 5,174,962 to Brennan titled "Apparatus for determining DNA sequences by mass spectrometry;" and Skelley et al., "Development and evaluation of a microdevice for amino acid biomarker detection and analysis on Mars," *Proc. Natl. Acad. Sci. USA,* 102(4):1041-1046 (2005), which are herein incorporated by reference. See, for example, Lavigne et al., "Solution-based analysis of multiple analytes by a sensor array: toward the development of an "electronic tongue," Journal of the American Chemical Society, 120: 6429-6430 (1998), which is herein incorporated by reference. Other examples of sensors may include technology such as optical microsensor arrays, surface enhanced raman spectroscopy (SERS), diode lasers, selected ion flow tubes, mass spectrometry, metal oxide sensors (MOS), infrared spectrometry, acoustic wave sensors, colorimetric tubes, infrared spectroscopy, conductive-polymer gas-sensors (chemoresistors), magnetic resonance, nanotechnology, and/or selective resonance techniques. See, for example, US Patent Application No. 2007/0021458 to Ishikawa et al., titled "Selective resonance of bodily agents," and Li et al., "The oral fluid MEMS/NEMS chip (OFMNC): diagnostic and translational applications," *Adv. Dent. Res.,* 18: 3-5 (2005), which are herein incorporated by reference.

A sensor may be configured to be directly responsive to at least one of the one or more analyte. For example, a cantilever-based sensor may directly respond to the presence of an analyte. Instead or in addition, a sensor may be configured to be indirectly responsive to at least one of the one or more analyte. For example, at least one sensor may be configured to be responsive to a metabolite of at least one of the one or more analyte. For example, at least one sensor may be configured to be responsive to at least one taggant. For example, at least one sensor may be configured to be responsive to a metabolic byproduct of an analyte.

A sensor may include a biosensor. For example, a sensor 103, 119 may include a biosensor, for example a cell-based biosensor. See, for example, Rider et al., "A B cell-based sensor for rapid identification of pathogens," *Science* 301: 213-215 (2003), which is herein incorporated by reference. A sensor 103, 119 may include a biosensor, for example a piezoelectric quartz crystal biosensor or a piezoresistive microcantilever. See, for example, Kumar, "Biosensors Based on Piezoelectric Crystal Detectors: Theory and Application," *JOM-e* 52(10) (2000), Tombelli et al "Piezoelectric biosensors: strategies for coupling nucleic acids to piezoelectric devices," *Methods.* 37(1):48-56 (2005), and Wee et al., "Novel electrical detection of label-free disease marker proteins using piezoresistive self-sensing micro-cantilevers," *Biosens Bioelectron.* 20(10):1932-1938 (2005), which are herein incorporated by reference.

As illustrated in FIG. 1, the discrete oral component 101 and external device 102 may be configured to communicate through a port 160 of the external device 102. For purposes of illustration, the port 160 is shown here as a cavity configured for physical contact with the discrete oral component 101, however other configurations of the port including a gas port, a window, or a receiver, as well as other forms of communication, including gas exchange or acoustic, radio, or wireless technology may be used in some embodiments. In some embodiments, one or more sensor 103 is configured as part of the external device 102, however, one or more sensor 103 may also, or instead, be configured as part of the discrete oral component 101. The external device 102 may include at least one communication device including a telecommunication device, a display screen, a speaker, a printer, or a data processor. The external device 102 may include digital memory. For example, the external device 102 may include digital memory that is configured to record received or sent signals, information regarding detected analytes, time, temperature or pH associated with the detection, or other data. The external device 102 may also include a user interface such as a display screen, touchpad, E-ink device, auditory signal generator, or other interface, for example a keyboard interface 163. The external device 102 may include one or more power source 152, for example one or more batteries, electrical connections with an external power source or one or more power-generating elements such as solar cells. The external device may include one or more power sources such as, for example, a battery, microbattery, solar energy converter, fuel cell, biofuel cell, or power cord. In some embodiments, wireless transmission may serve as a means to power the system, including the external device. See US Patent Application No. 2005/0143787 to Boveja titled "Method and system for providing electrical pulses for neuromodulation of vagus nerve(s), using rechargeable implanted pulse generator," which is herein incorporated by reference. One or more power sources may be rechargeable or replaceable. One or more power sources may be operably connected to any module of the external device, for example display elements, reporting elements, or communication elements. The external device 102 may also include at least one reporting device, for example visual display elements configured to indicate when an analyte has been detected. The external device 102 may include a telecommunication device 162, which may include an antenna or a cable to transmit and receive information from a network or external computer device, such as a healthcare system computing device or an individual user's personal data organizer. See, for example: US Patent Application No. 2004/0078219 to Kaylor et al., titled "Healthcare networks with biosensors;" US Patent Application No. 2004/0100376 to Lye et al., titled "Healthcare monitoring system;" and Lempert, "Digital house calls? Check your health at home," MSNBC Feb. 21, 2006; which are herein incorporated by reference. For example, the external device may be configured to communicate with a network, such as a network that contains at least one medical history, for example a medical history of the individual whose salivary fluid has been examined, or of a reference individual or group. A medical history may also be stored in digital memory in the external device and be available for reference or updating. The medical history may include, for example, genetic or genomic information, drug use history, allergies, medical diagnoses, or surgical history. The external device 102 may also include additional elements or instrumentation 105 as desired in a specific embodiment. For example, an external device may include digital memory, and be configured to store results or data from at least one oral component or sensor.

Referring to FIG. 1, in certain embodiments such as those in which the discrete oral component 101 includes a sampling device, the external device 102 could include the one or more sensor 103, in communication with the port 160, which could be configured to hold the entire discrete oral component 101 or a constituent thereof, such as a detecting element. The external device 102 could further include, in communication with the port 160 and one or more sensor 103, additional instrumentation 105 of one or more type able to process the oral component 101, a constituent thereof, or a sample contained therein; examples include a fluidic or microfluidic system and/or means of providing taggants. For example, where the analyte includes advanced glycation endproducts, the external device may be configured to treat salivary fluids with hypochloric acid and examine the treated material with NMR spectroscopy. See Yoon et al., "Characterisation of advanced glycation endproducts in saliva from patients with diabetes mellitus," *Biochem. Biophys Res Comm.*, 323: 377-381 (2004), which is herein incorporated by reference. Alternatively, the external device 102 might be of a size able to be held by a human hand, and the sensor 103 might be configured to be in communication with the discrete oral component 101, including embodiments wherein the discrete oral component 101 might be located in the oral cavity 104, through a port 160, for instance a window or a gas port of a type and configuration able to accept a volatile compound or other chemical.

An external device 102 may include at least one communication device, such as a reporting device 161 like a display screen, a speaker, or a printer, and may be configured for interaction with a system user through a keyboard interface 163. For example, a communication device may be configured to accept queries or directions from at least one system user. An external device 102 might comprise multiple modules, for instance a handheld module configured to communicate with a separate component. An external device 102 may include a telecommunication device, such as a telecommunication device configured to communicate with a network, such as an area, localized, and/or centralized network. A network may include one or more database, such as but not limited to one or more medical history, including a genomic history such as genetic or genomic test results, or family information. The external device may be configured as a portion of a network, which might include as a conductive medium part or all of the body. See, for example, U.S. Pat. No. 6,754,472 to Williams et al., titled "Method and apparatus for transmitting power and data using the human body," which is incorporated herein by reference. The external device may be configured as a portion of a network that is integrated with part or all of a building, such as in a domotic, for instance the MavHome under study at the University of Texas at Arlington. The external device may be integrated with a system to provide light signals such as described in International Patent Application No. WO 99/31560 to Mueller et al., titled "Digitally controlled illumination methods and systems" which is herein incorporated by reference. Other components of the system may include a digital processing unit, which may be programmable and may include memory. Other components of the system may include at least one data processor configured to implement logic such as comparison, sorting, reduction, and/or endpoint determination. The system may be configured with a data processor configured to collect and analyze multiple data points in a relative fashion, including either serially or in parallel.

The system 100 may also include an instrument 164 configured for placing and retrieving the oral component 101. The instrument 164 may be manufactured from any material suitable to an embodiment, such as plastic, composites, or metal. Such an instrument may have particular utility when the system is used for detecting one or more analyte from salivary fluid in domestic animals or individual humans of differing physical abilities, such as children or handicapped individuals. Additionally, any part or all components of the system 100 could be sterile and/or the system could include sterile packaging for at least a portion of the discrete oral component. For example, there may be one or more modules that may be swapped out, removed, or replaced and the newly incorporated components may include sterile packaging prior to incorporation. For example, there may be one or more modules that may be swapped out, removed, or replaced and the removed modules may be placed in sterile packaging prior to further analysis or disposal.

The discrete oral component 101 may be flavored. For example, the discrete oral component 101 may include at least one flavorant or flavoring agent such as those common to the food industry. For example, the discrete oral component may include at least one flavorant incorporating flavoring agents and a carbohydrate, gelatin or oil based compound. A flavorant may be a natural flavorant, such as the essential oil, oleoresin, essence or extractive, protein hydrolysate, distillate, or any product of roasting, heating or enzymolysis, which contains the flavoring constituents derived from a spice, fruit or fruit juice, vegetable or vegetable juice, edible yeast, herb, bark, bud, root, leaf or any other edible portions of a plant, meat, seafood, poultry, eggs, dairy products, or fermentation products thereof, whose primary function in food is flavoring rather than nutritional. A flavorant may include salts, sugars, artificial sweeteners, or flavor enhancers. For example, the discrete oral component 101 may be covered with a flavorant or flavoring agent. For example, the at least one flavorant or flavoring agent may be a carbohydrate, gelatin or oil based coating on the surface of the discrete oral component. For example, the at least one flavorant or flavoring agent may be coated, dried or glazed onto the exterior of the discrete oral component. In some embodiments, the flavorant may be initially located in an indentation, reservoir or internal region of the discrete oral component 101 that is configured to release the flavorant through mechanical force, such as an individual sucking or chewing on the discrete oral component. In some embodiments, the flavorant may be initially located in an indentation, reservoir or internal region of the discrete oral component that is configured to release the flavorant in response to a condition, such as a temperature or pH. In some embodiments, the flavorant may be initially located in an indentation, reservoir or internal region of the discrete oral component 101 that is configured to release the flavorant in response to a sensor. In some embodiments, the at least one flavorant is of a type expected to influence an individual, for example being configured to emit a pleasing flavor for a length of time predicted to be optimal for sensing of an analyte 120, configured to lose a pleasing flavor after a particular length of time or use, or configured to emit an unpleasant flavor after a particular length of time or use. In some embodiments, the flavorant may be targeted to one or more group of users, for example a flavorant with sour flavor may be desirable to encourage a sufficient quantity of salivary fluid in the oral cavity in individuals with characteristically dry mouths. Citric acid, for example, has been shown to stimulate salivary fluid expression or production. See U.S. Pat. No. 6,102,872 to Doneen et al., titled "Glucose detector and method," which is herein incorporated by reference. For example, a flavorant that tastes like candy, such as a bubble gum or cotton candy flavor, may be desirable for use with children. For example, a flavorant tasting like mint or spice flavor may be desirable for use with adults. For example, a flavorant tasting like meat, such as chicken or beef flavor, may be desirable for use with cats or dogs. In some embodiments, the at least one flavorant is configured to change chemical composition during contact with salivary fluid relative to at least one of time, duration of physical pressure, presence of a target material, or presence of an amount of a target material. For example, a flavorant may be configured with a limited quantity of flavoring agent and therefore configured to lose flavor after a finite length of time. For example, a flavorant may be configured with a limited quantity of a dissolvable flavoring agent, such as a sugary compound configured to dissolve after contact with a particular amount of salivary fluid in combination with the physical pressure of chewing or sucking. For example, the flavorant may bind to a target material in salivary fluid, thereby reducing the levels of unbound flavorant available for tasting and reducing the length of time that an individual may taste the flavorant. For example, a flavorant may be encapsulated with a carbohydrate substrate which is configured to dissolve after contact with sufficient salivary fluid. See, for example, U.S. Pat. No. 6,746,529 to Witteveen et al., titled "Stable, spray-dried composition in a carbohydrate substrate and process for obtaining said composition," which is herein incorporated by reference. A flavorant may be incorporated into an emulsion.

The discrete oral component 101 may include at least one signaling element. A signaling element may function to emit a signal after contact between the discrete oral component 101 and salivary fluid has occurred, for example to signal a system user that the system is operating. Depending on the embodiment, a system including a signaling element may be configured to signal contact with salivary fluid at a specific point. Depending on the embodiment, a system including a signaling element may be configured to signal lack of contact with salivary fluid, or insufficient contact, at a specific point. For example, at least one signaling element may be configured to signal contact with salivary fluid relative to at least one of time, presence of a target material, or presence of amount of a target material. A target material may include, for example, the substance detected by the sensor, or a reference or additional substance. For example, the target material may be water, and the signaling element may be configured to indicate that a fluid containing water has been detected. As salivary fluid would be expected to contain some portion of water, such a signaling element may function to indicate to a system user that the system has sufficient contact with salivary fluid for relevant function. For example, a system may include a signaling element and a timekeeping device operably attached to a fluid sensor and a signal emitter, so that a user would be alerted that fluid had or had not been detected during a preset period of time. For example, a signaling element may be operably attached to a sensor in a system configured to cause a signal to be generated when a substance is present or absent after a particular period of time. For example, a signaling element may be operably attached to a sensor in a system configured to cause a signal to be generated when the sensor has detected a quantity of the substance after a particular period of time. For example, the system may be configured to emit a signal from the signaling element when more than a threshold level of water has been detected in salivary fluid. Such a situation may occur, for example, when the discrete oral component system is not being implemented in a correct manner. For example, the substance may be a mucin, and the system may be configured to emit a signal from the signaling element when more than a threshold level of mucin has been detected in salivary fluid. Signaling elements may include, for example, electronic elements such as an acoustic wave generator, a vibration emitter or an electric light. For example, a signal emitter may beep, vibrate or flash light after the discrete oral component 101 has been in contact with salivary fluid for a preset period of time. Signaling elements may include, for example, electronic elements such as a small electric shock emitter, or a transmitter to send data to the external device 102. Signaling elements may include chemical elements such as chemical dyes, inks, chromogens, or fluorogens. See, for example, US Patent Application No. 2002/0044891 to Miller et al., titled "Food Quality Indicator Device," which is herein incorporated by reference. Signaling elements may include flavorants, such as a signaling element configured to emit a flavorant with an unpleasant flavor after a threshold quantity of a substance has been detected. For example, a signaling element may include at least one flavorant incorporated with an emulsion or encapsulant configured for release of the flavorant at a preset time or condition.

FIG. 2 illustrates aspects of the systems described herein. FIG. 2A shows an enlarged image of an embodiment of a discrete oral component 101. As depicted in FIG. 2, the discrete oral component may include a plurality of regions 221, such as units, modules or modular regions. Depending on the embodiment, a number of different configurations could be considered. In one configuration, the plurality of regions 221 includes an outer shell 210 configured for separation, and one or more internal modules 211. There are numerous configurations for separating units, for instance an outer shell 210 may be configured with a hinge 209 and may come together at a closure 208, which could include one or more fitted, screwed or magnetic latch of any size, shape and distribution appropriate to the embodiment, including encircling the shell. As part of the plurality of regions 221, an internal module 211 may include in part or entirety one or more matrix 218. A matrix 218 may be associated with and constricted by the internal cavity 216 or may be configured as a distinct modular unit that is removable from the shell 210. An internal module may include an outer covering 207, for example configured for retaining the structural integrity of the module during replacement of a modular unit. An outer covering 207 could include a selective medium such as a gas permeable membrane such as a polysiloxane.

The discrete oral component 101 or a portion thereof could be of a single or multiple use type. For example, the discrete oral component may include modular units that may be replaced or recharged after use while other modular units may be durable and configured for multiple use. For example, as illustrated in FIG. 2, a discrete oral component 101 may include an outer shell 210 made from a durable plastic, metal, or fibrous material that is configured for use multiple times, while one or more internal modules may be replaced as they become spent, depleted, full, or to alter the modality of the discrete oral component 101. For example, modules including different types of flavorants may be switched into or out of the discrete oral component for particular applications. For example, modules including one or more colorant or dye may be switched in and out, such as to replace a spent or depleted module or to replace a module of a color or dye with one containing a different color or dye. For example, modules including one or more gum-type material for the oral release of flavorants, medicinals or nutritional elements may be incorporated. See SPI Pharma Newsletter *Special Delivery* "New formulation makes gum delivery system efficient and affordable," Summer 2001, which is herein incorporated by reference. Such modules may dissolve in whole or part during each use of the discrete oral component 101 and require replacement for every use. For example, an external flavorant coating may be reapplied or refreshed on the outer surface of the discrete oral component 101 between uses, such as a flavorant included in a coating 250. Modules may be configured for exchange as needed for detection of a different analyte. For example, a modular sensor with certain detection capabilities may be replaced with a modular sensor having the same or other detection capabilities. For example, a modular matrix containing a particular recognition element may be replaced with a new modular matrix containing the same recognition element or a different recognition element.

In some embodiments, the discrete oral component 101 might include one or more minimally or non-invasive means of enhancing transfer across the mucosa, of transudate, exudate or components thereof, such as proteins, peptides, glucose, or other analytes. For example, the discrete oral component 101 may include a transmucosal sampling mechanism. In one example, one or more chemical permeation enhancer such as isopropyl myristate, bile salts, surfactants, fatty acids and derivatives, chelators, cyclodextrins or chitosan might be included in a coating 250 of the discrete oral component 101. For example, see Murthy et al., "Physical and Chemical Permeation Enhancers in Transdermal Delivery of Terbutaline Sulphate," *AAPS PharmSciTech.* 2(1), Technical Note 1, (2001) and Senel and Hincal, "Drug permeation enhancement via buccal route: possibilities and limitations," *J Control Release* 72: 133-144 (2001), which are herein incorporated by reference. For example, a discrete oral component 101 might include an ultrasonic component in an outer shell or in an outer layer of the oral component. See, for example, US Patent Application No. 2004/0162467 to Cook, titled "Non-invasive transudate extraction," which is herein incorporated by reference. As an example, an oral component may be configured to include microprotrusions such as microneedles or microfine lances in an outer shell 210 or outer layer. See, for example, U.S. Pat. No. 6,953,589 to Trautman et al., titled "Device for enhancing transdermal agent flux," which is herein incorporated by reference. Other technologies that might be useful in such embodiments include, but are not limited to, iontophoresis, microdialysis, ultrafiltration, magnetic, electromagnetic, osmotic, electroosmosis, sonophoresis, microdialysis, suction, electroporation, thermal poration, microporation, microfine cannulas, skin permeabilization, or a laser. See, for example, Garrison et al., "A review of membrane sampling from biological tissues with applications in pharmacokinetics, metabolism and pharmacodynamics," *European Journal of Pharmaceutical Sciences,* 17: 1-12 (2002), which is herein incorporated by reference.

In some embodiments, the discrete oral component 101 includes one or more regions including at least one sampling region or module for salivary fluid or constituents thereof, including for a specific substance, including at least one analyte. As depicted in FIG. 2B, a discrete oral component 101 may include at least one internal cavity 216, which may include one or more reservoir. A reservoir may be configured to release a material, such as a flavorant, provided substance, taggant or hydration agent. For example, a discrete oral component 101 may include at least one reservoir configured to release at least one medicinal agent. A medicinal agent may include at least one expectorant, bronchodilator, cough suppressant, vasodilator, analgesic; antiseptic, anti-infective, antibiotic, nutritional supplement, therapeutic, enzymatic substrate, diagnostic challenge, methacholine, sensitizer, or taggant.

As depicted in FIG. 2B, a discrete oral component 101 may include a selective medium configured to allow at least one substance 220 from salivary fluid to enter or permeate into at least one region of the discrete oral component such as an internal cavity 216. As illustrated in FIG. 2B, a plurality of regions 221 could include at least one permeable area 212. For purposes of illustration, a permeable area 212 is shown as a single relatively small area, but depending on the embodiment, one or more permeable areas could be of any size and distribution, including distributed across the entire or a substantial portion of the surface of the discrete oral component. The permeable area 212 could include a covering 213, which might be a screen, possibly including a porous version of the same material as the shell 210. The permeable area 212 could include a selective medium 214 of a type configured to filter out, for example, debris, cells, molecules of a range of sizes, charged molecules or any other undesirable material, even excess moisture, while being configured to allow some other substances to pass through. Such a selective medium 214 could be made from any of a number of materials including charcoal or cellulose; a synthetic polymer such as but not limited to polyethylene, polycarbonate, nylon, polyester, polysiloxane, or polypropylene; or a hydrogel, or a monolayer or bilayer of lipids, and a selective medium could include a protein. Selective medium may include at least one of charcoal, cellulose, synthetic polymer, polyethylene, polycarbonate, nylon, polyester, polypropylene, polysiloxane, gel, hydrogel, lipid, and protein. For example, the selective medium 214 could be one made of cellulose configured with pores sized to allow diffusion of certain sized molecules, a hydrogel film of a type that swells at a certain pH, a gas-permeable membrane or a hydrophobic lipid bilayer. See, for example, "A hydrogel-based CO2 sensor," Herber and Olthuis, MESA+ Institute for Nanotechnology, University of Twente, which is incorporated herein by reference. For example, the selective medium 214 may include biocompatible membranes such as those described in U.S. Pat. No. 6,258,870 to Hubbell et al., titled "Gels for encapsulation of biological materials," which is herein incorporated by reference. The selective medium 214 could also or instead include one or more active transporter, such as a porin or ion transporter.

A discrete oral component 101 may be configured to recognize one or more substance. For example, a sensor integral to the discrete oral component 101 may be configured to detect a substance which is an analyte. For example, a sensor integral to the discrete oral component 101 may be configured to detect a substance which is a metabolite of the analyte. For example, a sensor integral to the discrete oral component 101 may be configured to detect a substance which is a taggant. For example, a signaling element may be configured to detect a substance such as water, a blood protein, taggant or metabolite. For example, a selective permeable layer may include at least one selective medium configured to recognize and select substances to retain and to exclude from diffusion or active transport through the selective medium 214. For example, the oral component may include at least one matrix configured for specific recognition and binding, with possible retention, of a substance. A substance may be an analyte itself, or an indicator of the presence of an analyte, for instance a metabolite of an analyte. A substance might be a biologic marker, a secreted marker, a cell, a pathogen, an antibody, a polypeptide, a protein, a complex, a nucleic acid, a lipid, an alcohol, a steroid, a carbohydrate, a metal, an electrolyte, an organic compound, an organophosphate, a drug, a therapeutic, a medicine, a gas, or a pollutant; a substance might also or instead be a metabolite, for example of a provided substrate or of the analyte. The substance may include one or more secreted markers. The substance may include at least one metabolite. In some embodiments, at least one of the one or more substance and at least one of the one or more analyte are the same.

One or more modular units 211 of the discrete oral component 101 may be configured to passively collect salivary fluids and/or constituents thereof, including cells or other biologics, within a matrix 218 in an internal cavity 216. In some embodiments, the discrete oral component 101 may include a passive sampling container, and one or more gel or gel-like materials could include an absorbent made from one or more material like those mentioned herein, which may be dehydrated in its initial state prior to contact with salivary fluid. A discrete oral component 101 may include at least one material from the list including absorbent, adsorbent, proteoglycan, charged polymer, polylysine, silica gel, alumina gel, and ion exchange resin. The matrix 218 might include an absorbent, like cotton, cellulose, natural or artificial sponge. The matrix 218 might include one or more gel, like a hydrogel, a hydrosol, a sol-gel, a xerogel, an aerogel, a hydrocarbon gel, a natural polymer gel, a synthetic polymer gel, a ferrogel, a colloid, a responsive gel, a superporous hydrogel or microparticle gel. A matrix 218 may be in a dehydrated form prior to contact with salivary fluid. Many types of porous hydrogels may be utilized, such as those used in the wound dressing described in U.S. Pat. No. 6,372,248, to Qin et al, titled "Dehydrated Hydrogels," which is incorporated herein by reference. An internal cavity 216 might include, possibly as a coating 219 on the surface of the internal cavity 216, a synthetic or natural adsorbent material of a type that promotes the adhesion of one or more constituent in the salivary fluids, like a cell or a protein. For example, an oral component may include a proteoglycan or a charged polymer such as polylysine. Other retaining materials could be included, such as semi-specific or non-specific adsorbents, such a silica ($SiO_2$) or alumina ($Al_2O_3$)—containing gel or an ion exchange resin, including as part of the matrix 218.

One or more modular units 211 of the discrete oral component 101 may be configured to store compounds within a matrix 218, which may be located within an internal cavity 216. For example, the matrix 218 may store a compound configured to be released. For example, the matrix 218 may be configured to store a recognition element 215. A matrix 218 may include at least one of a carbohydrate, alginate, protein, protein cage, lipid, phospholipid, liposome, cerasome, oil, emulsion, polymer, spheres, microspheres, or nanospheres. See US Patent Applications Nos. 2004/0115132, 2006/0204444 and 2007/0059245 to Young et al., titled "Protein cages for the delivery of medical imaging and therapeutic agents," and US Patent Application No. 2006/0292174 to de los Rios and Oh titled "Self-assembling nanoparticle drug delivery system," which are herein incorporated by reference. A discrete oral component 101 may include a hydrogel including hybrid materials, for example a hydrogel containing a hybrid protein-polysaccharide material. See U.S. Pat. No. 6,821,331 to Damodaran, titled "Protein-polysaccharide hybrid hydrogels," which is herein incorporated by reference.

The matrix 218 may be fabricated from any number of materials or composites as appropriate to an embodiment, such as, but not limited to, a natural gel like agarose, a natural and/or synthetic polymer gel, hydrogel, or colloid, and may include a gum base such as an acacia gum. See, for example, U.S. Pat. No. 7,022,514 to Vodyanoy et al., titled "Use of acacia gum to isolate and preserve biological material," and US Patent Application No. 2003/0138939 A1 to Vodyanoy et al., titled "Use of acacia gum to isolate and preserve biological material," which are incorporated herein by reference. A matrix 218 may, instead or in addition, be a lipid monolayer or bilayer, as in a micelle or liposome, and may be anchored to a shell 210 region through a nonorganic tether. See, for example, "Design of Supported Membranes Tethered via Metal-Affinity Ligand-Receptor Pairs," Rädler et al., *Biophysical Journal* 79:3144-3152 (2000), which is herein incorporated by reference. A matrix 218 may be configured as one or more film or layer. A matrix 218 may include at least one of a hydrogel, hydrosol, sol-gel, hydrocarbon gel, natural polymer gel, synthetic polymer gel, lipid, colloid, encapsulation or emulsion. A matrix 218 may be configured as a plurality of spheres, such as micro- or nano-spheres. Such spheres might include protein cages, liposomes, synthetic hybrid cerasomes, microspheres or nanospheres of one or more natural and/or synthetic polymer, including dendrimers. See, for example, Katagiri et al. "Creation of asymmetric bilayer membrane on monodispersed colloidal silica particles," *Colloids Surf B Biointerface,* 38(3-4):149-53 (2004), which is incorporated herein by reference. For example, a matrix 218 may include at least one ligand affinity resin with or without a conjugated peptide or antibody such as those that are commonly used in chromatography and purification. For example a matrix 218 may include at least one ionophore as the recognition element presented on microspheres within the matrix. See, for example, U.S. Pat. No. 7,247,489 to Bakker, titled "Ion detecting microspheres and methods of use thereof," which is incorporated herein by reference. For example, distinctly from a recognition element configured as a separate agent, a recognition element may be a recognition site molecularly imprinted within a matrix itself or a part thereof, such as a molecular mimetic. See, for example: U.S. Pat. No. 6,670,427 to Ulbricht et al., titled "Template-textured materials, methods for the production and use thereof;" Ye et al., "Molecularly imprinted polymers as antibody and receptor mimics for assays, sensors and drug discovery;" *Anal Bioanal Chem.* 378(8):1887-1897 (2004); and Peppas et al., "Polymers and gels as molecular recognition agents," *Pharm Res.* 19(5):578-587 (2002), which are incorporated herein by reference.

The matrix 218 may include one or more flavoring agent, which may be included with an emulsion or encapsulation. Alternatively or in addition, one or more flavorant may be included in the oral component 101 within an emulsion or encapsulation 217, as a coating 250 and/or incorporated within the material forming the discrete oral component 101. A flavorant may be of a type designed to influence the user, for example a pleasant flavor that would encourage its use. The flavoring may be of a type responsive to a condition, such as time passed or the presence of a target material. Time-dependent flavorants are well-known in the food and candy industries. Multiple emulsions and encapsulations with differing properties as well as double emulsions are capable of enhanced responsiveness and may be included. See, for example, Utada et al., "Monodisperse Double Emulsions Generated from a Microcapillary Device," Science 308:537-541 (2005), which is herein incorporated by reference. The one or more flavorant might be configured for responsiveness, such as to volume of fluid or substance 220 collected. For instance, flavorant may be released through passive displacement or flavorant may be released through the operation of a more active element, such as release from a substance-responsive gel.

A discrete oral component 101 may include at least one compound configured to be physiologically incorporated into the body of a user, and may be configured to retain the at least one compound until a predetermined condition. For example, a discrete oral component may include at least one compound configured to be physiologically incorporated into the body of a user within at least one matrix 218. For example, a discrete oral component may include at least one compound configured to be physiologically incorporated into the body of a user within a coating such as an emulsion or encapsulation. For example, a matrix may be configured to retain a taggant or medicinal agent until the oral component is contacted with salivary fluid. For example, a matrix or a coating may be configured to retain a provided substance until the oral component has been in contact with salivary fluid for a preset period of time, such as the time required to dissolve an emulsion or encapsulation layer. See, for example, U.S. Pat. No. 6,746,529 to Witteveen et al., titled "Stable, spray-dried composition in a carbohydrate substrate and process for obtaining said composition," which is herein incorporated by reference.

An oral component 101 may include one or more recognition element 215 configured to recognize a substance 220. One or more recognition element 215 may be immobilized or otherwise embedded in the discrete oral component 101, such as within one or more internal cavity 216. In some embodiments, a recognition element 215 may specifically bind a substance 220. In some embodiments, a recognition element 215 may chemically recognize one or more substance. For example, a recognition element may include a peptide chain such as described in U.S. Pat. No. 7,402,423 to Taghizadeh, titled "Apparatus for the detection of pepsin," which is herein incorporated by reference. A recognition element 215 may, for example, be in solution within or immobilized on a surface of an internal module 211. A recognition element 215 may include, for example, at least one cell, protein, polypeptide, nucleic acid, oligonucleotide, carbohydrate, lipid, conjugate, synthetic molecule, or mimetic. A recognition element 215 may be in a matrix 218, for instance conjugated to a matrix of agarose beads, or embedded or encapsulated within a matrix structure. A recognition element 215 might itself be a biologic, for example: a *staphylococcus* protein A complex, which generally binds immunoglobulins; a binding peptide or protein like an immunoglobulin; a DNA binding protein; a genetically engineered protein; a nucleic acid; an aptamer; a carbohydrate; a lipid; a conjugate; or a synthetic molecule like an artificial antibody or other mimetic. See, for example, U.S. Pat. No. 6,255,461 to Mosbach et al., titled "Artificial antibodies to corticosteroids prepared by molecular imprinting," U.S. Pat. No. 5,804,563 to Still et al., titled "Synthetic receptors, libraries and uses thereof," U.S. Pat. No. 6,797,522 to Still et al. titled "Synthetic receptors," U.S. Pat. No. 5,831,012 to Nilsson et al., titled "Bacterial receptor structures" and US Patent Application No. 2004/0018508 to Friedman, titled "Surrogate antibodies and methods of preparation and use thereof," which are incorporated here by reference. A recognition element 215 may include an antibody, such as an antibody saturated with a labeled form of the target, as described in U.S. Pat. No. 5,183,740 to Ligler et al., titled "Flow immunosensor method and apparatus," which is herein incorporated by reference. In embodiments where glucose is an analyte to be optically detected by the external device, the recognition element may be a malachite green acceptor covalently linked to insulin. See, for example, Tolosa et al., "Lifetime-based sensing of glucose using energy transfer with a long lifetime donor," *Analytical Biochemistry* 250: 102-108 (1997), which is herein incorporated by reference.

In certain embodiments, a recognition element 215 might be encapsulated in one or more emulsion or other encapsulating material 217 instead of or in addition to distribution throughout the discrete oral component 101 or within its internal cavity 216 and/or in the matrix 218 as illustrated in FIG. 2. Proteins, for instance, have been shown to maintain their function when encapsulated. For more information regarding encapsulation of proteins, see, for example: "Fluorescence detection of enzymatic activity within a liposome based nano-biosensor," Vamvakaki et al., *Biosens Bioelectron.* 21:384-8 (2005); Sotiropoulou, et al., "Stabilization of enzymes in nanoporous materials for biosensor applications," *Biosens Bioelectron* 20:1674-1679 (2005); Besanger, et al., "Screening of inhibitors using enzymes entrapped in sol-gel-derived materials," *Anal. Chem.* 75, 2382-2391, (2003), which are herein incorporated by reference. Emulsions and encapsulating materials can, for example, include one or more carbohydrate, alginate, protein, protein cage, lipid, phospholipid, liposome, cerasome, oil, emulsion, or a polymer. Encapsulating materials may include photopolymerized water-soluble molecules, such as those described in U.S. Pat. No. 6,258,870 to Hubbell et al., titled "Gels for encapsulation of biological materials," which is herein incorporated by reference.

In certain embodiments, the system 100 may include one or more biosensor. A biosensor may be incorporated within the external device 102 or the discrete oral component 101. For instance a biosensor could be included within the internal cavity 216 and/or be incorporated in the matrix 218 of the discrete oral component 101. As used herein, "biosensor" refers to a sensor including at least one biological agent or component. A biosensor may include cells, proteins, peptides, nucleic acids, aptamers, lipids, or carbohydrates. The biosensor might comprise in part a recognition element 215 such as a cell, a protein, a nucleic acid, an aptamer, a lipid, and/or a carbohydrate, configured to transmit a signal when a substance is detected. For example, a recognition element 215 may include one or more genetically engineered cells, which may be configured within solution or immobilized in alginate within the matrix 218. Such genetically engineered cells may be configured to detect a substance through a receptor and then to produce a bioluminescent signal. See, for example, Daunert et al., "Genetically Engineered Whole-Cell Sensing Systems: Coupling Biological Recognition with Reporter Genes," *Chem. Rev.* 100(7): 2705-2738 (2000), which is herein incorporated by reference. As another example, the recognition element 215 may include an encapsulated enzyme configured to recognize the substance 220 as a substrate wherein the encapsulated enzyme is conjugated or otherwise associated with a responsive fluorescent compound. See, for example, Vamvakaki et al., "Florescence detection of enzymatic activity within a liposome based nano-biosensor," *Biosensors and Bioelectronics* 21: 384-388 (2005), and Sotiropoulou, et al., "Stabilization of enzymes in nanoporous materials for biosensor applications," *Biosensors and Bioelectronics* 20:1674-1679 (2005), and Besanger, et al., "Screening of inhibitors using enzymes entrapped in sol-gel-derived materials," *Anal. Chem.* 75:2382-2391 (2003), which are herein incorporated by reference. As another example, one or more component of a biosensor may be a biologically active molecule bound to a surface, for example using gold binding fusion proteins. See, for example, the product description from BioHesion™ titled "Advanced Surface Binding Technology," which is herein incorporated by reference. For example, a biosensor may include a bacterial protein. See "Scientists develop biosensor to detect *E. Coli* bacteria," *RxPG News*, Aug. 19, 2006, which is herein incorporated by reference.

In some embodiments, the system 100 may include at least one taggant. For example, the oral component 101 may include one or more taggant 240. For example the oral component 101 may include one or more taggant 240 as part of the matrix 218. A taggant 240 may be configured to be responsive to a recognition element 215, such as a taggant 240 configured to be released when an analyte 220 binds to a recognition element 215. A taggant, as used herein, includes a chemical or physical component which is configured to be detectable, such as through direct visual or olfactory detection by a user, or detection through a device or assay. In some embodiments, a taggant 240 may be included in a matrix structure or retaining materials of an oral component. In some embodiments, a discrete oral component 101 may be configured to store a taggant 240 at a distance from a matrix 218. A taggant storage region may be configured to release a taggant at a specific time or in response to a condition, such as physical pressure, temperature, pH or hydration. For example, a taggant may be released through flexing of a support surface configured to be responsive to binding of a substance to recognition elements. See, for example, Boisen et al., "Rapid molecular detection of food- and water-bourne diseases," *Microbiology Today*, August 2007, 116-118, which is herein incorporated by reference. Numerous types of taggants exist and various configurations may be utilized. A taggant 240 can include a dye, chromogen, a fluorescent substance, a luminescent substance, an odorant, a protein, a nucleic acid like an aptamer, a carbohydrate, a lipid, a synthetic molecule, a quantum dot, an optically active compound, a magnetic compound, a genetically engineered protein, a molecule configured for release, a resonance energy transfer molecule, a metal, a mass-label molecule, a radioisotope, or a volatile compound. For example, see US Patent Application No. 2003/0022225 to Monforte et al., titled "Releasable nonvolatile mass label molecules," U.S. Pat. No. 6,635,452 to Monforte et al. titled "Releasable nonvolatile mass label molecules," U.S. Pat. Nos. 5,516,931, 5,604,104 and 5,602,273 to Giese et al., titled "Release tag compounds producing ketone signal groups," U.S. Pat. No. 5,360,819 to Giese titled "Molecular analytical release tags and their use in chemical analysis," and U.S. Pat. No. 6,491,643 to Katzman and Carlebach, titled "Breath test analyzer," which are herein incorporated by reference. A taggant 240 may be included in a matrix 218 and released when a substance binds, such as in a displacement assay. The taggant 240 may be dehydrated prior to use, including dehydrated in complex with a recognition element 215. See, for example, U.S. Pat. No. 5,354,654 to Ligler et al., titled "Lyophilized ligand-receptor complexes for assays and sensors," which is herein incorporated by reference. The taggant 240 might be a passive label for the substance 220, such as a nonspecific dye like a cyanine dye, configured to bind to nucleic acids. Instead of or in addition, the taggant 240 may be configured to be responsive to binding of the substance 220, for example a labeled recognition element 215 like a fluorescein-conjugated antibody able to complex with the substance 220, or a recognition element 215 like a transferase that is configured to include a recognition site for the substance 220 and is configured to transfer the taggant 240 as a labeled modifier like a phosphate or carbohydrate group. See, for example, US Patent Application No. 2003/0022225 to Monforte et al., titled "Releasable nonvolatile mass label molecules," and U.S. Pat. No. 6,635,452 to Monforte et al. titled "Releasable nonvolatile mass label molecules," which are herein incorporated by reference. If the substance 220 or the recognition element 215 includes a catalyst or enzyme, the taggant 240 may also include a substrate with a taggant configured to be cleavable or activatable. Another example would include a recognition element 215 configured to exhibit altered conformation upon binding the substance 220, such as a calcium-dependent binding molecule like calmodulin, possibly as part of a fusion protein, and/or configured to allow resonance transfer. See, for example, Miyawaki et al., "Fluorescent indicators for $Ca^{2+}$ based on green fluorescent proteins and calmodulin," *Nature* 388: 882-887 (1997), which is incorporated herein by reference. The taggant 240 might also be incorporated in or intrinsically part of one or more material forming the matrix 218 or the oral component 101, and responsive to binding of the substance 220, such as a stimuli-responsive gel.

In some embodiments, the recognition element 215 may include a releasable taggant compound. Many types of releasable compounds are available, such as nonvolatile mass tags. See, for example, US Patent Application No. 2003/0022225 to Monforte et al., titled "Releasable nonvolatile mass label molecules," and U.S. Pat. No. 6,635,452 to Monforte et al. titled "Releasable nonvolatile mass label molecules," which are herein incorporated by reference. Volatile release taggants may also be utilized in some embodiments. See, for example, U.S. Pat. No. 5,610,020 to Giese et al., titled "Release tag compounds producing ketone signal groups," which is incorporated herein by reference. In some embodiments, a release taggant 240 may be presented in the matrix 218 as a lipid layer. See, for example, U.S. Pat. No. 6,949,347 to Singh and Chan-Hui, titled "Multiplex analysis using membrane-bound sensitizers," which is herein incorporated by reference.

In some embodiments, a sensor may include a matrix 218 that includes a gel configured to be responsive to a substance, wherein the gel is configured to emit a signal when the substance is detected. A signal may include a chromatic, fluorescent, luminescent, or aromatic signal, possibly as a releasable taggant. Examples include a polymerized crystalline colloidal array responsive to glucose. See, for example, U.S. Pat. Nos. 6,187,599 and 6,544,800 to Asher et al., titled "Polymerized crystalline collidal arrays," and U.S. Pat. No. 7,105,352 to Asher et al., titled "Intelligent polymerized crystalline colloidal array carbohydrate sensors," which are herein incorporated by reference. The Asher group at the University of Pittsburgh has also described the fabrication of polymerized crystalline colloidal arrays. See the attached printout of the Asher Laboratory materials titled "Colloid Group," accessed on Mar. 9, 2009, which are incorporated herein by reference.

In certain embodiments, the discrete oral component 101 might further include electronic circuitry, such as microcircuitry 251, and in some embodiments may include a power source 252 such as a microbattery, which may be housed, for instance, in the internal cavity 211 or within the outer shell 210. A power source may include rechargeable or replaceable power units. A power source may include wirelessly transmitted power sources, such as described in US Patent Application No. 2005.0143787 to Boveja, titled "Method and system for providing electrical pulses for neuromodulation of vagus nerve(s), using rechargeable implanted pulse generator," which is herein incorporated by reference. The system may also include additional sensors such as a thermometer or pH meter and/or instruments such as a timekeeping device or clock. The system may include one or more sensing device such as a temperature sensor, pH detector, pressure sensor, or time-keeping device. In some embodiments, one or more taggant, medicinal agent, or signal may be operably connected to one or more sensing device, such as a taggant or medicinal agent reservoir which is triggered to release material at a preset time point. In some embodiments, a signal may be generated in response to one or more sensing device, such as a light or vibratory signal that is generated in response to the detection of a temperature, pH or pressure range. In some embodiments, data from one or more sensing device may be transmitted or recorded along with the sensed data, such as when temperature or pH relevant to the sensor is included in information communicated to the external device.

The discrete oral component 101 may be configured as a single unit or as a plurality of regions, units, or modules, and may include layers of material. For example, the discrete oral component may include layers, units, modules or regions of supporting materials, gels, matrices, or shell structures. FIG. 3 depicts various aspects of potential material configurations within the discrete oral component 101. For example, as illustrated in FIG. 3A, the discrete oral component 101 may include layers such as concentric layers, with an inner sphere 311 and an outer sphere 310. For example, as illustrated in FIG. 3B, the discrete oral component 101 may include regions, for example configured in sections 331. The sections 331 may be modules. For example, as illustrated in FIG. 3C, the discrete oral component may include layers such as stratified layers 321, and may include one or more units configured as a scaffold. Multiple modular regions or layers may also form an indicator system for presence of a substance, such as described in the PCT patent application publication No. WO 2008/006152 A1 to Brockwell and Holland, titled "Indicator system for determining analyte concentration," which is herein incorporated by reference. In some embodiments, one or more recognition elements 215 may be configured in a region of the discrete oral component 101, such as the inner sphere 311 of a layered sphere, with perhaps as the outer sphere 310 a selective medium of an appropriate material and configuration, such as a gel or membrane. In some embodiments, one or more recognition elements 215 may be configured in a region of the discrete oral component 101, such as within one or more stratified layer 321. In some embodiments, one or more recognition elements 215 may be configured in a region of the discrete oral component 101, such as within one or more sections 331 or modules. A plurality of agents 316 may be present throughout or in distinct regions of the discrete oral component, as shown in FIGS. 3A, 3B and 3C. In some embodiments, various regions may be configured from different materials, such as a different type of gel, like sol gels with varying pore size, or pH-responsive or ion-responsive gels. Embodiments with various regions configured from different materials would allow for the sensing of a variety of substances in different units of the discrete oral component. Embodiments with various regions configured from different materials would allow for ready identification of sensed analytes, such as by identification that module X senses analyte Y, and therefore if module X has sensed a substance, it is inferred to be analyte Y. Referring now to FIG. 3C, in some embodiments, one or more gel or gel-like materials configured as part of the discrete oral component may include at least one recognition element 215 configured as one or more molecularly imprinted recognition site. See, for example, Byrne et al., "Molecular imprinting within hydrogels," *Advanced Drug Delivery Reviews* 54: 149-161 (2002), Peppas and Huang, "Polymers and gels and molecular recognition agents," *Pharm Res.* 19(5):578-87 (2002), and US Patent Application No. 2007/0190084 to Hilt et al., titled "Polymer network compositions and associated methods," which are herein incorporated by reference. In some embodiments, there may be a plurality of molecularly imprinted recognition sites associated with various recognition elements specific to particular regions. In some embodiments, the discrete oral component may include one or more gel configured to recognize and respond to a substance 220, for example a hydrogel that selectively recognizes and sequesters a metal. See, for example, Peppas and Huang, Ibid and Tanaka et al., "Polymer gels that can recognize and recover molecules," *Faraday Discuss.*, 102: 201-206 (1996), which are herein incorporated by reference.

Other compounds could similarly be included in the discrete oral component configured in an outer sphere 310, inner sphere 311, one or more sections 331, or one or more stratified layer 321. For example, regions of the discrete oral component may be configured to include one or more taggant 240. For example, materials may be included in the discrete oral component configured within an emulsion, in a coating 250, or may be incorporated into a structure such as a gel. In some embodiments, materials may be encapsulated 217, for example configured for release over time or configured for responsive release. A hydrogel may be configured for either slow release or responsive release of materials, depending on the embodiment. In some embodiments, materials may be retained in a reservoir within the discrete oral component 101, such as a reservoir configured to responsively release one or more medicinal agent. The discrete oral component 101 may include at least one reservoir configured to release at least one medicinal agent. Compounds configured within the discrete oral component 101 may include, for example, one or more medicine like an expectorant, a bronchodilator, a cough suppressant, a vasodilator, an analgesic, an anti-septic, an anti-infective, an antibiotic, a nutritional supplement, or a therapeutic; a substrate for a metabolic enzyme; and/or a substance able to be physiologically incorporated as through ingestion or inhalation. A substance able to be physiologically incorporated may include a diagnostic challenge like methacholine or an allergen, or may be an agent like dextrose or urea that is useful in testing the metabolic activity of the body or an infecting pathogen. See, for example, Pathak et al., Ibid, which is incorporated herein by reference.

Figure 4:
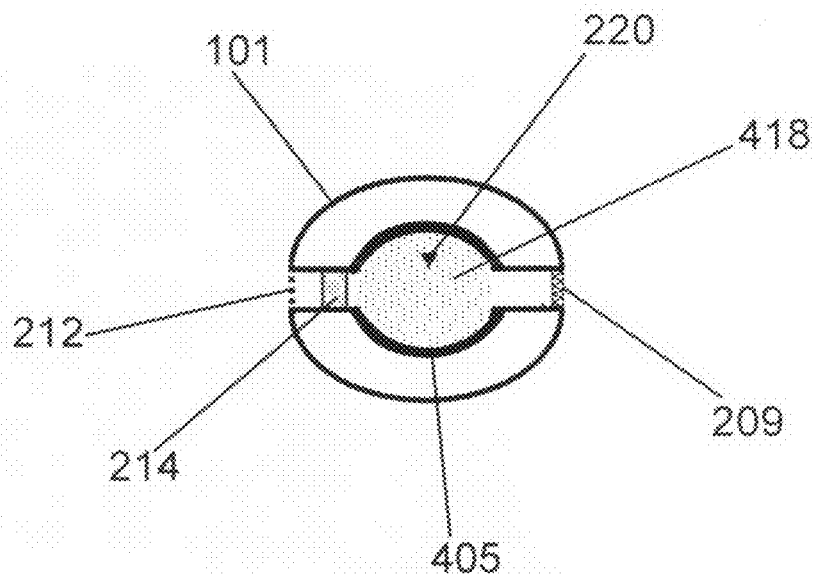
FIG. 4 is an illustrative view of a system.

As illustrated in FIG. 4, in some embodiments a responsive gel may be configured as at least one sensor integral to the discrete oral component 101. For example, a responsive gel may be operably connected to a transducer configured to convert the response of the gel into a signal. The presence of a substance 220, such as an analyte, may elicit a response from the gel, such as swelling, light emission or release of a taggant, which may be detected by a detector. The discrete oral component 101 may be configured to allow access to the gel through a permeable area 212 and/or a selective medium 214. A responsive gel may include a swellable hydrogel 418 operably connected to a transducer, such as a pressure sensor 405 configured to convert the swelling response of the gel into a signal. See, for example, Bromberg, "Intelligent polyelectrolytes and gels in oral drug delivery," *Current Pharmaceutical Biotechnology* 4: 339-349 (2003), which is herein incorporated by reference. A swellable hydrogel 418 may include proteins such as the reversibly swellable, biodegradable, cation-binding hydrogel described in U.S. Pat. No. 6,310,105 to Damodaran, titled "Carboxyl-modified superabsorbent protein hydrogel," which is herein incorporated by reference. In some embodiments, the swelling response of a gel may have stages responding to various ligands, which may be configured to be detectable by one or more transducers configured to respond to various stages of swelling. See, for example, Ehrick et al., "Genetically engineered protein in hydrogels tailors stimuli-responsive characteristics," *Nature Materials* 4: 298-302 (2005), which is herein incorporated by reference.

Examples of a transducer that may be configured for use with a responsive gel include a pressure sensor, perhaps of a piezoelectric material, such as an acoustical wave sensor or a cantilever sensor configured to convert the pressure of the gel into a sound, radiowave or wireless signal. See, for example: Drafts, "Acoustic Wave Technology Sensors," Sensors Magazine Online, Oct. 1, 2000; Tanaka et al., Ibid.; and Liu and Ji, "Detection of $Pb^{2+}$ using a hydrogel swelling microcantilever sensor," *Analytical Sciences,* 20:9-11 (2004), which are herein incorporated by reference. In some embodiments, a detector in an external device may receive a wireless signal through a port, and process the signal into results for display to at least one system user. The discrete oral component 101 may include a mechanism for removal of the hydrogel 418, for example by opening the discrete oral component 101 such as with a hinge 209.

Figure 5:
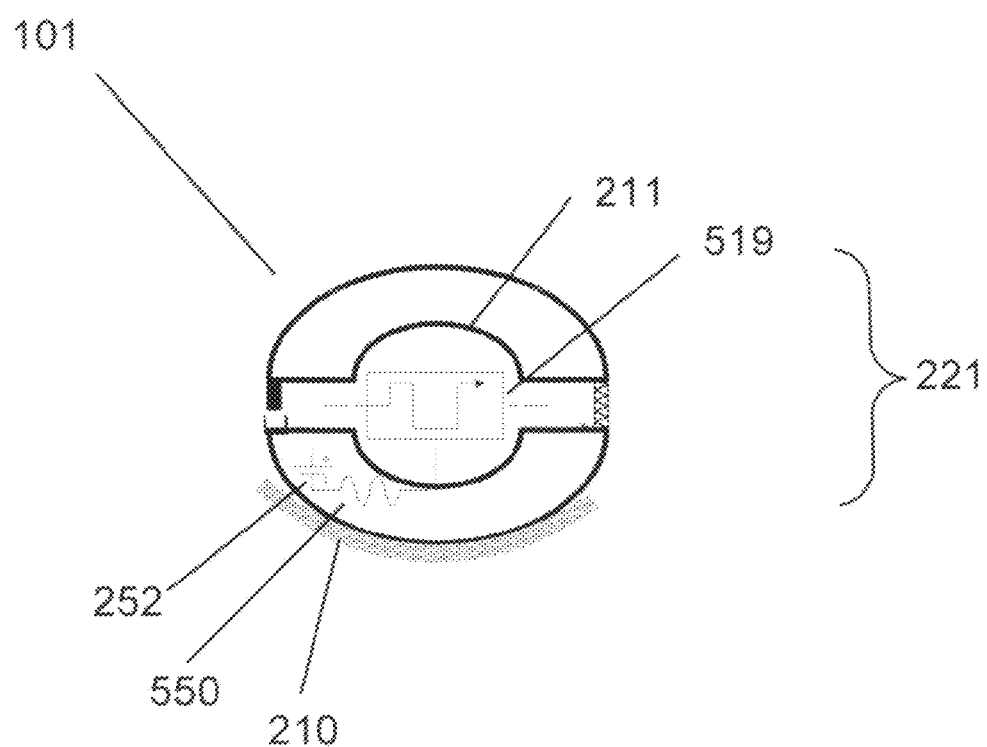
FIG. 5 is an illustrative view of a system.

As illustrated in FIG. 5, a discrete oral component 101 may include a plurality of regions 221, such as modular units. For example, as illustrated in FIG. 5, a discrete oral component 101 may include at least one inner cavity 211, at least one outer shell 210 and one or more electronic chip sensor 519. An electronic chip sensor 519 may be configured for reuse, multiple use, or single use. An electronic chip sensor 519 may be removable, swappable, or replaceable, such as an electronic chip sensor configured as a module. An electronic chip sensor 519 may be configured to interface directly with an external device through a port configured for communication, such as a port configured for communication through electronic circuitry. An electronic chip sensor 519 may be configured to interface directly with an external device through a port configured for communication, such as a port configured for communication through one or more wavelengths of light. An electronic chip sensor 519 may be configured to interface directly with an external device through a port configured for communication, such as a port configured for communication through vibration. In some embodiments, the interface between an electronic chip sensor 519 and an external device may be enhanced through an outer shell 210 of the discrete oral component 101. For example, an outer shell 210 may be configured to amplify or transmit one or more wavelengths of light. For example, an outer shell 210 may be configured to amplify or transmit vibration. Other instrumentation associated with the discrete oral component 101 may interact with the electronic chip sensor 519, such as one or more microfluidic device. Examples of electronic chips that may be configured for use with some embodiments includes immunoassay microchips and electrochemical DNA sensor chips. See, for example, Dill et al., "Immunoassays and sequence-specific DNA detection on a microchip using enzyme amplified electrochemical detection," *J. Biochem. Biophys. Methods* 5: 181-187 (2004) and Drummond et al., "Electrochemical DNA sensors," *Nature Biotech.* 21: 1192-1199 (2003), which are incorporated herein by reference. An electronic chip sensor may be configured for use with electronic, acoustic, or wireless technology to communicate remotely with an external device through a port, such as when a port is configured to be a receiver. See, for example: Yazawa et al., "A wireless biosensing chip for DNA detection," ISCC 2005 30.6; Baker, "Beaming Biodata," *MIT Technology Review* May 2005 (online edition); Heim, "Lab on a swab," *MIT Technology Review*, Aug. 29, 2005; and Hitachi Ltd. News Release "Development of the world's first RFID sensor chip for DNA analysis—SNPs in DNA detected using chip and reader only," Feb. 10, 2005, which are incorporated herein by reference. In some embodiments, a discrete oral component 101 including one or more electronic chip sensor 519 may include a power source 252, which may be configured to supply power to an electronic chip sensor through an electric transmission element, such as wires 550. A power source for a discrete oral component 101 may include one or more rechargeable elements. A power source for a discrete oral component 101 may include one or more transmitted power sources. See US Patent Application No. 2005/0143787 to Boveja titled "Method and system for providing electrical pulses for neuromodulation of vagus nerve(s), using rechargeable implanted pulse generator," which is herein incorporated by reference.

A discrete oral component 101, modules or portions thereof may be configured to be sterilizable through conventional techniques such as UVC exposure, autoclaving or steam cleaning. Similarly, one or more portions of a external device 102 may be configured to be sterilizable. For example, it may be desirable to sterilize a port 160 configured for direct contact with a discrete oral component 101. In some embodiments, the discrete oral component 101 and/or the external device 102 may include UVC capability to self-sterilize. For example, one or more UVC-emitting light source may be incorporated into the discrete oral component 101 and/or the external device 102, configured to sterilize the relevant surfaces before use or between uses. Similarly, one or more steam-emitting instruments may be incorporated into the discrete oral component 101 and/or the external device 102, configured to eliminate microbes on the relevant surfaces before use or between uses.

Following are a series of flowcharts depicting implementations. For ease of understanding, the flowcharts are organized such that the initial flowcharts present implementations via an example implementation and thereafter the following flowcharts present alternate implementations and/or expansions of the initial flowchart(s) as either sub-component operations or additional component operations building on one or more earlier-presented flowcharts. Those having skill in the art will appreciate that the style of presentation utilized herein (e.g., beginning with a presentation of a flowchart(s) presenting an example implementation and thereafter providing additions to and/or further details in subsequent flowcharts) generally allows for a rapid and easy understanding of the various process implementations. In addition, those skilled in the art will further appreciate that the style of presentation used herein also lends itself well to modular and/or object-oriented program design paradigms.

Figure 6:
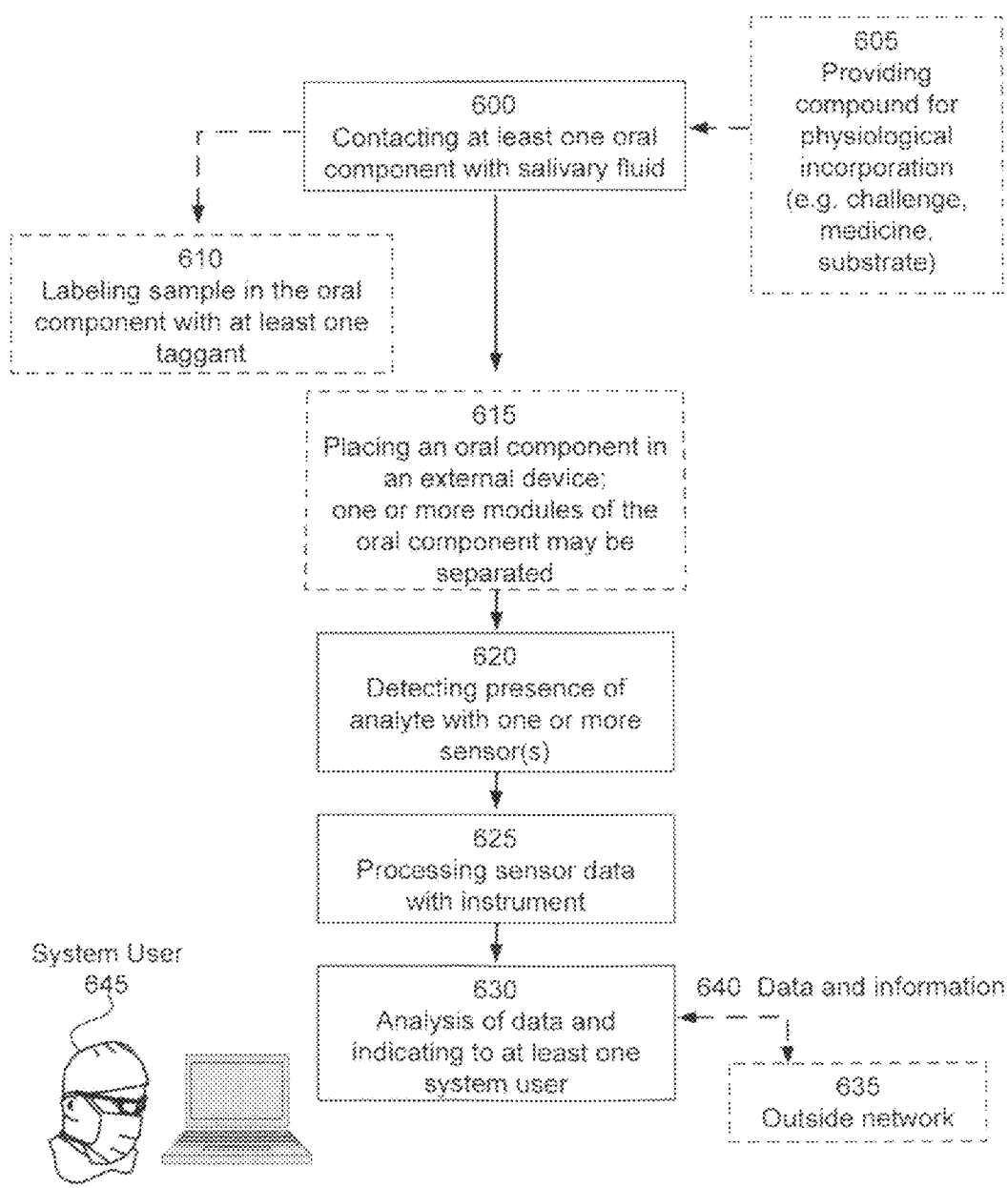
FIG. 6 shows a flowchart of a method.

As shown in FIG. 6, a method flowchart includes: contacting at least one oral component with salivary fluid 600; detecting presence of analyte with one or more sensor(s) 620; processing sensor data with instrument 625; and analysis of data and indicating to at least one system user 630. Some method flowcharts may include providing compound for physiological incorporation (e.g. challenge, medicine, substrate) 605. Some method flowcharts may include labeling sample in the oral component with at least one taggant 610. Some method flowcharts may include placing the entirety or a portion of an oral component in an external device; one or more modules of the oral component may be separated. In some method flowcharts, data and information 640 may be communicated between a system and an outside network 635. A system user 645, such as an individual, medical professional, caregiver, parent, animal handler, robotic user, or database operator may interact with the system directly or through an outside network. For example, a system user may interact directly with the external device, such as sensing an indication of one or more analyte being detected via a visual, auditory, or tactile route. For example, a system user may interact with a remote user interface device to view results from the external device.

Figure 7:
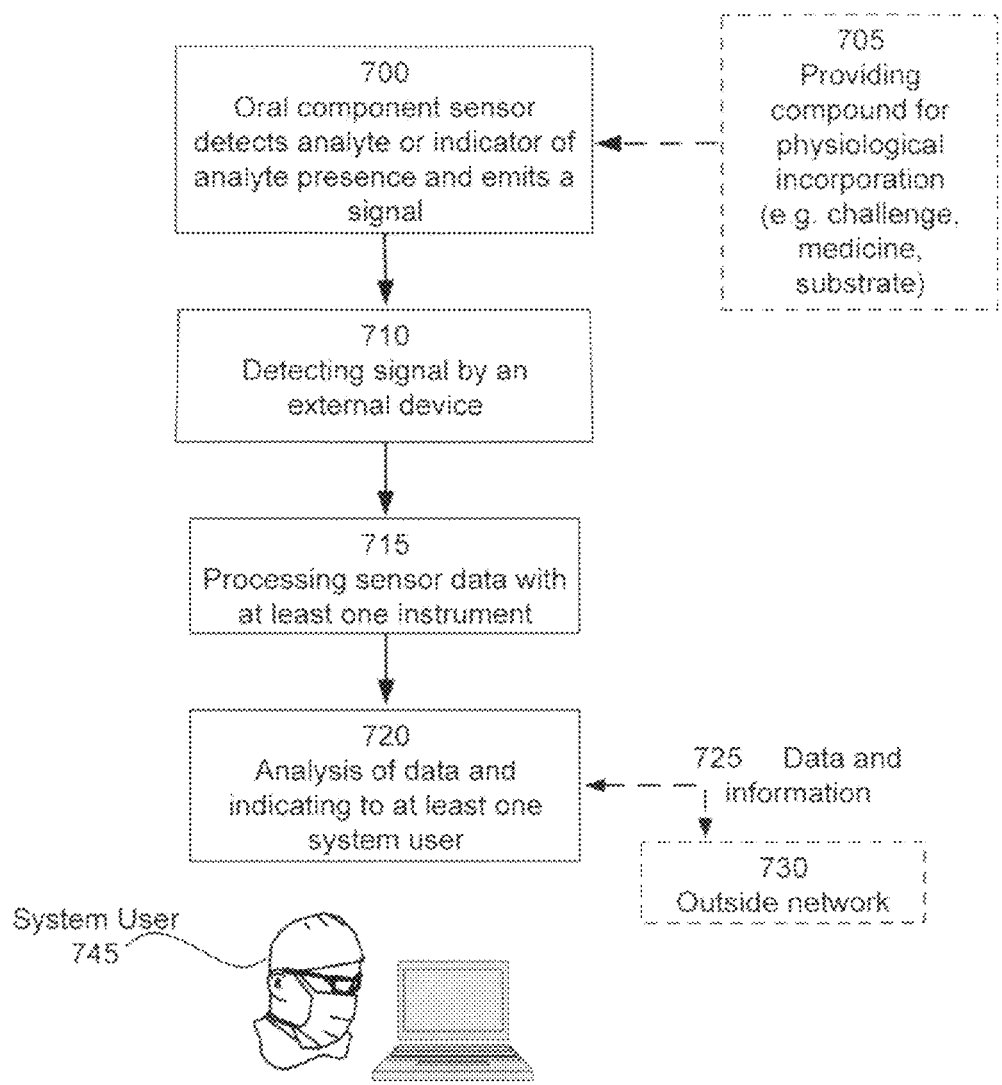
FIG. 7 illustrates a flowchart of a method.

FIG. 7 illustrates aspects of a method. A method flowchart includes: oral component sensor detects analyte or indicator of analyte presence and emits a signal 700; detecting signal by an external device 710; processing sensor data with at least one instrument 715; and analysis of data and indicating to at least one system user 720. Some method flowcharts may include providing compound for physiological incorporation (e.g. challenge, medicine, substrate) 705. In some method flowcharts, data and information 725 may be communicated between a system and an outside network 730. A system user 745, can include, for example, another computer system, an individual, a medical professional, a caregiver, a parent, a robotic user, an animal handler, or a database operator may interact with the system directly or through an outside network. For example, a system user may interact directly with the external device, such as sensing an indication of one or more analyte being detected via a visual auditory or tactile route. For example, a system user may interact indirectly with the external device, such as through a user interface device operably connected to the external device through a network.

Although system users such as system users 645 and 745, are shown herein as a single illustrated figure, those skilled in the art will appreciate that "users" may be representative of a human user, a robotic user (e.g., computational entity), and/or substantially any combination thereof (e.g., a user may be assisted by one or more robotic agents) unless context dictates otherwise. A system user may interact with the system at a remote location and may interact with the system at any time (such as, for example, a later time to view results stored on the system). Those skilled in the art will appreciate that, in general, the same may be said of "sender" and/or other entity-oriented terms as such terms are used herein unless context dictates otherwise.

In some methods, a system is configured to determine the presence of one or more analyte in salivary fluid and communicate the result. As diagrammed in FIG. 6, a discrete oral component is configured to collect a sample of salivary fluids or a constituent thereof. The discrete oral component is placed, possibly using an instrument, entirely into the oral cavity of an individual. Encapsulated flavoring included in the oral component may encourage use of the oral component and may induce salivation. In some embodiments, a permeable area of the rigid oral component is configured to allow salivary fluids to flow past, such as through a selective material covering a permeable area or a matrix. The selective material, such a filter or membrane, is configured to filter out debris, cells, sized molecules, charged molecules and/or any other undesirable material, even excess moisture, and configured to allow certain other substances to pass through. For example, a selective medium made of cellulose configured with pores of a certain size may allow diffusion of certain sized molecules, or a hydrogel film may swell at a certain pH to become more permeable and allow salivary fluids and/or constituents flow past.

The discrete oral component itself or a module thereof, such as a matrix, layer or section, may include one or more absorbent, for instance a dehydrated gel, such as a dehydrated porous gel. See U.S. Pat. No. 6,372,248, to Qin et al, titled "Dehydrated Hydrogels," which is incorporated herein by reference. A dehydrated gel may be configured to swell as the salivary fluids infiltrate, thereby retaining a portion of the fluids. In some instances, the hydrogel may be configured to swell with increased fluid retention or change in pH, and one or more flavorant may be released in a manner operably dependent on the amount of swelling, such as by being passively or actively displaced by the sample. Over time a pleasant flavoring may not be released, such as when the pleasant flavorant is depleted, and an unpleasant flavorant may released or accumulated, encouraging removal of the oral component from the oral cavity.

Figure 8:
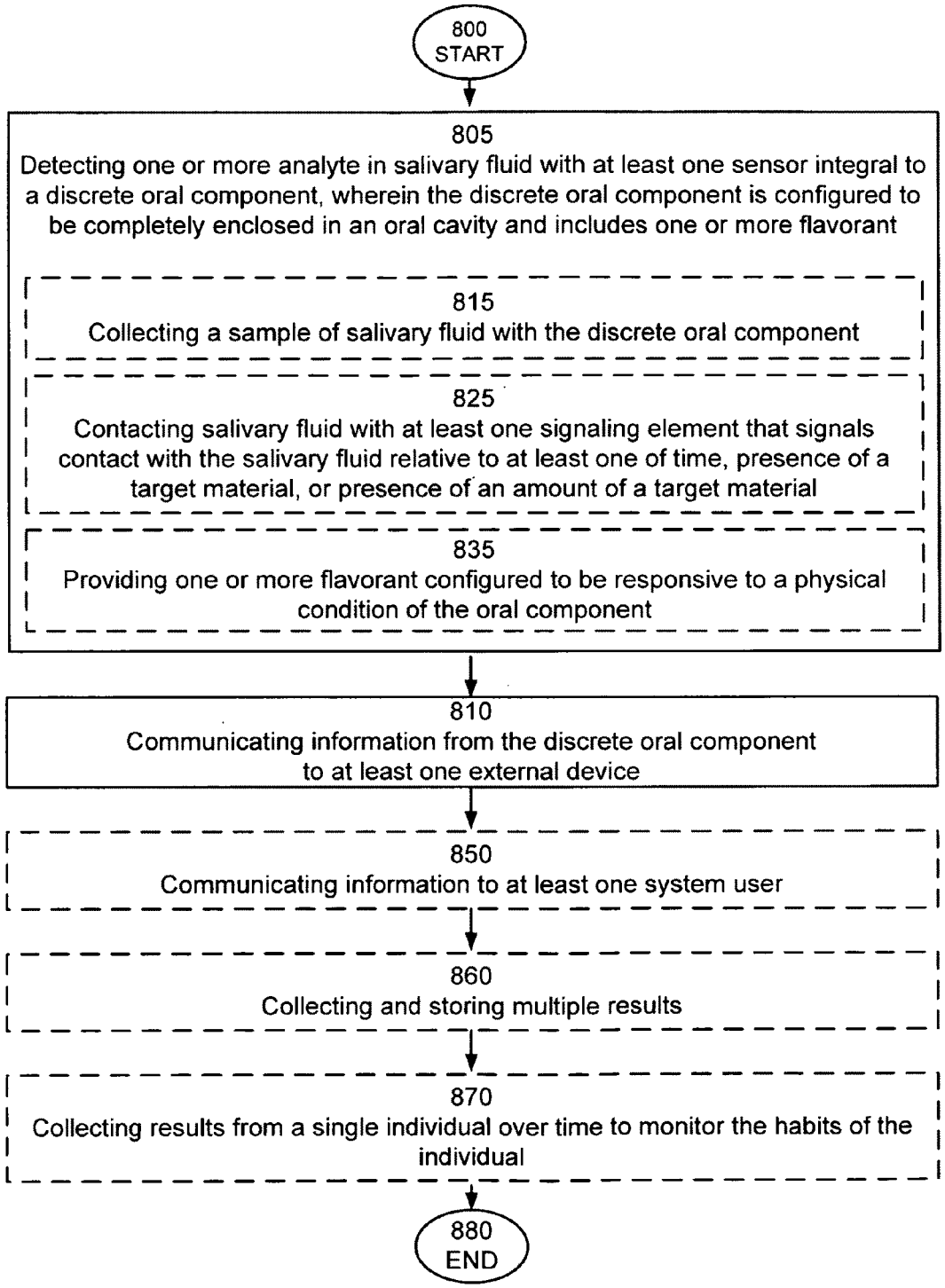
FIG. 8 depicts a flowchart of a method.

FIG. 8 depicts aspects of a method. The start of the method is depicted as 800. Method step 805 shows detecting one or more analyte within salivary fluid with at least one sensor integral to a discrete oral component, wherein the discrete oral component is configured to be completely enclosed in the oral cavity and includes one or more flavorant. Method step 810 depicts communicating information from the sensor to at least one external device. Method step 805 may include providing one or more flavoring with at least one flavorant that changes chemical composition during contact with salivary fluid. For example, one or more flavorant may change chemical composition during contact with salivary fluid relative to at least one of time, presence of a target material, or presence of an amount of a target material. For example, one or more flavorant may change chemical composition relative to pH of the salivary fluid. For example, one or more flavorant may change chemical composition through binding one or more components of salivary fluid. Method step 805 may include one or more of method steps 815, 825, or 835. Method step 815 depicts collecting a sample of salivary fluid with the discrete oral component. In some embodiments, sampling salivary fluid and detecting one or more analyte may occur simultaneously. Method step 825 illustrates contacting salivary fluid with at least one signaling element that signals contact with salivary fluid relative to at least one of time, presence of a target material, or presence of an amount of a target material. For example, a signaling element may signal contact with salivary fluid by releasing at least one of a chromogen, a fluorogen, an ink, a dye, or a flavoring. For example, a signaling element may signal contact with salivary fluid by vibrating, emitting light, emitting sound, emitting flavorant, or emitting an electrical stimulus (such as providing a shock) or transmitting a signal to the external device or to a network. Method step 835 shows providing one or more flavorant configured to be responsive to a physical condition of the oral component. For example, one or more flavorant may be configured to be responsive to hydration levels, pH, temperature or physical compression of the oral component. In some embodiments, the signaling element may include at least one flavorant. The method may also include steps 850, 860, 870. Method step 850 illustrates communicating information to at least one system user. Method step 860 shows collecting and storing multiple results. Method step 870 depicts collecting results from a single individual over time to monitor the habits of the individual. The end of the method is shown as 880.

One or more flavorant may be configured to be responsive to use of the discrete oral component. One or more flavorant may be configured to change chemical composition during contact with salivary fluid relative to at least one of time, duration of physical pressure, presence of a substance, or presence of amount of a substance. For example, the system may be configured so that when enough substance has been collected the flavoring changes, and thus notifies the user that the device can be removed. Distinct flavorants may be stored in different modules of the discrete oral component, and may be released, for example, in response to accumulation of the salivary fluid or substance. In some embodiments, a flavorant may be passively displaced as salivary fluid or substance is collected, such as by swelling of the oral component, perhaps through rehydration of previously dehydrated matrix. In some embodiments, flavorant may be released actively, for example flavorant immobilized in a substance-responsive gel may be released by changes in the gel upon binding a substance, and the gel may release different size or types of encapsulated or emulsified droplets being displaced at different intervals.

Either a rigid or soft oral component may be configured so that salivary fluid may be directed to specific portions of the oral component using a selective medium in the permeable area or as one of a plurality of units like an outer shell, layer, covering, or as part of a matrix. A selective medium is configured to allow only certain fluids or substances to pass. For example, an oral component may be configured to include a screen with a cellulose membrane containing pores sized to let smaller molecules pass and to block passage of larger ones, such as protein complexes or cellular debris. As another example, an oral component may be configured to include as the selective medium or matrix cover a gas permeable polymer gel like a polysiloxane, designed to allow only gas molecules to pass. In some embodiments, a selective medium may be such as configured to allow only unidirectional passage of molecules, such as a polysiloxane configured to allow for unidirectional permeation of gases.

After the discrete oral component has been retained in the oral cavity for a sufficient time period, it is removed from the oral cavity. In some embodiments, the time period may be marked by a change in the discrete oral component, such as a change in flavor, density, vibration, swelling, color, or light. After removal from the oral cavity, the discrete oral component or a module thereof may be placed in direct contact with the external device. For example, the discrete oral component or a module thereof may be placed in contact with a port including a cavity or receptacle. One or more instrument incorporated within or operably attached to the external device may process the sample, for example utilizing microfluidics, microarrays or electronic chips, which may include the addition of a taggant to the substance or associated material. A sensor in communication with the port may determine the presence or absence of the substance in the sample, either directly or by detecting a taggant. A sensor may be configured to detect a substance or the taggant for instance by utilizing gas chromatography; mass spectrophotometry; or optical, acoustic, magnetic, electric, and/or electrochemical technology. Additional technologies might also or instead be included, such as magnetic resonance, nanotechnology, and/or selective resonance techniques. See US Patent Application No. 2007/0021458 to Ishikawa et al., titled "Selective resonance of bodily agents," and Li et al., "The oral fluid MEMS/NEMS chip (OFMNC): diagnostic and translational applications," *Adv. Dent. Res.*, 18: 3-5 (2005), which are herein incorporated by reference. In one example, the discrete oral component includes at least one hydrogel with one or more embedded antibody as the recognition element. The antibody recognizes and binds a specific viral capsid protein, and the recognition alters the density of the gel. Encapsulated in the gel is a volatile small molecule which is released when the gel conformation is altered. An electronic nose would detect the volatile molecule being released from the gel thereby indicating the presence of the viral protein.

Some methods may use minimally- or non-invasive techniques to enhance the sampling of mucosal transudate or exudate. As an example, a chemical permeation enhancer such as isopropyl myristate or bile salts included in a coating of the oral component would increase the general permeation in the tissues of the mouth, or if oral component is held in place as between the cheek and teeth the coating would increase permeation locally. As another example, a magnetic component housed in a rigid shell or included in a layer of the oral component may increase transfer. Other technologies that might be utilized include iontophoresis, microdialysis, ultrafiltration, electromagnetic, osmotic, electroosmosis, sonophoresis, microdialysis, suction, electroporation, thermal poration, microporation, microneedles, microfine lances, microfine cannulas, skin permeabilization, or a laser. In some embodiments, electronic circuitry, such as microcircuitry could control the transfer.

Figure 9:
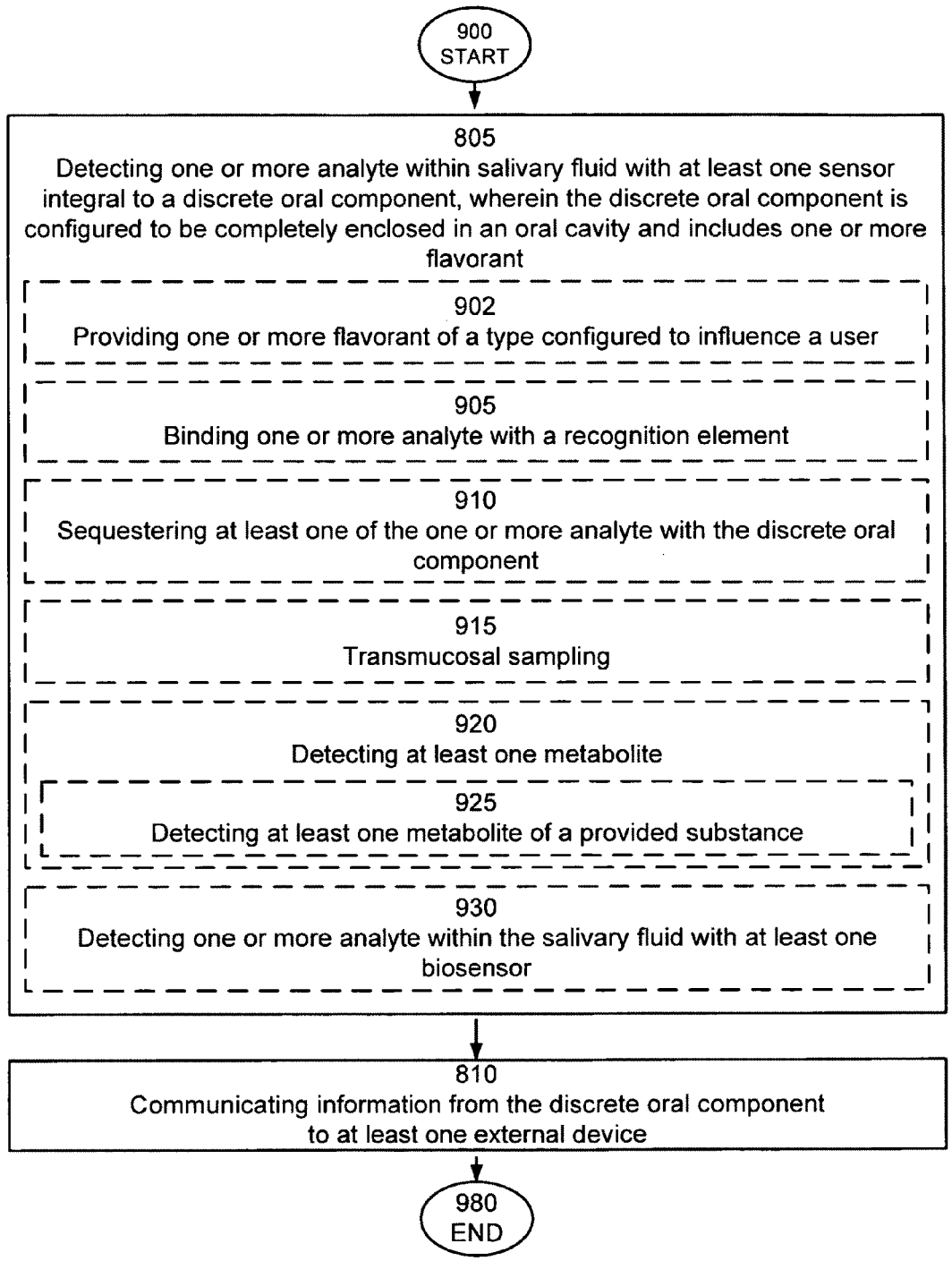
FIG. 9 shows a flowchart of a method.

FIG. 9 depicts aspects of the method flowchart illustrated in FIG. 8. The start of the method is depicted as 900. Method step 805, showing detecting one or more analyte within salivary fluid with at least one sensor integral to a discrete oral component, wherein the discrete oral component is configured to be completely enclosed in the oral cavity and includes one or more flavorant, may include one or more of steps 902, 905, 910, 915, 920, 925, or 930. Step 902 illustrates providing one or more flavorant of a type designed to influence a user. Step 905 shows binding one or more analyte with a recognition element. Step 910 depicts sequestering at least one of the one or more analyte with the discrete oral component. Step 915 illustrates sampling transmucosal tissue. For example, the method may include sampling with minimally invasive techniques. For example, the method may include techniques including iontophoresis, microdialysis, ultrafiltration, magnetism, electromagnetism, osmotic pressure, sonophoresis, magnetophoresis, microdialysis, suction, electroporation, thermalporation, microporation, and skin permeabilization. For example, sampling transmucosal tissue may include the use of microneedles, microfine lances, cannulas, chemical permeation, or lasers. Step 920 shows detecting at least one metabolite. For example, some method steps may include detecting at least one metabolite of a type that is indicative of a metabolic status. Step 920 may also include step 925, showing detecting at least one metabolite of a provided substance. Step 930 illustrates detecting one or more analyte within the salivary fluid with at least one biosensor. The end of the method is depicted as 980.

Methods may include sampling for specific substances by utilizing at least one recognition element, which may be located within a matrix configured in a discrete oral component. A recognition element may recognize, bind, and sequester a substance. As an example, a recognition element such as the binding peptide RGDS immobilized in a crosslinked hydrogel may be configured to recognize and bind one or more integrin. See Gonzalez, "Integrin Interactions with Immobilized Peptides in Polyethylene Glycol Diacrylate Hydrogels," *Tissue Engineering*, 10(11/12):1775-1786 (2004), which is herein incorporated by reference. In some embodiments, integrin may cross into an internal cavity of a discrete oral component through a selective medium of cellulose-based material, molecularly sized to keep cells out of the internal cavity. For example, a discrete oral component may include at least one substance-responsive gel configured to capture a substance and then swell, for instance a glucose-responsive gel that swells in the presence of glucose, or a hydrogel that selectively recognizes and sequesters a metal. See Peppas et al., "Polymers and gels as molecular recognition agents," *Pharm Res.* 19(5):578-587 (2002), and Tanaka et al., "Polymer gels that can recognize and recover molecules," *Faraday Discuss.*, 102: 201-206 (1996), which are herein incorporated by reference. In some embodiments, multiple substances may be sampled with multiple recognition elements, such as multiple recognition units configured into a plurality of modules within the discrete oral component. In some embodiments multiple substances may be sampled during a single use of the discrete oral component. Where multiple substances are sampled simultaneously or concurrently, at least one may be a reference substance such as total IgG. One or more reference substances may be collected, for example, for quantitative purposes or to calibrate the system.

In some embodiments, the system may include modules configured for removal and replacement. For example, in some embodiments a rigid outer shell of a discrete oral component may be configured to open and close at one or more closure by engaging a fitted, screwed or magnetic latch with or without utilizing a hinge. Opening the discrete oral component may reveal an internal cavity configured to hold other components, such as a matrix structure. After the discrete oral component is utilized and removed from an oral cavity, the closure is opened and the matrix structure containing the sample is removed. Removal of the discrete oral component from an oral cavity may potentially be facilitated with an instrument. After the discrete oral component has been utilized, to refurbish the outer rigid shell for subsequent use, a new matrix structure may be added to the internal cavity of the used outer shell, possibly after the unit is cleansed, sterilized, autoclaved or sanitized. For example, the unit may be sanitized through exposure to steam or UVC. One or more flavorant may be added to a refreshed, refilled, or recharged matrix structure module. An individual matrix module may employ a single material such as a gel, possibly with sections, to release flavorant as well as to bind an analyte in salivary fluid. In some embodiments, a permeable covering may encase material thus forming a package including, for example, one or more matrix and flavorant release material. In some embodiments, modules are swappable for different components. For example, a used matrix may be replaced with a different type of matrix. For example, in detecting a substance that is a surface protein produced by a microbe, a first matrix may be configured to contain as the recognition element a monoclonal antibody specific for the surface protein, which may be complexed to agarose beads and enclosed in a cellulose covering. The antibody would recognize, bind, and sequester the surface protein. After the discrete oral component is removed from an oral cavity, the first matrix may be replaced with a discrete second matrix configured to include as its recognition element another monoclonal antibody specific for a cytokine, for instance one known to be upregulated in the presence of the microbe. When the oral component is used again, the recognition element in the second matrix would bind and sequester the cytokine. Numerous types of recognition elements and matrices can be configured as needed to sample for a variety of substances. Detection of one or more substances may be carried out occasionally or may be implemented as part of a routine, for instance each day of the week. Or, the same substance may be sampled for over several days, as in a time course such as to monitor hormone levels for fertility hormone or therapeutic drug level detection. Multiple recognition elements may also be used at simultaneously to test for more than one substance.

In some embodiments, methods include labeling a substance with a taggant. For example, a cyanine dye present in the internal cavity or matrix of the oral component may dye nucleic acids as they come into contact with the dye. Or one or more recognition elements may be configured to include a taggant. For example, a recognition element including fluorescent-conjugated antibody may be configured so that as the antibody binds a protein substance, a labeled complex is formed. For example, a recognition element including enzymatic abilities may be configured to add a taggant, such as a radioisotope-containing carbohydrate or phosphate group, directly to a substance. For example, a recognition element including enzymatic abilities may be configured to add a taggant, such as a colorimetric, chromogen or fluorogen. In some embodiments, an inactive taggant may be configured to be activated as it binds the substance. For example, a recognition element may be configured to include a fluorescent binding molecule carrying both a fluorophore and a quencher with no initial signal, but when the recognition element binds the substance the quencher and fluorophore are separated, resulting in fluorescence. See, for example, Chen et al., "Fluorescent, Sequence-Selective Peptide Detection by Synthetic Small Molecules," *Science* 279:851-853 (1998), which is herein incorporated by reference. As an example, a flavored, rigid oral component may be configured to hold a matrix module within a membrane covering. The matrix module may be configured to include a recognition element including a metal-ligand complex with a fluorophore and a quencher. In the presence of glucose, the quencher will be displaced, resulting in the emission of fluorescence. See Tolosa et al., "Lifetime-Based Sensing of Glucose using Energy Transfer with a Long Lifetime Donor," *Analytical Biochemistry*, 250:102-108 (1997), which is herein incorporated by reference. Such a discrete oral component may be placed in the mouth of a user, and, after sufficient time for glucose from the salivary fluid to permeate the oral component, be removed from the oral cavity. The matrix module may then be removed from the oral component and placed in proximity to the external device, such as into a port. A sensor in the external device in communication with the port would utilize optics, including a light-emitting diode as the light source, to excite and absorb the fluorescence from the oral component and thereby detect the presence of glucose. In other configurations, a recognition element may be configured to release a taggant as part of the reaction of binding the substance, such as when a taggant is released by enzymatic activity during binding. For example, an oral component may be configured to include an immobilized or dissolved sugar compound carrying a chromogenic tag, which would be recognized by a substance such as a glycosidase of a pathogen, resulting in the cleavage of the chromogen group and coloring of the oral component. A discrete oral component incorporating such a taggant configured for release after detection of a substance may be placed adjacent to an external device after a sufficient amount of time in an oral cavity. The sensor in the external device may communicate with the discrete oral component through a port, for instance a gas port or permeable window. The discrete oral component may also be configured to utilize as a binding label a stimuli-responsive hydrogel. For example, the discrete oral component may include a hydrogel with embedded antibodies that recognize a protein, and as the antibodies bind to the protein, the hydrogel scaffolding would change density and thereby label the sequestered protein as distinct from free protein.

Figure 10:
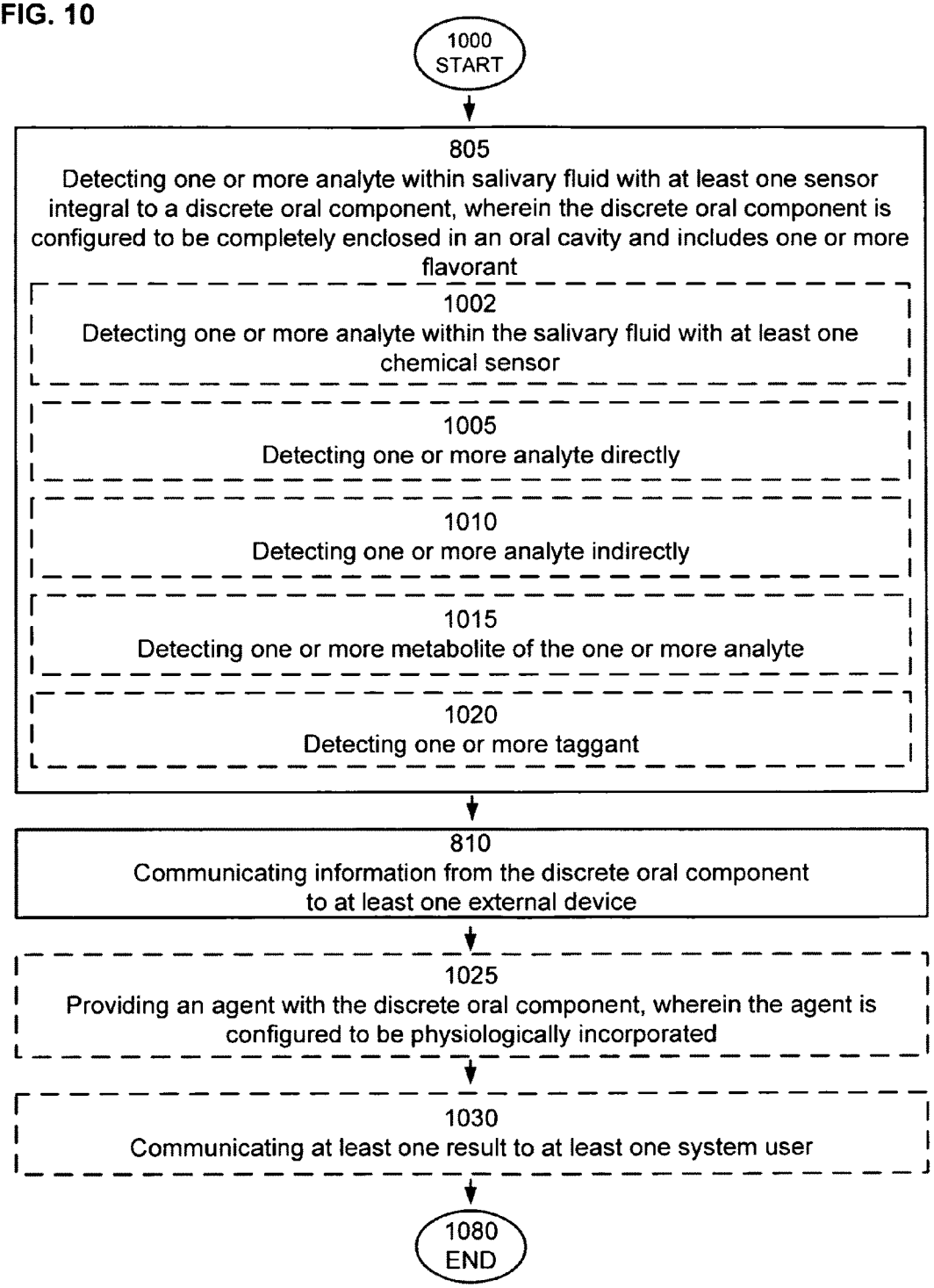
FIG. 10 illustrates a flowchart of a method.

FIG. 10 illustrates aspects of the method depicted in FIG. 8. The start of the method is shown as 1000. Method step 805, showing detecting one or more analyte within salivary fluid with at least one sensor integral to a discrete oral component, wherein the discrete oral component is configured to be completely enclosed in the oral cavity and includes one or more flavorant, may include one or more of steps 1002, 1005, 1010, 1015, or 1020. Step 1002 depicts detecting one or more analyte within the salivary fluid with at least one chemical sensor. Step 1005 illustrates detecting one or more analyte directly. Step 1010 shows detecting one or more analyte indirectly. Step 1015 illustrates detecting one or more metabolite of the analyte. Step 1020 shows detecting one or more taggant. Also depicted are steps 1025 and 1030. Step 1025 illustrates providing an agent with the discrete oral component, wherein the agent is configured to be physiologically incorporated. Some embodiments may include a method step wherein the agent is not provided with the oral component. In some embodiments, the agent may be provided from a source other than the oral component, such as a cup, spoon, or inhaler. The agent, provided in whatever manner appropriate to an embodiment, may include at least one medicine, expectorant, bronchodilator, cough suppressant, vasodilator, analgesic, anti-septic, anti-infective, antibiotic, nutritional supplement, or therapeutic. Step 1030 depicts communicating at least one result to at least one system user. The end of the method is shown as 1080.

Some methods may utilize agents stored with the discrete oral component, such as in an emulsion or encapsulated as in a coating, within a reservoir, within a gel, or in a covering of or within a matrix. For instance, some methods may utilize medicinal agents to enhance saliva or mucus production or to open bronchial airways. Diagnostic agents may also be utilized, such as methacholine or an allergen to challenge allergy or asthma responses of the oral component user. A labeled substrate for an enzyme may be utilized when gathering samples to test for the presence of a metabolic disorder or pathogen. As one example, urea, possibly carrying a label, may be stored in the oral component in a coating configured for release upon use of the oral component thereby resulting in urea being ingested by the user. If present, *H. pylori* in the gut would hydrolyze the urea and produce the metabolite $CO_2$, which is expelled in the breath (see, for example, "Urea breath test for *Helicobacter pylori* detection: present status," Pathak, Bhasin and Khanduja, *Trop Gastroenterol*. October-December; 25(4):156-61 (2004), which is herein incorporated by reference). Released $CO_2$ may either be sampled or sensed by the oral component. For example, an oral component may include a gas-permeable covering surrounding a matrix including a $CO_2$-sensitive hydrogel with a binding element that includes or is based on myoglobin. Such a matrix would bind and sequester the $CO_2$, which may be detected by an external device. Another embodiment includes a gas permeable membrane encircling a bicarbonate pH-sensitive gel that swells as $CO_2$ crosses into the gel. The gel swelling may be detected by a pressure sensor and a signal emitted. See, for example, presentation materials from Sebastiaan Herber and Wouter Olthuis, the University of Twente, The Netherlands, titled "A hydrogel-based CO2 sensor," which is herein incorporated by reference. Alternatively, an agent like urea may be ingested by an individual separately from the discrete oral component and the metabolite $CO_2$ detected by the oral component. In some embodiments, the system may sense a metabolite that includes a physiological analyte such as ethanol or acetone, at either endogenous levels or after providing an exogenous substrate like dextrose, provided in the oral component or separately. Such a metabolite might be sampled as part of a screening process for a metabolic disorder. In some embodiments, an oral component may include recognition elements configured to bind to a nonphysiologic agent that is acquired exogenously, such as to test for exposure to a pollutant. For instance, a discrete oral component with a recognition element that includes the enzyme acetylcholinesterase in a hydrogel may be used to sample for organophosphates. The acetylcholinesterase would irreversibly bind and sequester the organophosphates.

Figure 11:
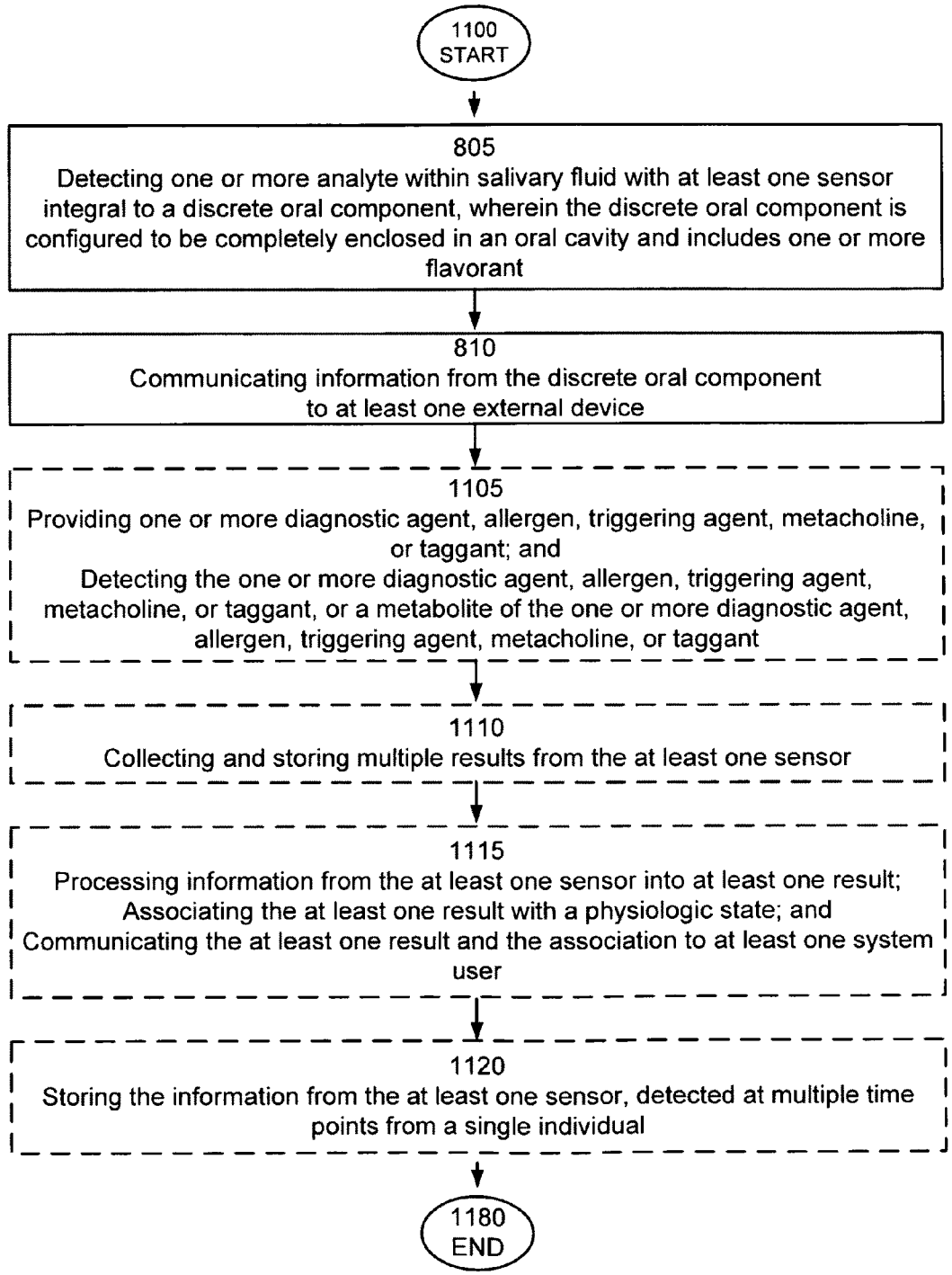
FIG. 11 depicts a flowchart of a method.

FIG. 11 depicts aspects of the method shown in FIG. 8. The start of the method is illustrated as 1100. Step 1105 depicts providing one or more diagnostic agent, allergen, triggering agent, methacholine, or taggant; and detecting the one or more diagnostic agent, allergen, triggering agent, methacholine, or taggant, or its metabolite. Step 1110 shows collecting and storing multiple results from the at least one sensor. A result may include detection of a taggant or an intermediate indicator such as a color change. For example, a method may include collecting and storing multiple results regarding a specific analyte at one or more time point. For example, a method may include collecting and storing multiple results regarding multiple analytes at one or more time point. For example, a method may include collecting the multiple results in a relative fashion. Step 1115 illustrates processing information from the at least one sensor into at least one result, associating the at least one result with a physiologic state, and communicating the at least one result and the association to at least one system user. Processing information may include, for example, utilizing at least one type of logic such as comparison, sorting, reduction and endpoint determination. Associating the at least one result may include, for example, associating the result with data from an external source. Associating the at least one result may include, for example, associating the result with at least one state related to cancer, lung function, infection, immune system function, cardiac system function, environmental exposure, risk, pregnancy, fertility, menopause, or therapeutic response. Step 1120 depicts storing information from at least one sensor detected at multiple time points from a single individual. Step 1180 shows the end of the method.

Figure 12:
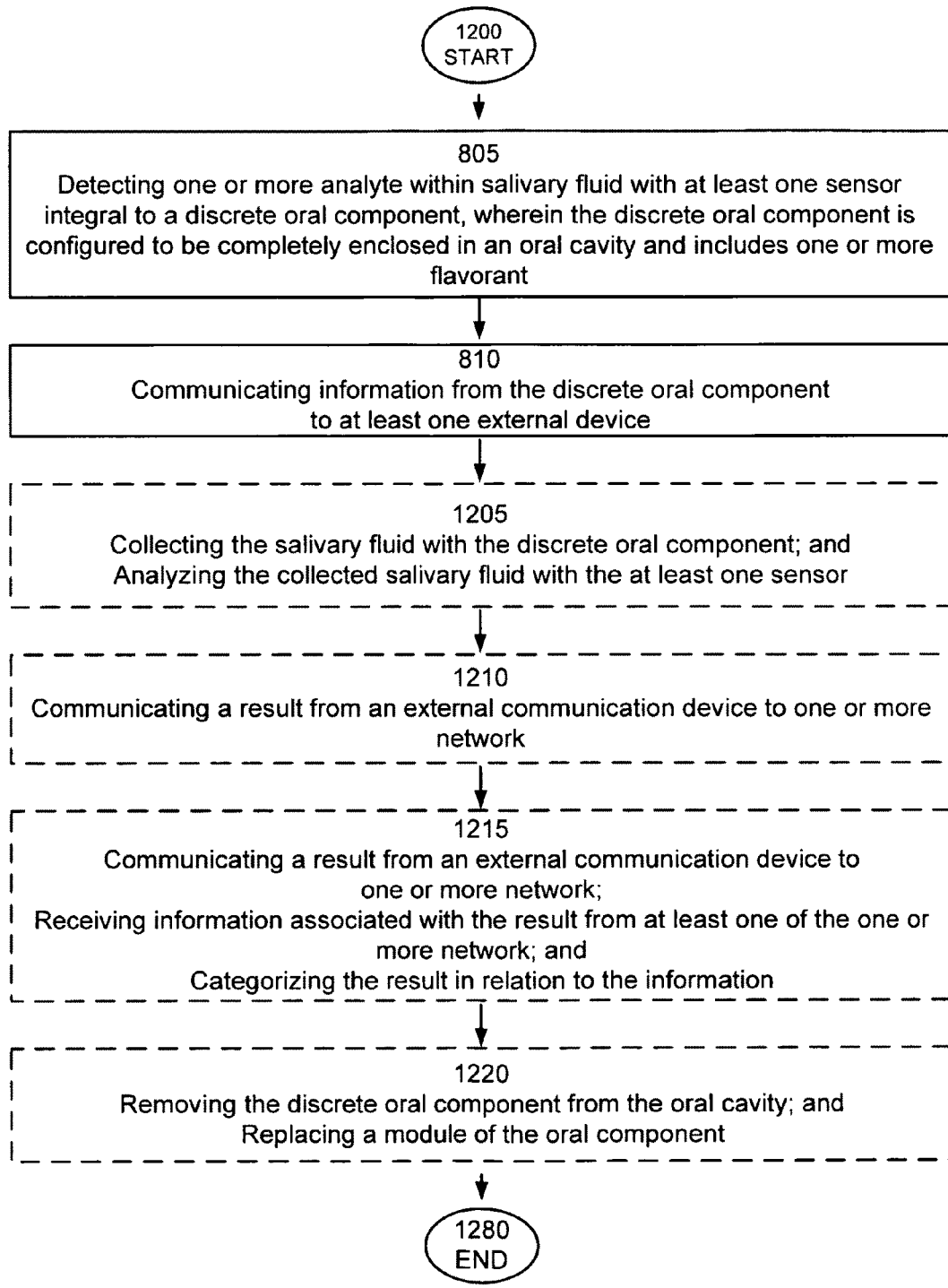
FIG. 12 shows a flowchart of a method.

FIG. 12 depicts aspects of the method shown in FIG. 8. The start of the method is illustrated as 1200. Step 1205 depicts collecting the salivary fluid with the discrete oral component, and analyzing the collected salivary fluid with the at least one sensor. Step 1210 illustrates communicating a result from an external communication device to one or more network. A method may also include receiving information from a network. A method may also include storing information received from a network. Step 1215 shows communicating a result from an external communication device to one or more network, receiving information associated with the result from the network, and categorizing the result in relation to the information. In some embodiments, a result may be encrypted. At least one network may include at least one localized area network, personal area network, or centralized network. Step 1220 depicts removing the discrete oral component from the oral cavity, and replacing a module of the oral component. Step 1280 illustrates the end of the method.

Figure 13:
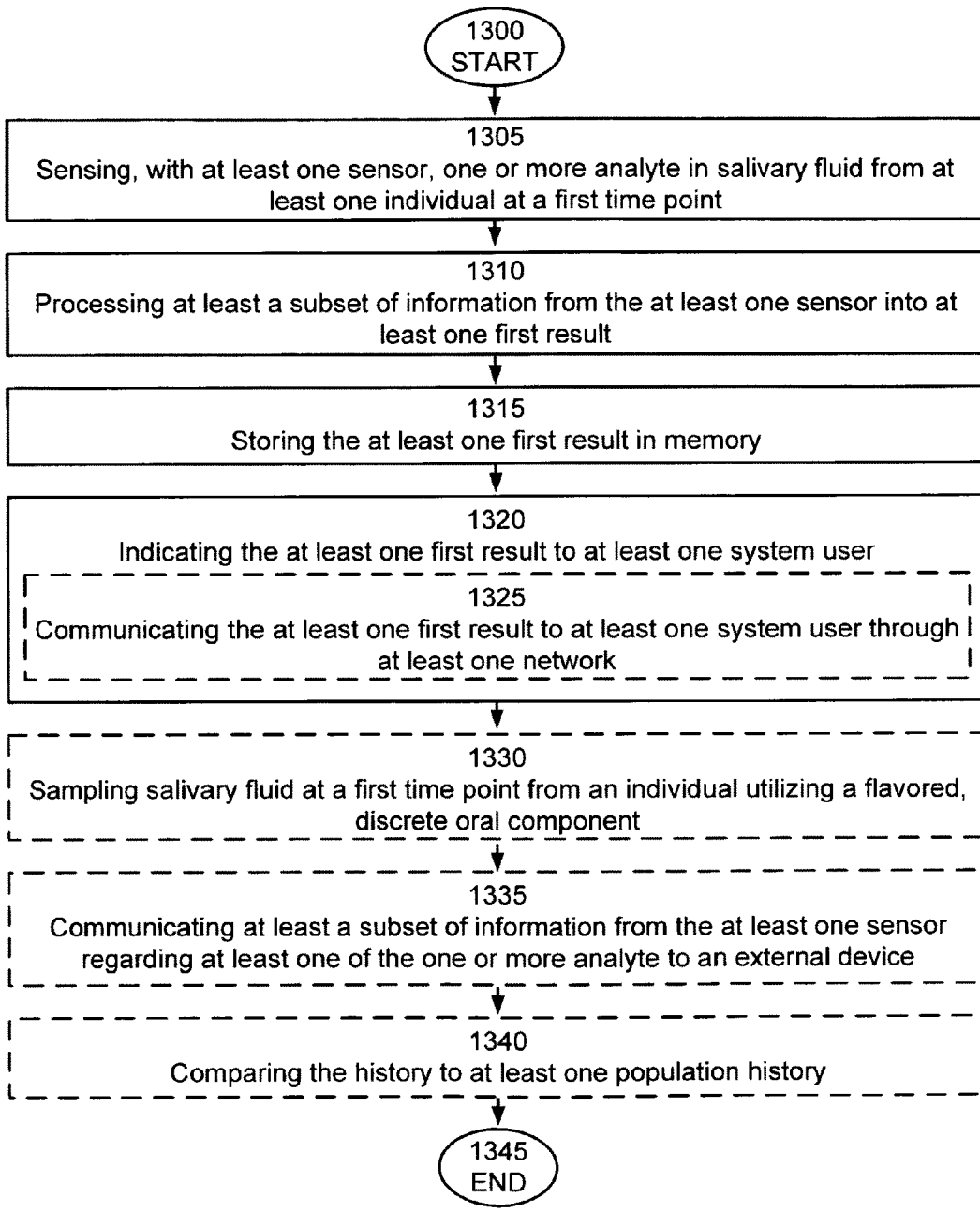
FIG. 13 illustrates a flowchart of a method.

FIG. 13 shows aspects of a method. The start of the method is illustrated as 1300. Step 1305 shows sensing, with at least one sensor, one or more analyte in salivary fluid from an individual at a first time point. Step 1310 depicts processing at least a subset of information from the at least one sensor into at least one first result. Step 1315 illustrates storing the at least one first result in memory. For example, the at least one first result may be stored in digital memory. Preferably, the memory is a form of digital memory storage. For example, the at least one first result may be stored on a floppy disk, flash drive, memory card, CD, hard drive, or network system. The memory may be integrated into the external device, a network, or an additional device. Step 1320 shows indicating the at least one first result to at least one system user. For example, the result may be indicated with a light signal, auditory cue, by a display, vibration emitter, or other indication mechanism. Step 1320 may include step 1325, illustrating communicating the at least one first result to at least one system user through at least one network. For example, a system user may include a health care provider, therapist, caregiver, or patient and the network may include a hospital or medical clinic based computer or computing network. For example, the at least one network may include at least one localized area network, personal area network, or centralized network. The method flowchart may include step 1330, depicting sampling salivary fluid at a first time point from an individual utilizing a flavored, discrete oral component. In some embodiments, sampling salivary fluid may occur simultaneously with sensing one or more analyte in the salivary fluid. The method flowchart may include step 1335, illustrating communicating sensed information regarding at least one of the one or more analyte to an external device. The method flowchart may include step 1340, showing comparing the history to at least one population history. For example, a individual history may be compared to a composite or aggregate history derived from data originating from a group of individuals in a population, such as a patient population of a hospital, a group of patients undergoing a common medical regimen or with a common diagnosis, a group of healthy individuals, or a group of individuals with common metabolic indicators. In some situations, a population may include individuals matched for demographic traits, such as age, weight, ethnicity, race, gender or lifestyle traits. Step 1345 depicts the end of the method.

Figure 14:
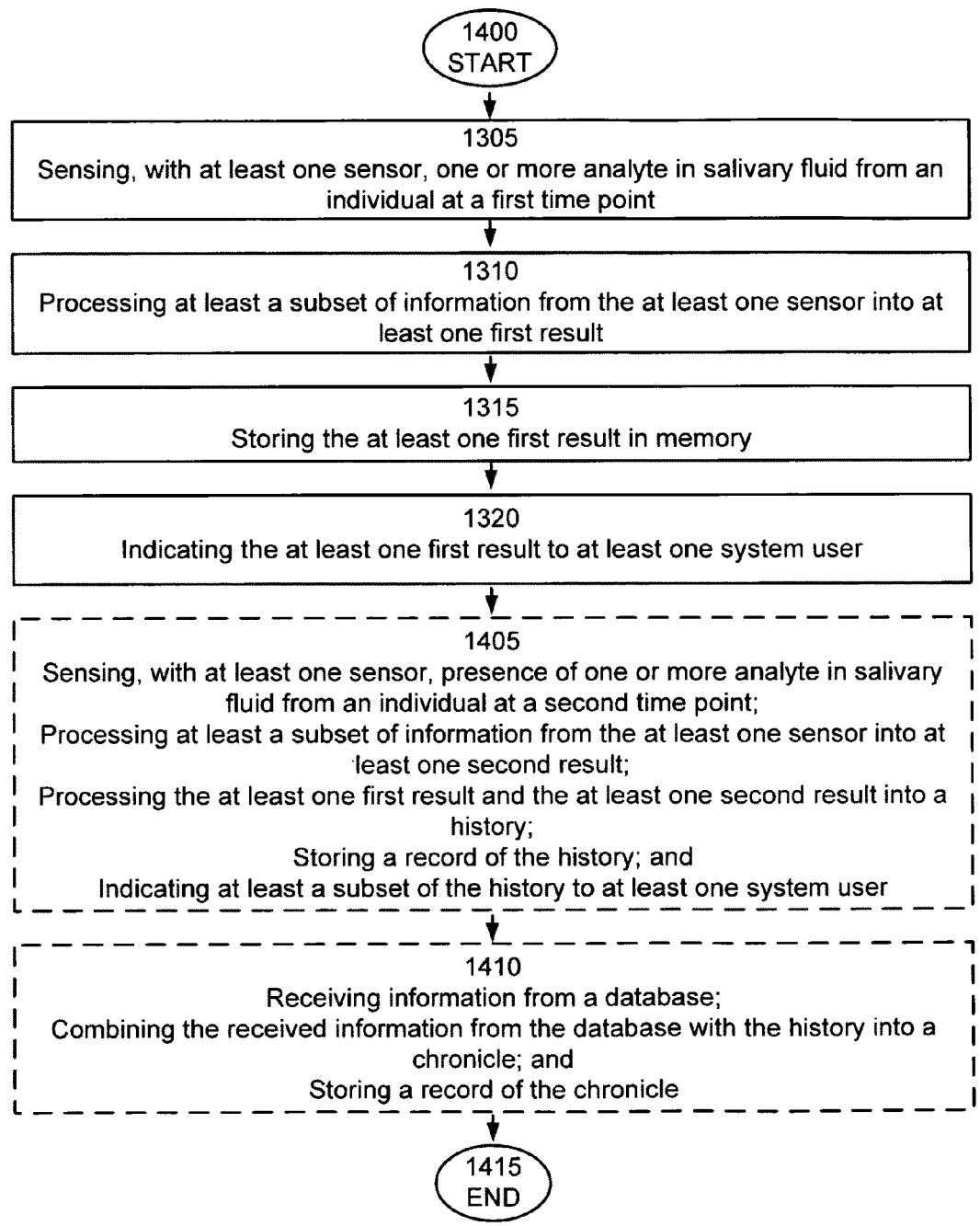
FIG. 14 depicts a flowchart of a method.

FIG. 14 depicts aspects of the method flowchart illustrated in FIG. 13. Step 1400 shows the start of the method. Step 1405 depicts sensing, with at least one sensor, presence of one or more analyte in salivary fluid from an individual at a second time point, processing at least a subset of information from the at least one sensor into at least one second result, processing the at least one first result and the at least one second result into a history, storing the history, and indicating at least a subset of the history to at least one system user. Method step 1410 illustrates receiving information from a database, combining the received information from a database with the history into a chronicle, and storing the chronicle. The end of the method is shown as 1415.

Signals provided by a sensor are processed by instrumentation within the external device, which is configured to collect and store the results as data points. The data points can be collected in a relative fashion, serially or in parallel, and stored as a function of time and/or as multiple results regarding a single analyte and/or multiple analytes collected at one or more time point. The system may further interact with one or more network, which would be specialized network, such as a localized area network like a domotics home automation system, a personal area network, or a centralized network, to send and receive information utilizing encryption technology. Systems and methods as described herein may be used to integrate with at least one healthcare network, as described in US Patent Application No. 2004/0078219 to Kaylor et al., titled "Healthcare networks with biosensors," which is herein incorporated by reference. The system might store such information, updating data while keeping or deleting the old data. Data from the results acquired by the system may be analyzed using stored information and logic such as comparison, sorting, reduction, and endpoint determination. Methods and systems such as those described herein may be utilized to establish and maintain a history of one or more individual. By interacting with one or more network, the history could be compared to and collated with population data and the history updated and stored remotely.

Systems and methods as described herein may be used in a variety of ways and for a variety of purposes. The information gained from systems and methods as described herein may be used to determine a physiologic status of the user, for example a state related to cancer; lung function; infection; a metabolic state; the immune system, including a dysfunctional immune system experiencing autoimmunity, hyperimmunity, allergic reactions, or a depressed/suppressed immune system; the cardiac system, like levels of cardiac electrolytes or blood chemistries including cholesterol; a state related to environmental exposure; a risk state; pregnancy; fertility; or therapeutic response like to medicine or diet. In addition to the health of a user, the habits and exposure of an individual may be monitored by detecting analytes such as a controlled substance, a pollutant, an ingested substance, an inhaled substance, an adsorbed substance, and an environmental effect. Monitoring may be implemented routinely, as on a daily or weekly schedule, for instance using the same components everyday to test for fertility-associated metabolic factors such as hormones. Or, the system may be utilized including the components in an alternate but routine fashion, replacing part of the system at each use. For instance, each day of the week a different test could be performed for a different analyte. Or, an occasional test could be performed as desired, for example to consider possible infection or pregnancy.

Other aspects of the systems and methods described herein are described in the examples below.

EXAMPLES

Example 1

A System for Detection of Influenza A/B Virus in Salivary Fluid

A system to detect influenza virus in salivary fluid includes: 1) a discrete oral component configured to capture viral analytes and communicate signals to 2) an external device configured to detect the oral component signal and transmit related information to 3) a computer system configured to receive, digitize, collect, analyze and store the transmitted information.

A discrete oral component made up of a durable plastic shell including a permeable area and a removable module including a hydrogel core is used to sample salivary fluid and capture influenza viral analytes. Antibodies are used in the hydrogel core to detect a variety of strains of influenza virus. Hydrogel modules include antibodies that have been described as able to detect and differentiate different hemagglutinin and neuraminidase proteins, (e.g. H1N1, H3N2) from different strains (e.g. A/New Caledonia/H1N1, A/Wellington/H3N2) or species (e.g. influenza A and influenza B) of influenza virus (see Korsman, "Chapter 6: Vaccines," in Influenza Report 2006, Kamps, Hoffman and Preiser, editors, *Flying Publisher*, pp 127-149, (2006) which is incorporated herein by reference). Antibodies specific for influenza A, including different strains of influenza A, or for influenza B are commercially available (for example, from BioPorto Diagnostics A/S, Gentofte, Denmark and AbD Serotec, Oxford, UK). For some modules, antibodies are prepared from animals exposed to influenza protein antigens that are cloned and expressed using recombinant DNA methods allowing identification and production of antibody cognate antigens and epitopes. See, for example, Khurana et al, "Antigenic Fingerprinting of H5N1 Avian Influenza Using Convalescent Sera and Monoclonal Antibodies Reveals Potential Vaccine and Diagnostic Targets," *PLoS Med.*, vol. 6, e1000049, pages 1-13, (2009) and U.S. Pat. No. 5,762,939 to Smith et al., titled "Method for producing influenza hemagglutinin multivalent vaccines using baculovirus" which are herein incorporated by reference.

Modules configured for the detection of influenza virus include reversibly antigen-responsive hydrogels, prepared by co-polymerizing two or more hydrogels each containing modified antigens or their cognate antibodies; such gels swell upon exposure to free antigen. See, for example, Miyata et al., "A reversibly antigen-responsive hydrogel," *Nature*, 399: 766-769 (1999), which is herein incorporated by reference. Antibodies specific for influenza viral antigens and their cognate antigens are incorporated into hydrogels and copolymerized to create hydrogels that swell in response to free viral antigen. Modules include those with hydrogels including a monoclonal antibody specific for influenza A nucleoprotein (available from AbD Serotec, Oxford, UK) and the corresponding antigen, a 60 kilodalton influenza A nucleoprotein. Such hydrogels are synthesized by modification of the proteins and subsequent copolymerization using N-succinimidylacrylate, ammonium persulfate, acrylamide and N,N,N',N'-tetramethylethylenediamine (chemicals available from Sigma-Aldrich, St. Louis, Mo.; for methods see Miyata et al., Nature, 399: 766-769 (1999) which is herein incorporated by reference). Antigens and antibodies are present in the hydrogel complex and induce rigidity. These complexes are disrupted by free viral antigen (e.g. 60 kilodalton nucleoprotein) present in salivary fluids from an infected individual. Disruption of the antigen-antibody complexes leads to swelling of the hydrogel.

Figure 15:
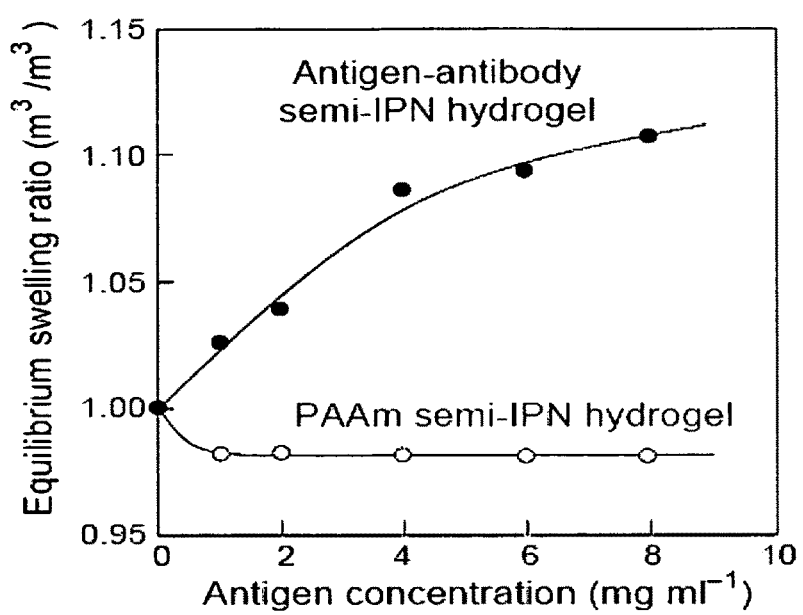
FIG. 15 illustrates swelling of a hydrogel containing antigen-antibody complexes versus free antigen concentration.

FIG. 15 depicts swelling of a hydrogel in response to increasing concentrations of antigen (taken from Miyata et al, Ibid.). The X-axis illustrates an equilibrium swelling ratio of a hydrogel containing antigen-antibody complexes, while the Y-axis depicts free antigen concentration. FIG. 15 also illustrates a comparison between a semi-interpenetrating network (IPN) hydrogel containing an antigen-antibody cognate pair and a control polyacrylamide (PAAm) semi-IPN hydrogel without antigen-antibody at increasing concentrations of free antigen. Swelling was measured in microns cubed. See Miyata et al, Ibid.

Some discrete oral components contain a single module that includes antibodies and cognate antigens specific for a single influenza species such as influenza A or B or C, or individual strains or subtypes of influenza A, such as H1N1 or H2N2 or H3N2 or H5N1. Such modules are most suitable for applications wherein there is a concern regarding a single influenza strain, such as during an epidemic or pandemic of a particular strain. However, some discrete oral components contain multiple modules (e.g. hydrogel modules) configured to allow for the simultaneous detection of multiple species and/or strains of influenza virus. Such discrete oral components are most suitable for general influenza screening for species and strains of virus considered to be most likely to be circulating at a given time.

To detect swelling in hydrogels that have been exposed to salivary fluids, the hydrogel modules are removed from the discrete oral component and analyzed with instrumentation associated with an external device. An increase in the volume of a hydrogel module shaped as a disc can be determined with an optical microscope by measurement of the gel disc radii (see Miyata et al, Ibid.). For example, the external device would have precision optics and LED lighting integrated into a small microscope (see, e.g. MiScope® Handheld Digital Microscope sold by Forensics Source, Jacksonville Fla.). Alternatively or in addition, the swelling is detected by a pressure sensor (see FIG. 4) connected to a transducer and configured to convert the swelling response of the gel into a radio frequency (RF) signal, which is wirelessly detected by a receiver in the external device. Swelling of control hydrogels lacking antigen-antibody complexes (e.g. see FIG. 15), and/or hydrogels with antibody-antigen complexes exposed to saliva from uninfected volunteers can be compared to test samples to calculate a swelling ratio as described in Miyata et al, Ibid.

As an alternative to a gel with swelling controlled by integrated complexes, some discrete oral components instead contain a micro-cantilever device, with an associated hydrogel containing a recognition element, such as an antibody. Piezoresistive micro-cantilevers are nanomechanical devices that can detect small stresses applied to the cantilever and signal via a piezoresistive electrical response. When an antigen binds to the antibody, the increased mass is transferred through the cantilever. An array of cantilevers would allow for more than one antigen, for example from more than one strain of influenza, to be recognized and measured. For example, a piezoresistive micro-cantilever may be fabricated from polysilicon, silicon nitride, silicon dioxide, chromium and gold using standard silicon microfabrication techniques such as reactive ion etching, wet etching and deposition techniques (see Wee et al, "Novel electrical detection of label-free disease marker proteins using piezoresistive self-sensing microcantilevers" Biosensors and Bioelectronics, 20: 1932-1938 (2005) which is herein incorporated by reference). A microcantilever and a reference micro-cantilever (a reference micro-cantilever may, for example, be configured without a receptor or recognition molecule attached) is connected to a half Wheatstone bridge and other electronic components (e.g. DC power supply, multimeter that are available from Agilent Technologies, Inc., Santa Clara, Calif.) and an amplifier (available from Analog Device, Inc., Norwood, Mass.) to allow differential measurement of resistance. Mechanical stress on the piezoresistive micro-cantilever results in changes in resistance which can be observed as voltage changes. For example, a piezoresistive micro-cantilever with an antibody immobilized on one face of the cantilever deflects when its antigen binds due to increased stress on the microcantilever. Micro-cantilever deflections are detected as voltage changes that increase with increasing antigen concentration.

Figure 16:
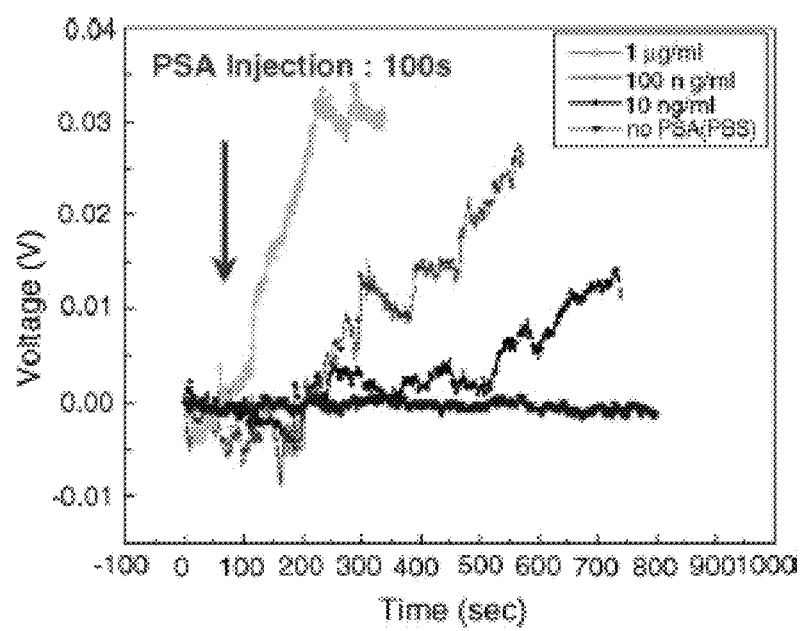
FIG. 16 shows deflection-induced voltage changes in a micro-cantilever system in response to increasing concentrations of PSA antigen.

FIG. 16 illustrates deflection-induced voltage changes in a micro-cantilever system in response to increasing concentrations of the antigen PSA. FIG. 16 adapted from Wee et al, Ibid. The X (vertical) axis depicts voltage while the Y (horizontal) axis shows time in seconds, note that PSA antigen was introduced at 100 seconds. Real-time monitoring of the micro-cantilever deflection signal is depicted as a function of PSA concentration (10 µg/ml, 100 ng/ml, 10 ng/ml, no PSA antigen). FIG. 16 also illustrates that voltage increases can be sustained for more than 200 seconds when PSA is present.

Discrete oral components with a rigid plastic outer shell are configured to hold and protect a micro-cantilever array inside an internal cavity while also being configured to allow access to salivary fluids. For example, see FIGS. 2A, 2B, 4 and 5. Voltage increases associated with the binding of influenza antigens are transformed into radiofrequency data and transmitted wirelessly to receiver in the external device. For example, a chip with an integrated micro-cantilever and electronic components is described in Wee et al, Ibid., that is configured to record voltage changes originating from a micro-cantilever.

Alternatively or in addition, a micro-cantilever can be configured to control a valve or gate that is connected to a reservoir containing a flavorant. For example, a micro-cantilever associated with a gate is coated on one face with an antibody specific for influenza B. When influenza B virions bind the immobilized antibody, the micro-cantilever gate is configured to open and allow flavorants such as 5-nitro-2-propoxyaniline (sweet), denatonium (bitter), citric acid (sour), or capsaicin (hot/spicy) (e.g. see the article, "Taste" displayed May 22, 2009 at Wikipedia.org, which is herein incorporated by reference) to flow out of the oral component into the mouth. Such a flavorant release indicates that influenza B has been detected in salivary fluid.

Depending on their composition and preparation, stimulus-responsive gels can be designed to alter their structure upon addition of the stimulus, for example swelling as above, or in some cases shrinking, thus providing a repertoire of useful configurations (see Ehrick et al, "Genetically engineered protein in hydrogels tailors stimuli-responsive characteristics," *Nature Materials,* 4: 298-302 (2005) which is herein incorporated by reference). A discrete oral component is configured to contain a hydrogel coupled with anti-influenza antibodies capable of binding influenza virions or influenza viral proteins, so that in the presence of influenza virions the hydrogel contracts and thereby opens a valve controlling a reservoir. A reservoir containing a dye, or flavorants, or any combination of signaling substances, is configured to be controlled by a valve responsive to the hydrogel. Alternately, a hydrogel is configured to form a retractable plug that blocks egress from a reservoir in the absence of binding a substance (see FIGS. 17 and 18). A microfluidic device with a reservoir is constructed from polycarbonate and a stimuli-responsive hydrogel used to control the reservoir valve. See FIGS. 17 and 18. Exposure of the hydrogel to an analyte (e.g. viral protein) causes the hydrogel plug to shrink and release the contents of the reservoir (see Ehrick et al, Ibid.).

FIG. 17 illustrates a schematic of a device with a stimuli-responsive hydrogel plug configured to retract after a substance binds to the hydrogel. A discrete oral component 101 includes an inner cavity containing a stimuli-responsive hydrogel 1700 and a reservoir 1705. In this example, the reservoir 1705 includes a flavorant such as those described herein. The stimuli-responsive hydrogel 1700 is configured to reversibly block access from the reservoir 1705. As shown in FIG. 17A, in the absence of substance binding the stimuli-responsive hydrogel 1700, the permeable area 212 and the access channel 1710 between the reservoir 1705 and the region external to the discrete oral component 101 is blocked by the stimuli-responsive hydrogel 1700. A substance 220 enters the inner cavity of the discrete oral component through a permeable area 212 and the access channel 1710. FIG. 17B illustrates that when a substance 220, such as influenza virons, binds the stimuli-responsive hydrogel 1700, retraction of the stimuli-responsive hydrogel 1700 occurs and the permeable area 212 and the access channel 1710 between the reservoir 1705 and the region external to the discrete oral component 101 is opened or unblocked. Material, such as flavorant, retained in the reservoir 1705 diffuses through the access channel 1710 and the permeable area 212.

FIG. 18 illustrates a schematic of a device with a stimuli-responsive hydrogel plug configured to retract after a substance binds to the hydrogel. A discrete oral component 101 includes an inner cavity containing a stimuli-responsive hydrogel 1800 and a reservoir 1820. In this example, the reservoir 1820 includes a dye or coloring agent such as those described herein. The discrete oral component 101 also includes an internal visualization region 1815, which is configured to allow detection of color through the surface of the discrete oral component 101 by an external device or individual. As shown in FIG. 18A, the hydrogel 1800 is configured to include a plug 1805 blocking the flow of material from the reservoir 1820 into the internal visualization region 1815 through an aperture 1810. As shown in FIG. 18B, after binding of a substance 220, such as influenza virions, the hydrogel 1800 contracts and the plug 1805 no longer prevents movement of stored material from the reservoir 1820 into the internal visualization region 1815 through an aperture 1810. Stored material, such as a dye such as those described herein, may then diffuse into the internal visualization region 1815 through an aperture 1810. The material may then be visualized by an external device such as those described herein, or visually by an individual. The internal visualization region 1815 may also include an additional component that enhances detection of the material, such as a reactive material that, in combination with the released material, creates or enhances detectable color changes.

Alternatively, discrete oral components may contain piezoresistive micro-cantilevers that are coated on one face with a hydrogel including recognition elements, wherein the hydrogel is configured to swell or contract upon binding of the recognition elements to anti-influenza antibodies present in salivary fluids. IgA, IgM and IgG antibodies specific for influenza virus can be detected in salivary fluid from vaccinated individuals. See Moldoveanu et al, "Human immune responses to influenza virus vaccines administered by systemic or mucosal routes," Vaccine, 13:1006-1012 (1995) which is herein incorporated by reference. Hydrogels with covalently coupled (for methods see Miyata et al, Ibid.) influenza viral particles or influenza viral protein antigens (e.g. nucleoprotein or hemagglutinin) are coated on one face of a micro-cantilever and used to detect anti-influenza antibodies in salivary fluid. Micro-cantilever also act as valves on a reservoir of dye molecules that can be configured to be induced, resulting in deflection and release of the dye molecules (see Boisen, et al., "Rapid molecular detection of food- and water-borne diseases," *Microbiology Today,* 116-118 (2007), which is herein incorporated by reference). For example, colorimetric changes in a transparent plastic discrete oral component with a micro-cantilever controlling release of a dye (e.g. Phenol red, Trypan blue, Congo red, Bromocresol purple, Ethyl orange; all available from Sigma-Aldrich, St. Louis, Mo.) in the oral component signals the presence of influenza virions in saliva. For example, micro-cantilevers (available from Veeco Instruments, CA) are coated on one side with a hydrogel (as described in Liu et al, "Detection of $Pb^{2+}$ using a hydrogel swelling microcantilever sensor," *Analytical Sciences,* 20: 9-11 (2004) which is herein incorporated by reference) containing influenza viral particles (e.g. influenza A/New Caledonia/H1N1 obtained from Center for Disease Control, Atlanta, Ga.). Contraction of the hydrogel following binding of anti-influenza antibodies causes measurable deflection of the micro-cantilever in proportion to the concentration of anti-influenza antibodies (see Liu et al, Ibid. and Wee et al, Ibid.). The piezoresistive response and corresponding electronic signal are received by the external device and correlated with known responses to known concentrations of anti-influenza antibodies. Furthermore, calculated antibody concentrations can be integrated with other medical data including for example, medical history, vaccination schedule, clinical evaluation and environmental factors.

Example 2

A Noninvasive System to Detect *Heliobacter pylori* with a Discrete Oral Component, a Sensor and an External Device A system to detect *Heliobacter pylori* (*H. pylori*) that captures, senses and reports the relative amount of carbon dioxide ($CO_2$) derived from isotopically-labeled uric acid can be used to screen patients with dyspepsia for potential *H. pylori* infection or to assess the eradication of *H. pylori* after therapy. *H. pylori* residing in the gastrointestinal tract have high amounts of urease that efficiently releases $CO_2$ from ingested uric acid, and this $CO_2$ is detectable in the breath of infected individuals. By feeding patients uric acid, such as labeled ($^{14}C$-labeled uric acid or $^{13}C$-labeled uric acid) and analyzing the relative amount of $CO_2$ or $^{13}CO_2$ exhaled, it is possible to detect *H. pylori* and other microbes (see Pathak et al, "Urea breath test for *Heliobacter pylori* detection: present status," *Tropical Gastroenterology*, 25: 156-161 (2004) which is herein incorporated by reference).

A discrete oral component with a durable plastic shell and semi-permeable membranes to allow gasses such as $CO_2$ passage into the interior of the oral component is used to trap $CO_2$. For example, a discrete oral component may include a selective medium such as a hydrophobic membrane (such as fluorinated ethylene-propylene; see Potter and DeMarse, "A new approach to neural cell culture for long-term studies," *J. Neurosc. Meth.*, 110: 17-24, (2001)) configured to allow passage of $CO_2$ into an internal module of the discrete oral element. The internal module contains a retaining element such as a trapping solution, for example 1-2 milliliters of 0.5 moles/liter ethanolic hyamine hydroxide. Ethanolic hyamine hydroxide will capture and retain $^{14}CO_2$ (e.g. Pathak et al, Ibid.). The trapping solution may also contain a pH indicator, such as phenolpthalein or thymolpthalein, configured to signal by color change when a predetermined amount of $CO_2$ (e.g. 1 millimole) has been captured (see Pathak et al, Ibid). A discrete oral component configured to contain a $CO_2$ trapping solution is totally enclosed in the oral cavity of patients at least 10 minutes after ingestion of approximately 37 kBq (1 µCi) of $^{14}C$-urea (see Balon et al, "Society of Nuclear Medicine Procedure Guideline for C-14 Urea Breath Test" version 3.0, approved Jun. 23, 2001, *Society of Nuclear Medicine Procedure Guidelines Manual*, June 2002, which is herein incorporated by reference). The discrete oral component is removed after 5-30 minutes in the mouth and the module with the trapping solution is removed and evaluated by a radioactive detector associated with the external device. For example, a radiation detector such as that associated with the portable Ion Ferret™ Beta/Gamma Meter available from Overhoff Technology Corporation (Milford, Ohio) would be operably associated with the external device and would measure the $^{14}CO_2$ levels. Alternatively, the module and trapping solution are added to scintillation fluid and levels of $^{14}C$ radioactivity are counted in a scintillation counter associated with the external device. For example, the external device would include a detector such as that used in the Lumi-Scint 1000 LSC, a portable instrument designed for the rapid qualitative analysis of low-energy beta-emitting radionuclides (Innovative Technology Summary Report DOE/EM-0596, OST/TMS ID 2311, July 2001, which is herein incorporated by reference). Alternatively, the discrete oral component may be configured to include a scintillation vial within an internal module, such as a reservoir. In such, a configuration, scintillation fluid is added to the module of the discrete oral component containing the trapping solution, after 5-30 minutes of exposure to salivary fluid in an individual's mouth, followed by quantifying $^{14}C$ radioactivity with an external scintillation counter. As a control, an identical discrete oral component configured to include trapping solution is completely enclosed in the oral cavity of the same individual for an equivalent time period prior to ingestion of $^{14}C$-urea and the trapping solution analyzed for $^{14}C$ radioactivity to establish a background level of radioactivity. To establish a baseline level of $^{14}CO_2$ radioactivity, a volunteer not infected by *H. Pylori* is fed $^{14}C$-urea and makes use of a discrete oral component on a schedule identical to that for a dyspeptic patient. Calculations and criteria for evaluating patients with respect to *H. pylori* infection are described in Pathak et al, Ibid.

Alternatively or instead, the discrete oral component would contain a pH indicator (see Pathak et al, Ibid.) configured to signal by color change when a sufficient quantity of $CO_2$ has been captured. The transparent, plastic, discrete oral component is removed from the mouth when a color change signals sufficient $CO_2$ has been captured and scintillation fluid is added to the interior of the component prior to evaluating $^{14}CO_2$ radioactivity in an external scintillation counter.

Alternatively, the discrete oral component with a hydrophobic membrane and containing a trapping solution is configured to capture $CO_2$ from patients who have ingested $^{13}C$-urea. To detect *H. pylori*, dyspeptic patients or previously treated *H. pylori* patients are fed approximately 35-250 milligrams of $^{13}C$-urea, and after at least 10 minutes a discrete oral component is placed in the oral cavity to capture $^{13}CO_2$ derived from the enzymatic action of urease from *H. pylori*. A selective hydrophobic membrane configured to selectively allow $CO_2$ passage is used to capture $^{13}CO_2$ inside the oral component where a trapping solution with pH indicator traps $CO_2$ in solution. When a color change in the discrete oral component signals sufficient $CO_2$ has been trapped, the module with the trapping solution containing $^{13}CO_2$, $^{12}CO_2$ and other components is recovered and analyzed in an instrument associated with the external device to determine the ratio of $^{13}CO_2/^{12}CO_2$. For example, the external device would have an integrated infrared light source and detector such as the one described U.S. Pat. No. 6,491,643 issued to Katzman et al., titled "Breath test analyzer" which is incorporated herein by reference.

Once the detector associated with the external device has generated data, circuitry and memory in the external device would process the information into results. Results from the external device are stored in local memory, indicated to at least one system user, and communicated to a network system. Results associated with the same individual on consecutive days may be integrated into a health history or a chronicle for that individual. A health history or chronicle for an individual or group of individuals may be stored in memory in the external device, in the network, or on an additional device.

Example 3

A System to Detect Steroid Hormones Present in Salivary Fluid

A discrete oral component with a hydrogel sensor, a signaling device and a network connection can detect steroid hormone(s) in saliva, indicate the relative amounts of steroid hormone(s) and report the data to a network for integration and correlation with medical information including existing conditions, allergic reactions, age, weight, and vital signs. Such a system may be used in conjunction with ongoing therapies, such as fertility treatments, or during pregnancy.

Because of diurnal and monthly variations, several steroid hormones need multiple samples collected early in the morning or late at night or at the same time every day for a month to give meaningful results. Analysis of salivary fluid with a noninvasive system used at home is accomplished according to the following. Steroid hormones such as estriol, estradiol, progesterone and cortisol are found in salivary fluid at levels that correlate well (e.g. correlation coefficient, R≥0.8) with free steroid hormone levels in the blood (see Hofman, "Human saliva as a diagnostic specimen," *Journal of Nutrition*, 131: 1621S-1625S (2001) which is herein incorporated by reference). Further, analysis of salivary fluid for estriol levels can be used to predict preterm labor. Analyzing estriol in daily saliva samples from a group of pregnant women, it is possible to accurately predict preterm delivery 91% of the time (as shown by Heine et al, "Accuracy of salivary estriol testing compared to traditional risk factor assessment in predicting preterm birth," *Am. J. Obstet. Gynecol.*, 180: s214-

218 (1999) which is herein incorporated by reference). Also by measuring progesterone in salivary fluid samples from normal and infertile women during the menstrual cycle it is possible to identify infertile women based upon salivary fluid progesterone levels (see Walker et al, "Radioimmunoassay of progesterone in saliva: application to the assessment of ovarian function," Clin. Chem. 25: 2030-2033 (1979), which is herein incorporated by reference).

A discrete oral component with a hydrogel sensor that detects steroid hormones and signals via a color change can be used to periodically (e.g. every hour, every 4 hours, every 8 hours, every 12 hours, daily, weekly) assess the level of steroid hormones in saliva. A hydrogel sensor that changes color in response to steroid hormones includes crystalline colloid arrays that are polymerized within a hydrogel. For example, an optical hydrogel sensor can be made from a crystalline colloid array comprised of charged polystyrene spheres that are polymerized within a hydrogel that swells or shrinks in response to an analyte (e.g. see Holtz and Asher, "Polymerized colloidal crystal hydrogel films as intelligent chemical sensing materials," Nature 389: 829-832 (1997) and U.S. Pat. No. 7,105,352 to Asher et al., titled "Intelligent polymerized crystalline colloidal array carbohydrate sensors," which are herein incorporated by reference). Crystalline colloidal arrays diffract light at (visible) wavelengths determined by their lattice spacing, which gives rise to intense colors. Swelling of the hydrogel including the polymerized crystalline colloid array changes the lattice spacing and causes a shift in the Bragg peak of diffracted light to longer wavelengths. The crystalline colloidal array further includes a recognition element, such as an antibody, which specifically recognizes and binds the analyte (see, e.g., Holtz, et al, Ibid and U.S. Pat. No. 6,753,191 to Asher and Reese, titled "Polymerized crystalline colloidal array chemical sensing materials for use in high ionic strength solutions" and U.S. Pat. No. 6,214,546 to Asher et al., titled "Detection of biomolecules," which are herein incorporated by reference). A discrete oral component containing a polymerized crystalline colloid with anti-17β-estradiol antibody and 17β-estradiol (commercially available from Santa Cruz Biotechnology, Inc., Santa Cruz, Calif. or Sigma-Aldrich, St. Louis, Mo.) included in the colloidal hydrogel can be used by patients to test for estradiol in saliva. Oral enclosure of the discrete oral component allows saliva to enter the oral component and contact the recognition elements on the hydrogel, leading to swelling of the hydrogel and a shift in the diffraction wavelength corresponding to a visible color change. For example, polymerized crystalline colloid arrays that recognize analytes respond within approximately 30 seconds to 2 minutes with a visible change in color. To measure the peak diffraction wavelength, the discrete oral component is screened with a spectrometer associated with a handheld external device. For example, the external device includes an integrated spectral sensing system having an energy (light) source and a detector (see e.g. U.S. Patent Application 2008/0265146 to Coates, titled "Integrated sensing module for handheld spectral measurements," and U.S. Pat. No. 7,459,713, to Coates, titled "Sensing system approach for handheld spectral measurements having a disposable sample handling apparatus," which are herein incorporated by reference). The shift in peak diffraction wavelength may be correlated with analyte concentration (see Holtz et al, Ibid.), and the results processed by circuitry in the external device. Results may recorded as digital memory in the external device, an associated network, and/or an additional device (such as a laptop or PDA). Results may be communicated to a system user, such as through an indicator on a user interface device.

A discrete oral component containing a polymerized crystalline colloidal array is fabricated with a durable plastic shell made from a material such as polypropylene. A permeable area of the shell is fabricated from a mesh or lattice of the same material as the shell. An internal cavity of the discrete oral component is configured to enclose an internal module. A module is fabricated from a polymerized crystalline colloid with anti-17β-estradiol antibody and 17β-estradiol conjugated to hydrogel. Before use, the module is placed within the shell and sealed within the shell so that the permeable area is oriented to allow fluid to pass from the oral cavity of a user into the internal cavity and in contact with the module during use.

Alternatively, the discrete oral component containing a polymerized crystalline colloidal array is configured to be reusable following a wash in an analyte free solution. For example, Holtz et al have shown that a polymerized crystalline colloid array sensor used to detect an analyte diffracted light at its original peak wavelength (approximately 450 nm) after being immersed in deionized water and was again responsive to the analyte. Repeat use of a discrete oral component containing a polymerized crystalline colloid array with a steroid hormone sensor may be employed to periodically assess estriol levels or progesterone levels over the course of a menstrual cycle.

A result as determined, for example from data generated by the spectrometer in the external device, is be reported by the external device to at least one system user. The discrete oral component is evaluated with an external device that measures the peak wavelength of diffraction and communicates the wavelength data, date, time, and identity of the patient to the system for data storage and indication to a system user. For example, a result may be directly displayed on the external device, or it may be communicated to a network system that stores information such as the color response of the oral component, date, time and identity of the individual whose saliva was tested.

The state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. For example, the optical aspects of implementations will typically employ optically-oriented hardware, software, and or firmware.

In some implementations described herein, logic and similar implementations may include software or other control structures. Electronic circuitry, for example, may have one or more paths of electrical current constructed and arranged to implement various functions as described herein. In some implementations, one or more media may be configured to bear a device-detectable implementation when such media hold or transmit a device detectable instructions operable to perform as described herein. In some variants, for example, implementations may include an update or modification of existing software or firmware, or of gate arrays or programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or invoking circuitry for enabling, triggering, coordinating, requesting, or otherwise causing one or more occurrences of virtually any functional operations described herein. In some variants, operational or other logical descriptions herein may be expressed as source code and compiled or otherwise invoked as an executable instruction sequence. In some contexts, for example, implementations may be provided, in whole or in part, by source code, such as C++, or other code sequences. In other implementations, source or other code implementation, using commercially available and/or techniques in the art, may be compiled, implemented, translated, or converted into a high-level descriptor language (e.g., initially implementing described technologies in C or C++ programming language and thereafter converting the programming language implementation into a logic-synthesizable language implementation, a hardware description language implementation, a hardware design simulation implementation, and/or other such similar mode(s) of expression). For example, some or all of a logical expression (e.g., computer programming language implementation) may be manifested as a Verilog-type hardware description (e.g., via Hardware Description Language (HDL) and/or Very High Speed Integrated Circuit Hardware Descriptor Language (VHDL)) or other circuitry model which may then be used to create a physical implementation having hardware (e.g., an Application Specific Integrated Circuit). Those skilled in the art will recognize how to obtain, configure, and optimize suitable transmission or computational elements, material supplies, actuators, or other structures in light of these teachings.

In a general sense, the various aspects described herein can be implemented, individually and/or collectively, by a wide range of hardware, software, firmware, and/or any combination thereof and can be viewed as being composed in part of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). The subject matter described herein may be implemented in an analog or digital fashion or some combination thereof.

At least a portion of the devices and/or processes described herein can be integrated into a data processing system. A data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

The herein described components (e.g., operations), devices, objects, and the discussion accompanying them are used as examples for the sake of conceptual clarity and various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting. The foregoing specific exemplary processes and/or devices and/or technologies are representative of more general processes and/or devices and/or technologies taught elsewhere herein, such as in the claims filed herewith and/or elsewhere in the present application.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

It is common within the art to implement devices and/or processes and/or systems, and thereafter use engineering and/or other practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Examples of such other devices and/or processes and/or systems might include—as appropriate to context and application—all or part of devices and/or processes and/or systems of (a) an air conveyance (e.g., an airplane, rocket, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a Voice over IP system, etc.), (f) a business entity (e.g., an Internet Service Provider (ISP) entity such as Comcast Cable, Qwest, Southwestern Bell, etc.), or (g) a wired/wireless services entity (e.g., Sprint, Cingular, Nextel, etc.), etc.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory). A sale of a system or method may likewise occur in a territory even if components of the system or method are located and/or used outside the territory. Further, implementation of at least part of a system for performing a method in one territory does not preclude use of the system in another territory.

All of the above U.S. patents, U.S. patent application publications, U.S. patent applications, foreign patents, foreign patent applications and non-patent publications referred to in this specification and/or listed in any Application Data Sheet, are incorporated herein by reference, to the extent not inconsistent herewith.

While particular aspects of the present subject matter described herein have been shown and described, it will be apparent that, based upon the teachings herein, changes and modifications may be made without departing from the subject matter described herein and its broader aspects and, therefore, the appended claims are to encompass within their scope all such changes and modifications as are within the true spirit and scope of the subject matter described herein. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). If a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense of the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense of the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, recited operations therein may generally be performed in any order. Also, although various operational flows are presented in sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

The various aspects and embodiments disclosed herein are for purposes of illustration and are not intended to be limiting, with the true scope and spirit being indicated by the following claims.

What is claimed is:

1. A system for detecting one or more analyte in salivary fluid, comprising:
    a discrete oral component configured for complete enclosure in a human oral cavity without protrusion therefrom or attachment thereto, the discrete oral component configured to release at least one medicinal agent responsive to the presence of a substance in the salivary fluid;
    at least one sensor incorporated within the discrete oral component and configured for removal therefrom, wherein the sensor specifically identifies the one or more analyte in the salivary fluid and generates a signal that the identification has been made; and
    an external device including a port including a cavity configured for physical contact with the discrete oral component and including one or more devices for detection of the signal from the sensor.

2. The system of claim 1, comprising:
    at least one flavorant, wherein the discrete oral component releases the at least one flavorant through passive displacement during contact with salivary fluid.

3. The system of claim 1, wherein the discrete oral component comprises:
    at least one signaling element configured to signal contact with salivary fluid after a preset period of time.

4. The system of claim 1, wherein the discrete oral component includes at least one selective medium including cellulose with pores sized to allow diffusion of certain sized molecules.

5. The system of claim 1, wherein at least a portion of the discrete oral component is in a dehydrated form prior to contact with salivary fluid.

6. The system of claim 1, wherein at least a portion of the discrete oral component is an electronic chip sensor module configured for removal from the discrete oral component and replacement.

7. The system of claim 1, wherein the discrete oral component includes a transmucosal sampling mechanism.

8. The system of claim 1, wherein the discrete oral component comprises:
    at least one recognition element configured to recognize a substance.

9. The system of claim 1, wherein the discrete oral component comprises:
    at least one compound configured to be physiologically incorporated into a body of a user; and
    at least one matrix configured to retain the at least one compound until the at least one compound contacts the salivary fluid.

10. The system of claim 1, wherein the discrete oral component comprises:
    at least one reservoir including the at least one medicinal agent therein, wherein the at least one reservoir is operably connected to one or more time sensing device.

11. The system of claim 1, wherein the at least one sensor includes at least one biosensor including a piezoresistive micro-cantilever.

12. The system of claim 1, wherein the at least one sensor includes at least one chemical sensor including a single-walled carbon nanotube capacitor.

13. The system of claim 1, wherein the at least one sensor is a cantilever-based sensor that is configured to be directly responsive to at least one of the one or more analyte.

14. The system of claim 1, wherein the at least one sensor is configured to be responsive to a metabolite of at least one of the one or more analyte.

15. The system of claim 1, wherein the external device is configured to communicate with a network.

16. The system of claim 1, wherein the one or more analyte comprises:
    at least one metabolite, wherein the metabolite is a metabolic product generated by physiology of a user of the discrete oral component.

17. The system of claim 1, comprising:
    an instrument for placement and retrieval of the discrete oral component.

18. A method for detecting one or more analyte in salivary fluid comprising:
    swallowable positioning a discrete oral component within an oral cavity, wherein the discrete oral component is configured to be completely enclosed in the oral cavity without protrusion therefrom or attachment thereto and includes one or more flavorant;
    identifying the one or more analyte in salivary fluid with at least one sensor integral to the discrete oral component;
    generating a first signal from the at least one sensor that the one or more analyte has been identified;
    detecting the first signal from the at least one sensor with at least one external device;
    releasing one or more agent responsive to the use of the discrete oral component;
    identifying the one or more agent or a metabolite of the one or more agent in the salivary fluid with the at least one sensor;
    generating a second signal from the at least one sensor that the one or more agent or the metabolite of the one or more agent has been identified; and
    detecting the second signal from the at least one sensor with the at least one external device.

19. The method of claim 18, wherein identifying the one or more analyte comprises:
    collecting a sample of salivary fluid with the discrete oral component.

20. The method of claim 18, wherein identifying the one or more analyte comprises:
    providing one or more flavorant configured to be responsive to a physical condition of the discrete oral component, wherein the discrete oral component releases the at least one flavorant through passive displacement.

21. The method of claim 18, wherein identifying the one or more analyte comprises:
    binding one or more analyte with a recognition element.

22. The method of claim 18, wherein identifying the one or more analyte comprises:
    sequestering at least one of the one or more analyte with the discrete oral component.

23. The method of claim 18, wherein identifying the one or more analyte comprises:
    transmucosal sampling.

24. The method of claim 18, wherein identifying the one or more analyte comprises:

identifying at least one metabolite, wherein the metabolite is a metabolic product generated by physiology of a user of the discrete oral component.

25. The method of claim 18, wherein identifying the one or more analyte comprises:
identifying one or more analyte within the salivary fluid with at least one biosensor wherein the at least one biosensor includes a piezoresistive micro-cantilever.

26. The method of claim 18, wherein identifying the one or more analyte comprises:
identifying one or more analyte within the salivary fluid with at least one chemical sensor, wherein the at least one chemical sensor includes a single-walled carbon nanotube capacitor.

27. The method of claim 18, wherein identifying the one or more analyte comprises:
identifying one or more analyte directly.

28. The method of claim 18, wherein identifying the one or more analyte comprises:
identifying one or more metabolite of the one or more analyte.

29. The method of claim 18, comprising:
providing an agent with the discrete oral component, wherein the agent is configured to be physiologically incorporated by the user of the discrete oral component.

30. The method of claim 18, comprising:
collecting and storing multiple results from the at least one sensor.

31. The method of claim 18, comprising:
processing the information from the at least one sensor into at least one result;
associating the at least one result with a physiologic state of the user of the discrete oral component; and
communicating, with the at least one external device, the at least one result and an association to at least one system user.

32. The method of claim 18, comprising:
communicating, with the at least one external device, the identification of the analyte by the sensor within the discrete oral component to at least one system user.

33. The method of claim 18, comprising:
storing the information from the at least one sensor, detected at multiple time points from a single individual.

34. The method of claim 18, comprising:
collecting the salivary fluid with the discrete oral component; and
analyzing collected salivary fluid with the at least one sensor.

35. The method of claim 18, comprising:
communicating a result from an external communication device to one or more network;
receiving information associated with the result from at least one of the one or more network; and
categorizing the result in relation to the information.

36. A method for providing information relating to a health history for at least one individual comprising:
swallowable positioning a discrete oral component within a human oral cavity, wherein the discrete oral component is configured to be completely enclosed in the human oral cavity without protrusion therefrom or attachment thereto and includes one or more flavorant;
sampling salivary fluid at a first time point from the at least one individual utilizing the discrete oral component, the discrete oral component further including at least one diagnostic agent configured for release during use of the discrete oral component;
releasing the at least one diagnostic agent from the discrete oral component at the first time point;
identifying, with at least one sensor incorporated within the discrete oral component, one or more analyte in the salivary fluid from the at least one individual at the first time point;
generating a first signal from the at least one sensor, wherein the first signal is generated as a consequence of the identification of the one or more analyte;
identifying, with the at least one sensor, the at least one diagnostic agent or a metabolite of the at least one diagnostic agent in the salivary fluid from the at least one individual at a second time point;
generating a second signal from the at least one sensor, wherein the second signal is generated responsive to the identification of the at least one diagnostic agent or a metabolite of the at least one diagnostic agent in the salivary fluid;
detecting the first signal and the second signal with an external device including a port including a cavity configured for physical contact with the discrete oral component and including one or more devices for detection of the signal from the sensor;
processing, in the external device, the first signal from the at least one sensor into at least one first result and the second signal from the at least one sensor into at least one second result;
storing the at least one first result and the at least one second result integrated into the health history for the at least one individual in memory; and
indicating the at least one first result and the at least one second result to at least one system user.

37. The method of claim 36, wherein indicating the at least one first result to at least one system user comprises:
communicating the at least one first result to at least one system user through at least one network.

38. The method of claim 36, comprising:
identifying, with at least one sensor incorporated within the discrete oral component, presence of one or more analyte in salivary fluid from the at least one individual at a second time point;
generating a second signal from the at least one sensor, wherein the second signal is generated as a consequence of the identification at the second time point;
detecting the signal with an external device;
processing, in the external device, the second signal from the at least one sensor into at least one second result;
processing the at least one first result and the at least one second result into a health history for the at least one individual;
storing a record of the health history; and
indicating at least a subset of the health history to at least one system user.

39. A system for detecting one or more analyte in salivary fluid, comprising:
a discrete oral component configured for complete enclosure in a human oral cavity without protrusion, the discrete oral component including a shell with a permeable area and a removable module therein;
at least one sensor configured to sense the one or more analyte in salivary fluid, the at least one sensor incorporated within the removable module, the at least one sensor including a reversibly antigen-responsive hydrogel core and at least one type of antibody corresponding to a viral protein; and an external device including a port configured for size measurement of the removable module, the port including a cavity configured for physical contact with the discrete oral component.

40. A system for detecting one or more analyte in salivary fluid, comprising:
- a discrete oral component configured for complete enclosure in a human oral cavity without protrusion therefrom or attachment thereto, the discrete oral component including a shell, the shell including a permeable area having an outermost porous covering and a selective medium internal to the shell, the discrete oral component configured to release at least one medicinal agent responsive to a substance in the salivary fluid;
- at least one sensor configured to:
  - identify the one or more analyte in the salivary fluid;
  - generate a first signal indicative of the identification of the one or more analyte;
  - identify the at least one medicinal agent in the salivary fluid or a metabolite of the at least one medicinal agent in the salivary fluid; and
  - generate a second signal indicative of the identification of the at least one medicinal agent or the metabolite of the at least one medicinal agent in the salivary fluid; and
- an external device including at least one device configured to detect the first and the second signals from the at least one sensor, and including a port with a cavity configured for physical contact with the discrete oral component.

* * * * *